(12) United States Patent
Schalk

(10) Patent No.: US 8,586,328 B2
(45) Date of Patent: Nov. 19, 2013

(54) METHOD FOR PRODUCING SCLAREOL

(75) Inventor: Michel Schalk, Collonges-sous-Saleve (FR)

(73) Assignee: Firmenich SA, Geneva (CH)

( * ) Notice: Subject to any disclaimer, the term of this patent is extended or adjusted under 35 U.S.C. 154(b) by 172 days.

(21) Appl. No.: 12/867,861

(22) PCT Filed: Feb. 12, 2009

(86) PCT No.: PCT/EP2009/051620
§ 371 (c)(1),
(2), (4) Date: Aug. 16, 2010

(87) PCT Pub. No.: WO2009/101126
PCT Pub. Date: Aug. 20, 2009

(65) Prior Publication Data
US 2011/0041218 A1    Feb. 17, 2011

(30) Foreign Application Priority Data
Feb. 15, 2008   (EP) .................................. 08101655

(51) Int. Cl.
| C12N 1/15 | (2006.01) |
| C12N 15/70 | (2006.01) |
| C12N 1/19 | (2006.01) |
| C12N 15/29 | (2006.01) |
| C12N 15/62 | (2006.01) |
| C12N 15/74 | (2006.01) |
| C12N 15/80 | (2006.01) |
| C12N 15/81 | (2006.01) |
| C12N 15/82 | (2006.01) |
| C07K 14/415 | (2006.01) |

(52) U.S. Cl.
USPC . 435/69.1; 435/69.7; 435/252.3; 435/254.11; 435/320.1; 435/419; 435/468; 435/471; 800/278; 800/298; 530/370; 536/23.4

(58) Field of Classification Search
USPC .......................................................... 800/278
See application file for complete search history.

(56) References Cited

U.S. PATENT DOCUMENTS
2010/0311134 A1    12/2010    Schalk

FOREIGN PATENT DOCUMENTS
WO    WO 2008/007031 A1    1/2008
WO    WO/2012/058636    *    5/2012

OTHER PUBLICATIONS

GenBank Accession No. ABV57835.1 [online], [retrieved on Sep. 12, 2012], retrieved from the internet <http://www.ncbi.nlm.nih.gov/protein/ABV57835.1>.*

(Continued)

Primary Examiner — Cynthia Collins
Assistant Examiner — Rebecca Coobs
(74) Attorney, Agent, or Firm — Scully, Scott, Murphy & Presser, P.C.

(57) ABSTRACT

The present invention provides a method of producing sclareol, said method comprising contacting a particular polypeptide having a sclareol synthase activity with labdenediol diphosphate (LPP). In particular, said method may be carried out in vitro or in vivo to produce sclareol, a very useful compound in the fields of perfumery and flavoring. The present invention also provides the amino acid sequence of the polypeptide used in the method. A nucleic acid derived from *Salvia sclarea* and encoding the polypeptide of the invention, an expression vector containing said nucleic acid, as well as a non-human host organism or a cell transformed to harbor the same nucleic acid, are also part of the present invention.

30 Claims, 15 Drawing Sheets

(56) References Cited

OTHER PUBLICATIONS

Guo et al., Protein tolerance to random amino acid change, 101 PNAS 9205-9210 (2004).*

Banthorpe, Derek V. et al., "Accumulation of the Anti-Fungal Diterpene Sclareol by Cell Cultures of *Saliva sclarea and Nicotiana glutinosa*" *Phytochemistry*, 29(7), 2145-2148 (1990).

Banthorpe, Derek V. et al., "Partial Purification of Farnesyl Pyrophosphate: Drimenol Cyclase and Geranylgeranyl Pyrophosphate: Sclareol Cyclase, Using Cell Culture as a Source of Material" *Phytochemistry*, 31(10), 3391-3395 (1992).

Guo, Zhenhua et al., "Biosynthesis of labdencdiol and sclareol in cell-free extracts from trichomes of *Nicotiana glutinosa*" *Planta*, 197, 627-632 (1995).

Wang, Erming et al., "Elucidation of the functions of genes central to diterpene metabolism in tobacco trichomes using posttranscriptional gene silencing" *Planta*, 216, 686-691 (2003).

Altschul, Stephen F., "Amino Acid Substitution Matrices from an Information Theoretic Perspective" *J. Mol. Biol.*, 219, 555-565 (1991).

Altschul, Stephen F. et al., "Basic Local Alignment Search Tool" *J. Mol. Biol.*, 215, 403-410 (1990).

Dewick, Paul M., "The biosynthesis of $C_5$-$C_{25}$ terpenoid compounds" *Nat. Prod. Rep.*, 19, 181-222 (2002).

Emanuelsson, Olof et al., "ChloroP, a neural network based method for predicting chloroplast transit peptides and their cleavage sites" *Protein Science*, 8, 978-984 (1999).

Hernandez, David et al., "De novo bacterial genome sequencing: Millions of very short reads assembled on a desktop computer" *Genome Res.*, 18, 802-809 (2008).

Horton, Robert M. et al., "Engineering hybrid genes without the use of restriction enzymes: gene splicing by overlap extension" *Gene*, 77, 61-68 (1989).

Huang, Xiaoqiu "A Contig Assembly Program Based on Sensitive Detection of Fragment Overlaps" *Genomics*, 14, 18-25 (1992).

Huang, Qiulong et al., "Engineering *Escherichia coli* for the synthesis of Tazadiene, a Key Intermediate in the Biosynthesis of Taxol" *Bioorganic & Medicinal Chemistry*, 9, 2237-2242 (2001).

Keller, R. Kennedy et al., "Rapid synthesis of isoprenoid diphosphates and their isolation in one step using either thin layer or flash chromatography" *Journal of Chromatography*, 645, 161-167 (1993).

Margis-Pinheiro, Marcia et al., "Isolation and characterization of *Ds*-tagged rice (*Oryza sativa* L.) GA-responsive dwarf mutant defective in an early step of the gibberellins biosynthesis pathway" Plant Cell Rep, 23, 819-833 (2005).

Schardl, Christopher L. et al., "Design and construction of a versatile system for the expression of foreign genes in plants" *Gene.*, 61, 1-11 (1987).

Stemmer, Willem P.C., "DNA shuffling by random fragmentation and reassembly: in vitro recombination for molecular evolution" *Proc. Natl. Acad. Sci. USA*, 91, 10747-10751 (1994).

Tatusova, Tatiana A. et al., "BLAST 2 Sequences, a new tool for comparing protein and nucleotide sequences" *FEMS Microbiology Letters*, 174, 247-250 (1999).

Wendt, K Ulrich et al., "Isoprenoid biosynthesis: manifold chemistry catalyzed by similar enzymes" *Structure*, 6, 127-133 (1998).

Xu Meimi et al.; "Functional characterization of the rice kaurene synthase-like gene family" *Phytochemistry*, 68, 312-326 (2007).

US Final Official Action dated Apr. 30, 2013 issued in related U.S. Appl. No. 12/865,298.

* cited by examiner

```
                        10        20        30        40        50        60        70        80
                 ....|....|....|....|....|....|....|....|....|....|....|....|....|....|....|....|..
Sa3-full-length  MTSVNLSRAPAAITRRRLQLQPEPHAECSWLKSSSKHAPLTLSCQIRPKQLSQIAELRVTSLDASQASEKDISLVQTPHKVEVNEKI
Sa3-del1                          MLQLQPEPHAECSWLKSSSKHAPLTLSCQIRPKQLSQIAELRVTSLDASQASEKDISLVQTPHKVEVNEKI
Sa3-del2                                          MHAPLTLSCQIRPKQLSQIAELRVTSLDASQASEKDISLVQTPHKVEVNEKI
Sa3-del3                                                          MIAELRVTSLDASQASEKDISLVQTPHKVEVNEKI
Sa3-del4                                                                          MASQASEKDISLVQTPHKVEVNEKI
```

B

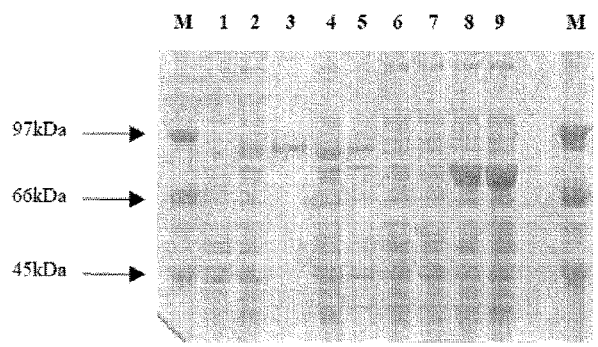

Figure 9

```
              10         20         30         40         50         60         70         80         90        100        110        120
               |          |          |          |          |          |          |          |          |          |          |          |
SsTps1132  ....:....|....:....|....:....|....:....|....:....|....:....|....:....|....:....|....:....|....:....|....:....|....:....|
           MSLAFNVGTPFSGQRVGSRKEKFPVQGFPVTTPNRSRLIVNCSLTTIDFMAKMKENFKREDDKFPTTTLRSEDIPSNLCIIDTLQRLGVDQFFQYEINTILDNTFRLWQEKHKVIYGN
1132-2-5   ------------------------------------------MAKMKENFKREDDKFPTTTLRSEDIPSNLCIIDTLQRLGVDQFFQYEINTILDNTFRLWQEKHKVIYGN 130        140        150        160        170        180        190        200        210        220        230        240
               |          |          |          |          |          |          |          |          |          |          |          |
SsTps1132  ....:....|....:....|....:....|....:....|....:....|....:....|....:....|....:....|....:....|....:....|....:....|....:....|
           VTTHAMAFRLLRVKGYEVSSEELAPYGNQEAVSQQTNDLPMIIELYRAANERIYEEERSLEKILAWTTIFLNKQVQDNSIPDKKLHKLVEFYLRNYKGITIRLGARRNLELYDMTYYQAL
1132-2-5   VTTHAMAFRLLRVKGYEVSSEELAPYGNQEAVSQQTNDLPMIIELYRAANERIYEEERSLEKILAWTTIFLNKQVQDNSIPDKKLHKLVEFYLRNYKGITIRLGARRNLELYDMTYYQAL 250        260        270        280        290        300        310        320        330        340        350        360
               |          |          |          |          |          |          |          |          |          |          |          |
SsTps1132  ....:....|....:....|....:....|....:....|....:....|....:....|....:....|....:....|....:....|....:....|....:....|....:....|
           KSTNRFSNLCNEDFLVFAKQDFDIHEAQNQKGLQQLQRWYADCRLDTLNFGRDVVIIANYLASLIIGDHAFDYVRLAFAKTSVLVTIMDDFFDCHGSSQECDKIIELVKEWKENPDAEYG
1132-2-5   KSTNRFSNLCNEDFLVFAKQDFDIHEAQNQKGLQQLQRWYADCRLDTLNFGRDVVIIANYLASLIIGDHAFDYVRLAFAKTSVLVTIMDDFFDCHGSSQECDKIIELVKEWKENPDAEYG 370        380        390        400        410        420        430        440        450        460        470        480
               |          |          |          |          |          |          |          |          |          |          |          |
SsTps1132  ....:....|....:....|....:....|....:....|....:....|....:....|....:....|....:....|....:....|....:....|....:....|....:....|
           SEELEILFMALYNTVNELAERARVEQGRSVKEFLVKLMVEILSAFKIELDTWSNGTQQSFDEYISSSWLSNGSRLTGLLITMQFVGVKLSDEMLMSEECTDLARHVCMVGRLLNDVCSSER
1132-2-5   SEELEILFMALYNTVNELAERARVEQGRSVKEFLVKLMVEILSAFKIELDTWSNGTQQSFDEYISSSWLSNGSRLTGLLITMQFVGVKLSDEMLMSEECTDLARHVCMVGRLLNDVCSSER 490        500        510        520        530        540        550        560        570
               |          |          |          |          |          |          |          |          |
SsTps1132  ....:....|....:....|....:....|....:....|....:....|....:....|....:....|....:....|....:....|
           ERREENIAGKSYSILLATEKDGRKVSEDEAIAEINEMVEYHWRKVLQIVYKKESILPRRCKDVFLEMAKGTFYAYGINDELTSPQQSKEDMKSFVF
1132-2-5   ERREENIAGKSYSILLATEKDGRKVSEDEAIAEINEMVEYHWRKVLQIVYKKESILPRRCKDVFLEMAKGTFYAYGINDELTSPQQSKEDMKSFVF
```

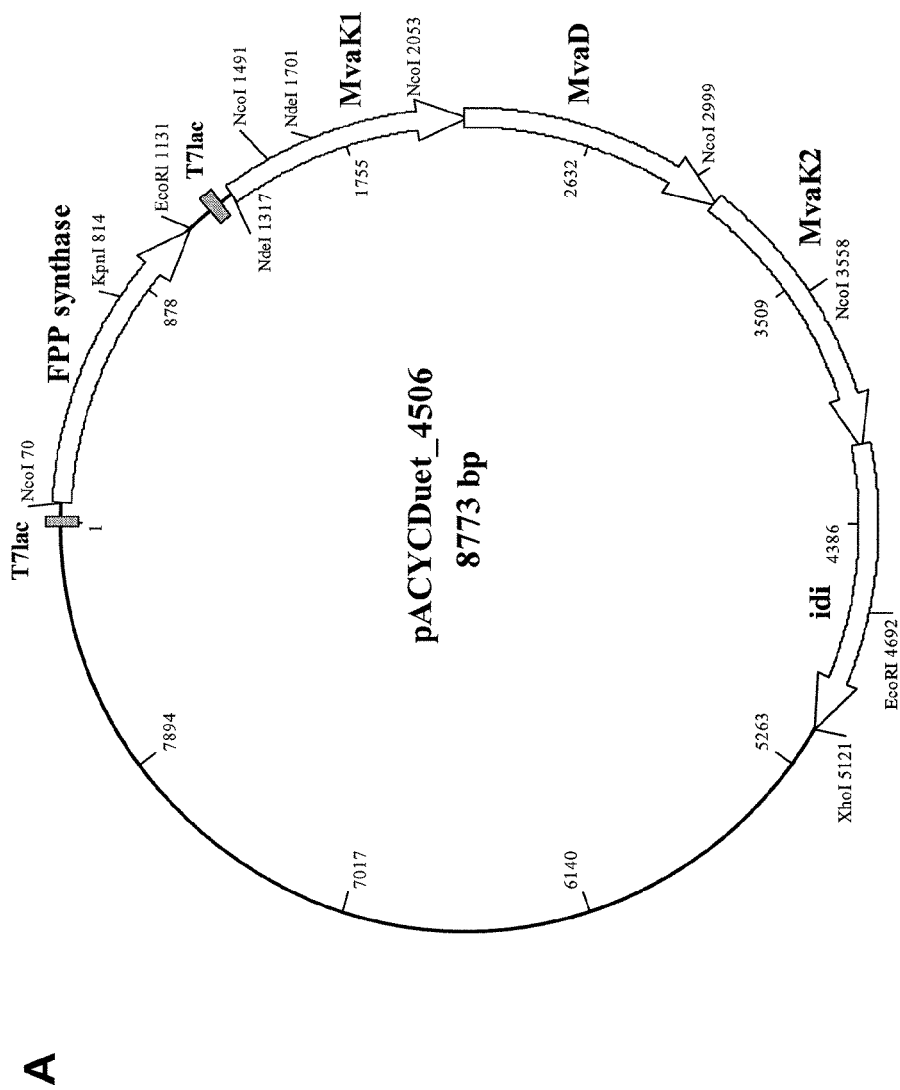
Figure 13 (1st part)

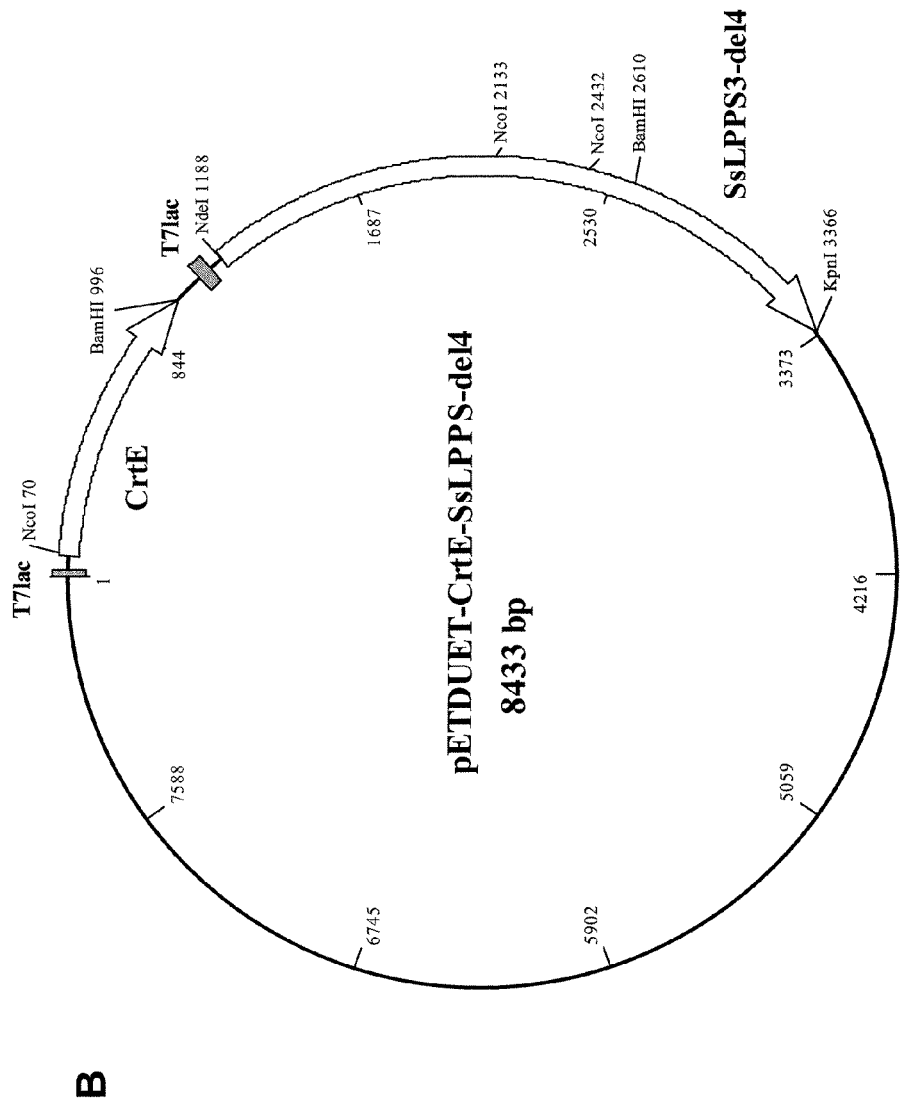
Figure 13 (2nd part)

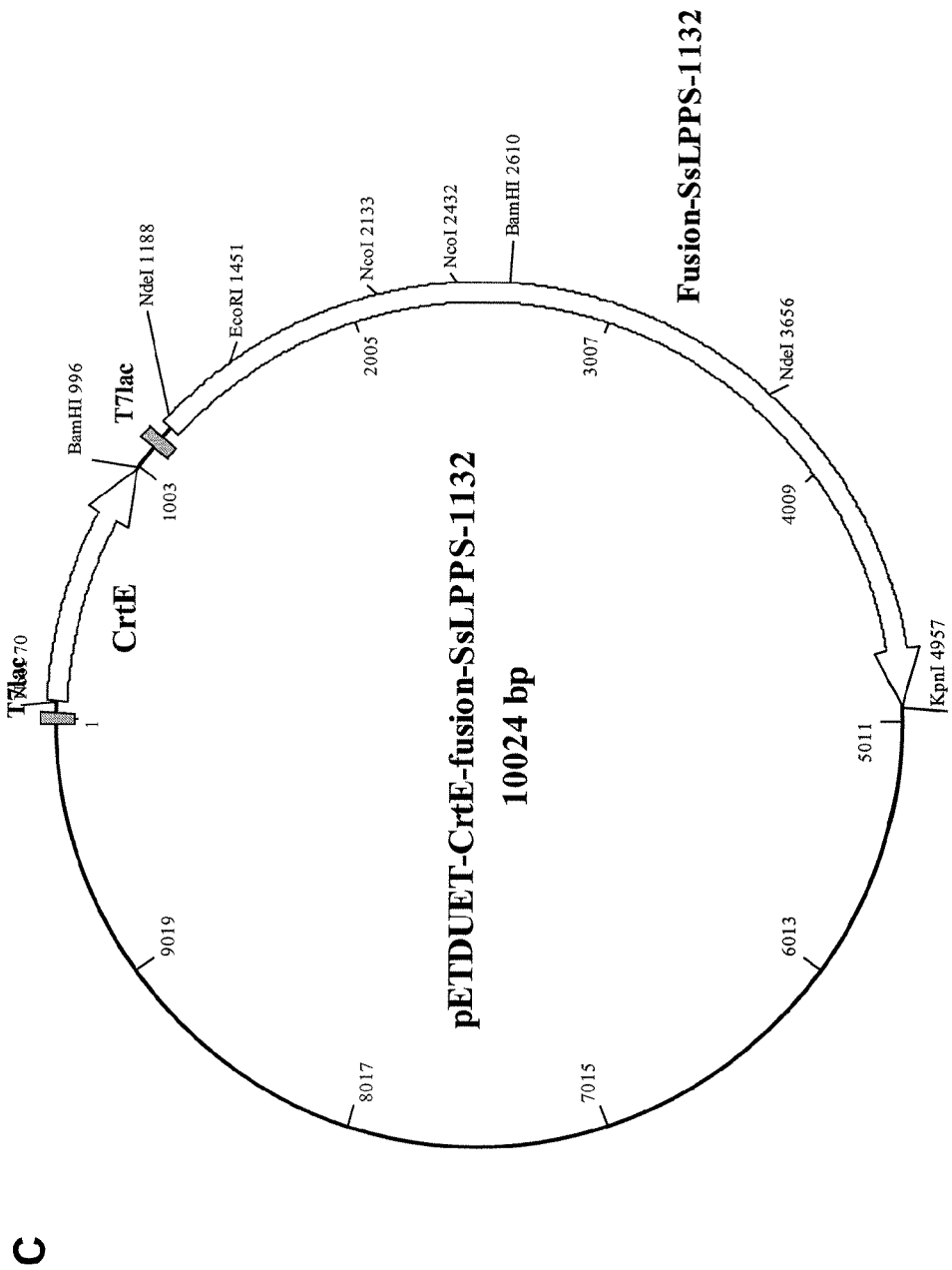
Figure 13 (3rd part)

ns and are related to
either the protonation or the ionization dependent cyclization.
A DDxxD motif (wherein x represents any amino acid) is
found in several class I diterpene synthases. Said motif is
probably involved in binding and ionization of the diphosphate moiety. In class II synthases, a conserved DxDD motif
(wherein x represents any amino acid) is found, in which the
second aspartate residue is involved as proton donor.

METHOD FOR PRODUCING SCLAREOL

RELATED APPLICATION

This application is a '371 of International Application having PCT Serial No. PCT/EP2009/051620 filed on Feb. 12, 2009.

TECHNICAL FIELD

The present invention provides a method of producing sclareol, said method comprising contacting at least one polypeptide with geranylgeranyl pyrophosphate (GGPP). In particular, said method may be carried out in vitro or in vivo to produce sclareol, a very useful compound in the fields of perfumery and flavoring. The present invention also provides the amino acid sequences of a polypeptide useful in the method of the invention. A nucleic acid encoding the polypeptide of the invention and an expression vector containing said nucleic acid are also part of the present invention. A non-human host organism or a cell transformed to be used in the method of producing sclareol is also an object of the present invention.

PRIOR ART

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Diterpenes, for example, are widely found in the plant kingdom and over 2500 diterpene structures have been described (Connolly and Hill, Dictionary of terpenoids, 1991, Chapman & Hall, London). Terpene molecules have been of interest for thousands of years because of their flavor and fragrance properties and their cosmetic, medicinal and antimicrobial effects. Plant extracts obtained by different means such as steam distillation or solvent extraction are used as source of terpenes. Terpene molecules are often used as such, but in some cases chemical reactions are used to transform the terpenes into other high value molecules.

Biosynthetic production of terpenes involves enzymes called terpene synthases. The synthesis of a diterpene can be carried out by a single enzyme or by two or more enzymes. When two enzymes are involved, the first one catalyzes the synthesis of a diterpene diphosphate ester, which is in turn converted to the final product by the second enzyme.

Two types of cyclization mechanisms occur in nature and are related to two types of diterpene synthases which can be classified into class I and class II diterpene synthases (Wendt and Schulz, 1998, Structure. 6(2):127-33). For some diterpenes, the cyclization mechanism is initiated by the ionization of the diphosphate ester function of GGPP, followed by the reaction of the resulting carbocation with an internal double bond. The diterpene synthases catalysing this type of cyclization are class I diterpene synthases. The second mode of cyclization in the biosynthesis of diterpenes, catalyzed by class II diterpene synthases, is initiated by the protonation of the terminal double bond of GGPP and leads, after internal rearrangement and proton elimination, to a cyclic diterpene diphosphate intermediate.

Genes and cDNAs encoding diterpene synthases from each of the two classes have been cloned and the recombinant enzymes characterized. The availability of genes encoding different types of diterpene synthases provides information on the primary structures of the enzymes. Some amino acid motifs are conserved in diterpene synthases and are related to either the protonation or the ionization dependent cyclization. A DDxxD motif (wherein x represents any amino acid) is found in several class I diterpene synthases. Said motif is probably involved in binding and ionization of the diphosphate moiety. In class II synthases, a conserved DxDD motif (wherein x represents any amino acid) is found, in which the second aspartate residue is involved as proton donor.

Sclareol is a naturally occurring diterpene molecule extensively used as starting material for the synthesis of fragrance molecules with ambergris notes. These syntheses were developed to provide an alternative to ambergris, a waxy substance secreted by the intestines of sperm whale. Ambergris is highly appreciated for its pleasant odor and has been historically used as a perfume ingredient. Due to its high price and the increasing demand for ambergris, and particularly due to the protection of the whale species, chemical synthesis of ambergris constituents and molecules with ambergris character have been developed. Amongst these molecules, Ambrox® (registered trademark of Firmenich SA, Switzerland) is the most largely appreciated substitute for Ambergris. The most widely used starting material for the synthesis of Ambrox® is the diterpene-diol sclareol.

Generally, the price and availability of plant natural extracts are dependent on the abundance, oil yield and geographical origin of the plants. In addition, the availability and quality of natural extracts is very much dependent on climate and other local conditions leading to variability from year to year, rendering the use of such ingredients in high quality perfumery very difficult or even impossible some years. Therefore, it would be an advantage to provide a source of sclareol, which is less subjected to fluctuations in availability and quality. Chemical synthesis would seem to be an evident option for the preparation of sclareol. However, given its highly complex structure, an economic synthetic process for the preparation of sclareol is still difficult. A biochemical pathway leading to the synthesis of sclareol would therefore be of great interest.

The biosynthesis of terpenes in plants and other organisms has been extensively studied and is not further detailed in here, but reference is made to Dewick, Nat. Prod. Rep., 2002, 19, 181-222, which reviews the state of the art of terpene biosynthetic pathways.

Several diterpene synthases have already been identified. In particular, terpene synthases having a certain percentage of sequence identity with the sequences of the present invention have also been found in the sequences databases. Nevertheless, the percentage of identity between the known diterpene synthases and the polypeptides of the invention is very low.

The closest synthases to the LPP synthases of the invention are two copalyl diphosphate synthases (one from *Solanum lycopersicum* (BAA84918) and one from *Cucurbita maxima* (AAD04293 and AAD04292)), a putative copalyl diphosphate synthase from *Scoparia dulcis* (BAD91286) and a hypothetical protein from *Vitis vinifera*. The sequences of these proteins share only 41% identity with the LPP synthases of the invention and none of those sequences are described as being useful in the production of sclareol, and as having LPP synthase activity.

The closest synthases to the sclareol synthase of the invention are a terpenoid cyclase of undefined function (Accession number NCBI AAS98912) having 36% identity with the polypeptide of the invention, an ent-kaurene synthase of *Cucumis sativus* (accession number BAB19275) having 32% identity with the polypeptide of the invention, an ent-cassadiene synthase from *Oryza sativa* (accession number ABH10734 and published in Xu, Wilderman, Morrone, Xu, Roy, Margis-Pinheiro, Upadhyaya, Coates and Peters, Functional characterization of the rice kaurene synthase-like gene family, Phytochemistry, 68(3), 2007, 312-326) having 32% identity with the polypeptide of the invention and an ent-kaurene synthase from *Oryza sativa* (accession number AAQ72559 and published in Margis-Pinheiro, Zhou, Zhu, Dennis and Upadhyaya, Isolation and characterization of a DS-tagged rice (*Oryza sativa* L.) GA-responsive dwarf mutant defective in an early step of the gibberellins biosynthesis pathway, Plant Cell Rep., 23(12), 2005, 819-833) having 32% identity with the sclareol synthase provided in the present invention. Moreover, none of those sequences are described as being useful in the production of sclareol and in particular as being capable of catalyzing the transformation of LPP to sclareol.

In addition to the difference between the sequences themselves, it also has to be pointed out that the structure and the properties of the products synthesized by the above-mentioned enzymes are very different from those of sclareol and LPP. The properties of copalyl diphosphate are very different from those of labdenediol diphosphate (LPP). In particular, unlike LPP, copalyl diphosphate is of no use as an intermediate product in the biosynthesis of sclareol. Ent-kaurene and ent-cassadiene are also very different from sclareol. Ent-kaurene is a tricyclic diterpene which does not contain any alcohol functional groups, unlike sclareol, which is a bicyclic diol. Moreover, ent-kaurene, which is a precursor of a plant hormone regulating growth, is of no use in the field of perfumery and flavoring, whereas sclareol is of high interest in these technical fields, as explained above.

One document of the prior art relates specifically to a sclareol synthase (Banthorpe, Brown and Morris, Partial purification of farnesyl pyrophosphate: Drimenol cyclase and geranylgeranyl pyrophosphate: Sclareol cyclase, using cell culture as a source of material, Phytochemistry 31, 1992, 3391-3395). In this reference, a partially purified protein from *Nicotiana glutinosa* is identified as a sclareol synthase, but no indication is given regarding the amino acid sequence of that protein, the nucleotide sequence of the nucleic acid encoding it or the use of that protein in a method for the biosynthesis of sclareol in vitro or in vivo. Moreover, this document does not teach or even suggest that two proteins (a class I and a class II diterpene synthases) are involved in the catalysis of the transformation of GGPP to sclareol. To the contrary, it teaches that one single partially purified protein is responsible for the synthesis of sclareol.

WO 2008/007031 discloses a protein having a syn-copalyl-8-ol diphosphate synthase activity, the nucleotide sequence encoding said protein, as well as a vector and a transgenic non-human organism comprising said nucleic acid. This syn-copalyl-8-ol diphosphate synthase is nevertheless very different from the polypeptide of the invention, because the protein there disclosed has an amino acid sequence only 44% identical to the present LPP synthase used in the methods of the invention of present in the fusion polypeptide of the invention.

It is an objective of the present invention to provide methods for making sclareol in an economic way, as indicated above. Accordingly, the present invention has the objective to produce sclareol while having little waste, a more energy and resource efficient process and while reducing dependency on fossil fuels. It is a further objective to provide enzymes capable of synthesizing sclareol, which is useful as perfumery and/or aroma ingredients.

No document from the prior art discloses a process for the biosynthetic production of sclareol from the acyclic diterpene precursor GGPP.

| Abbreviations Used | |
|---|---|
| bp | base pair |
| kb | kilo base |
| BSA | bovine serum albumin |
| DMAPP | dimethylallyl diphosphate |
| DNA | deoxyribonucleic acid |
| cDNA | complementary DNA |
| dT | deoxy thymine |
| dNTP | deoxy nucleotide triphosphate |
| DTT | dithiothreitol |
| FPP | farnesyl pyrophosphate |
| GC | gaseous chromatograph |
| GGPP | Geranylgeranyl pyrophosphate |
| idi | isopentenyl diphosphate isomerase |
| IPP | isopentenyl diphosphate |
| IPTG | isopropyl-D-thiogalacto-pyranoside |
| LB | lysogeny broth |
| LPP | labdenediol diphosphate |
| MOPSO | 3-(N-morpholino)-2-hydroxypropanesulfonic acid |
| MS | mass spectrometer |
| mvaK1 | mevalonate kinase |
| mvaK2 | mevalonate diphosphate kinase |
| PCR | polymerase chain reaction |
| 3'-/5'-RACE | 3' and 5' rapid amplification of cDNA ends |
| RMCE | recombinase-mediated cassette exchange |
| RT-PCR | reverse transcription - polymerase chain reaction |
| RNA | ribonucleic acid |
| mRNA | messenger ribonucleic acid |
| RuBisCO | ribulose-1,5-bisphosphate carboxylase |
| SDS-PAGE | SDS-polyacrylamid gel electrophoresis |
| SsLPPs | Salvia sclarea labdenediol diphosphate synthase |

DESCRIPTION OF THE INVENTION

The present invention provides a method to biosynthetically produce sclareol in an economic, reliable and reproducible way.

As intended in the present application, sclareol, GGPP, LPP and all other compounds cited in the present application are defined by the way of their formula as represented in FIG. 1.

A "diterpene synthase" or a "polypeptide having a diterpene synthase activity", is intended for the purpose of the present application as a polypeptide capable of catalyzing the synthesis of a terpene molecule from the acyclic terpene precursor GGPP or from a diterpene diphosphate ester such as LPP, or capable of catalyzing the synthesis of a diterpene diphosphate ester from the acyclic diterpene precursor GGPP.

As a "LPP synthase" or as a "polypeptide having a LPP synthase activity", we mean here a polypeptide capable of catalyzing the synthesis of LPP starting from GGPP.

As a "sclareol synthase" or as a "polypeptide having a sclareol synthase activity", we mean here a polypeptide capable of catalyzing the synthesis of sclareol starting from LPP.

As a "polypeptide capable of catalyzing the transformation of GGPP to sclareol" we mean here any polypeptide that is capable of catalyzing said transformation and in particular polypeptides that catalyze a two step mechanism, during which LPP is synthesized as intermediate product.

The ability of a polypeptide to catalyze the synthesis of a particular diterpene (for example sclareol) and/or of a particular diterpene diphosphate ester (for example LPP) can be simply confirmed by performing the enzyme assay as detailed in Example 3.

According to the present invention, polypeptides are also meant to include truncated polypeptides provided that they keep their diterpene synthase activity as defined in any of the above embodiments and that they share at least the defined percentage of identity with the corresponding fragment of SEQ ID NO:1 or 2 or of SEQ ID NO:3. Particularly useful truncated polypeptides are those with an N-terminal deletion of the plastid targeting signal.

The percentage of identity between two peptidic or nucleotidic sequences is a function of the number of amino acids or nucleic acids residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs on the world wide web. Preferably, the BLAST program (Tatiana et al, FEMS Microbiol Lett., 174:247-250, 1999) set to the default parameters, available online from the National Center for Biotechnology Information (NCBI), can be used to obtain an optimal alignment of peptidic or nucleotidic sequences and to calculate the percentage of sequence identity.

One object of the present invention is therefore a method for producing sclareol comprising
a) contacting GGPP with at least one polypeptide having a LPP synthase activity and comprising an amino acid sequence at least 50% identical to SEQ ID NO:1 or 2;
b) contacting the intermediate product produced in step a) with at least one polypeptide having a sclareol synthase activity and comprising an amino acid sequence at least 50% identical to SEQ ID NO:3; and
c) optionally, isolating the sclareol produced in step b).

According to a preferred embodiment, steps a) and b) of the method of producing sclareol are carried out simultaneously by contacting GGPP with said at least one polypeptide having a LPP synthase activity and with said at least one polypeptide having a sclareol synthase activity altogether.

For the purpose of the present application, by saying that steps a) and b) are carried out simultaneously, we mean that only one action is necessary for the person who wants to carry out the invention to achieve the result of both steps, i.e. contacting GGPP with at least two polypeptides or with at least one fusion polypeptide, as described below. Nevertheless, the production of sclareol will still take place in a two step mechanism, as illustrated by FIG. 2. LPP is first synthesized in situ form GGPP by the LPP synthase or by the part of the fusion polypeptide having the sequence of the LPP synthase in the presence of the sclareol synthase. The so produced LPP is thus directly contacted with the sclareol synthase or with the part of the fusion polypeptide having the sequence of the sclareol synthase, said enzyme catalyzing the transformation of this precursor to sclareol as soon as it is produced.

According to a preferred embodiment, steps a) and b) of the method of producing sclareol are carried out simultaneously by contacting GGPP with at least one fusion polypeptide capable of catalyzing the transformation of GGPP to sclareol and comprising an amino acid sequence at least 50% identical to SEQ ID NO:1 or 2 and an amino acid sequence at least 50% identical to SEQ ID NO:3.

According to a preferred embodiment, the fusion polypeptide capable of catalyzing the transformation of GGPP to sclareol comprises the sequence of a polypeptide having a LPP synthase activity and an amino acid sequence at least 50% identical to SEQ ID NO:1 or 2 and the sequence of a polypeptide having a sclareol synthase activity and an amino acid sequence at least 50% identical to SEQ ID NO:3.

The method can be carried out in vitro as well as in vivo, as will be explained in details further on.

The polypeptide to be contacted with LPP in vitro can be obtained by extraction from any organism expressing it, using standard protein or enzyme extraction technologies. If the host organism is a unicellular organism or cell releasing the polypeptide of the invention into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptide having a sclareol synthase activity and/or the polypeptide having a LPP synthase activity, either in an isolated form or together with other proteins, for example in a crude protein extract obtained from cultured cells or microorganisms, may then be suspended in a buffer solution at optimal pH. If adequate, salts, BSA, DTT and other kinds of enzymatic co-factors, may be added in order to optimize enzyme activity. Appropriate conditions are described in more details in the Examples further on.

The precursor GGPP or LPP may then be added to the suspension or solution, which is then incubated at optimal temperature, for example between 15 and 40° C., preferably between 25 and 35° C., more preferably at 30° C. After incubation, the LPP or the sclareol produced may be isolated from the incubated solution by standard isolation procedures, such as solvent extraction and distillation, optionally after removal of polypeptides from the solution.

According to another preferred embodiment, the method for producing sclareol is carried out in vivo. In this case, step a) and b) of the above-described method are carried out simultaneously and comprise cultivating a non-human host organism or cell capable of producing GGPP and transformed to express at least one polypeptide comprising an amino acid sequence at least 50% identical to SEQ ID NO:1 or 2 and having a LPP synthase activity and at least one polypeptide comprising an amino acid sequence at least 50% identical to SEQ ID NO:3 and having a sclareol synthase activity under conditions conducive to the production of sclareol.

According to a more preferred embodiment, the method further comprises, prior to step a) and b), transforming a non human organism or cell capable of producing GGPP with at least one nucleic acid encoding a polypeptide comprising an amino acid sequence at least 50% identical to SEQ ID NO:1 or 2 and having a LPP synthase activity and with at least one nucleic acid encoding a polypeptide comprising an amino acid sequence at least 50% identical to SEQ ID NO:3 and having a sclareol synthase activity, so that said organism expresses said polypeptides.

These embodiments of the invention are particularly advantageous since it is possible to carry out the method in vivo without previously isolating the polypeptide. The reaction occurs directly within the organism or cell transformed to express said polypeptide.

The non-human host organism or cell can be transformed with both nucleic acids at the same time or separately. When the non-human host organism or cell is transformed with both nucleic acids at the same time, these nucleic acids may be incorporated in a single or in different vectors.

According to a particular embodiment of the invention, the at least one nucleic acid encoding the LPP synthase comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:4, 5 or the complement thereof. According to a more preferred embodiment, said nucleic acid comprises the nucleotide sequence SEQ ID NO:4, 5 or the complement thereof. In an even more preferred embodiment, said nucleic acid consists of SEQ ID NO:4, 5 or the complement thereof According to a particular embodiment of the invention, the at least one nucleic acid encoding the sclareol synthase comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:6 or the complement thereof. According to a more preferred embodiment, said nucleic acid comprises the nucleotide sequence SEQ ID NO:6 or the complement thereof. In an even more preferred embodiment, said nucleic acid consists of SEQ ID NO:6 or the complement thereof.

In another particular embodiment of the invention, the non-human host organism or cell can also be transformed with at least one nucleic acid encoding a fusion polypeptide capable of catalyzing the transformation of GGPP to sclareol and comprising an amino acid sequence at least 50% identical to SEQ ID NO:1 or 2 and an amino acid sequence at least 50% identical to SEQ ID NO:3.

According to a preferred embodiment, the nucleic acid encoding a fusion polypeptide comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:4, 5 or the complement thereof. According to a more preferred embodiment, said nucleic acid comprises the nucleotide sequence SEQ ID NO:4, 5 or the complement thereof.

According to another preferred embodiment, the nucleic acid encoding a fusion polypeptide comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:6 or the complement thereof. According to a more preferred embodiment, said nucleic acid comprises the nucleotide sequence SEQ ID NO:6 or the complement thereof.

According to an even more preferred embodiment, the nucleic acid encoding the fusion polypeptide consists of SEQ ID NO:4, 5 or the complement thereof and of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:6 or the complement thereof. Alternatively, the nucleic acid encoding the fusion polypeptide consists of SEQ ID NO:6 or the complement thereof and of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:4, 5 or the complement thereof. Alternatively, the nucleic acid encoding the fusion polypeptide consists of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:4, 5 or the complement thereof and of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:6 or the complement thereof. In a most preferred embodiment, the nucleic acid encoding the fusion polypeptide consists of SEQ ID NO:4, 5 or the complement thereof and of SEQ ID NO:6 or the complement thereof.

According to a another preferred embodiment, the nucleic acid encoding the fusion polypeptide comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% identical, even more preferably at least 98% identical to SEQ ID NO:87. According to an even more preferred embodiment, the nucleic acid encoding the fusion polypeptide comprises the nucleotide sequence SEQ ID NO:87. According to a most preferred embodiment, the nucleic acid encoding the fusion polypeptide consists of SEQ ID NO:87

The non-human organism or cell can advantageously be further transformed with at least one gene encoding a polypeptide involved in the metabolism of production of GGPP, such as for example enzymes of the MEP pathway, of the MVA pathway and/or prenyl transferases. Transforming a non-human organism or cell capable of producing GGPP with a LPP synthase and a sclareol synthase, or with a fusion polypeptide, as described in any of the embodiments of the invention, is sufficient for the production of sclareol. Nevertheless, further transformation with at least one enzyme involved in the production of GGPP and/or of one precursor of GGPP, i.e. isopentenyl diphosphate (IPP) and dimethylallyl diphosphate (DMAPP), has the advantage of increasing the amount of precursor available for conversion to sclareol.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects of the present invention and in the Examples.

A particular organism or cell is meant to be "capable of producing GGPP" when it produces GGPP naturally or when it does not produce GGPP naturally but is transformed to produce GGPP, either prior to the transformation with a nucleic acid as described herein or together with said nucleic acid. Organisms or cells transformed to produce a higher amount of GGPP than the naturally occurring organism or cell are also encompassed by the "organisms or cells capable of producing GGPP". Methods to transform organisms, for example microorganisms, so that they produce GGPP are already known in the art. Such methods can for example be found in Huang, Roessner, Croteau and Scott, Engineering *Escherichia coli* for the synthesis of taxadiene, a key intermediate in the biosynthesis of taxol, Bioorg Med Chem., 9(9), 2001, 2237-2242.

According to a preferred embodiment, the organism accumulates GGPP naturally or is transformed to accumulate this precursor.

To carry out the invention in vivo, the host organism or cell is cultivated under conditions conducive to the production of sclareol. Accordingly, if the host is a transgenic plant, optimal growth conditions are provided, such as optimal light, water and nutrient conditions, for example. If the host is a unicellular organism, conditions conducive to the production of sclareol may comprise addition of suitable cofactors to the culture medium of the host. In addition, a culture medium may be selected, so as to maximize sclareol synthesis. Optimal culture conditions are described in a more detailed manner in the following Examples.

Non-human host organisms suitable to carry out the method of the invention in vivo may be any non-human multicellular or unicellular organisms. In a preferred embodiment, the non-human host organism used to carry out the invention in vivo is a plant, a prokaryote or a fungus. Any plant, prokaryote or fungus can be used. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism used to carry out the method of the invention in vivo is a microorganism. Any microorganism can be used but according to an even more preferred embodiment said microorganism is a bacteria or fungus. Preferably said fungus is yeast. Most preferably, said bacteria is *E. coli* and said yeast is *Saccharomyces cerevisiae*.

Several of these organisms do not produce GGPP naturally. To be suitable to carry out the method of the invention, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of the invention in vivo. Suitable eukaryotic cells may be any non-human cell, but are preferably plant cells.

According to a preferred embodiment, the at least one polypeptide having a LPP synthase activity used in any of the above-described embodiments or encoded by the nucleic acid used in any of the above-described embodiments comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 2. According to a more preferred embodiment, said polypeptide comprises the amino acid sequence SEQ ID NO:1 or 2. In an even more preferred embodiment, said polypeptide consists of SEQ ID NO:1 or 2.

According to another preferred embodiment, the at least one polypeptide having a sclareol synthase activity used in any of the above-described embodiments or encoded by the nucleic acid used in any of the above-described embodiments comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:3. According to a more preferred embodiment, said polypeptide comprises the amino acid sequence SEQ ID NO:3. In an even more preferred embodiment, said polypeptide consists of SEQ ID NO:3.

According to a further preferred embodiment, the fusion polypeptide used in any of the above-described embodiments or encoded by the nucleic acid of any of the above-described embodiments comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 2. According to a more preferred embodiment, said fusion polypeptide comprises the amino acid sequence SEQ ID NO:1 or 2.

According to another preferred embodiment, the fusion polypeptide used in any of the above-described embodiments or encoded by the nucleic acid of any of the above-described embodiments comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:3. According to a more preferred embodiment, said fusion polypeptide comprises the amino acid sequence SEQ ID NO:3.

According to an even more preferred embodiment, the fusion polypeptide used in any of the above-described embodiments or encoded by the nucleic acid of any of the above-described embodiments consists of SEQ ID NO:1 or 2 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:3. Alternatively, it consists of SEQ ID NO:3 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 2. Alternatively, the fusion polypeptide consists of an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 2 and of an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:3. In a most preferred embodiment, the fusion polypeptide consists of SEQ ID NO:1 or 2 and of SEQ ID NO:3.

According to another particularly preferred embodiment, the fusion polypeptide used in any of the above-described embodiments or encoded by the nucleic acid of any of the above-described embodiments comprises an amino acid sequence at least 50%, preferably at least 55%, preferably at least 60%, preferably at least 65%, preferably at least 70%, preferably at least 75%, preferably at least 80%, preferably at least 85%, more preferably at least 90%, even more preferably at least 95%, most preferably at least 98% identical to SEQ ID NO:88. According to a more preferred embodiment, the fusion polypeptide comprises the amino acid sequence SEQ ID NO:88. According to an even more preferred embodiment, the fusion polypeptide consists of SEQ ID NO:88.

According to a further specific embodiment of the invention, the polypeptide having a LPP synthase activity as intended in any embodiment of the method of the invention is a polypeptide comprising an amino acid sequence at least 50% identical to any of SEQ ID NO:36 to 39, which are truncated forms of SEQ ID NO:1. Preferably said polypeptides comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and most preferably at least 98% identical to any of SEQ ID NO:36 to 39. According to a more preferred embodiment, said polypeptide comprises any of SEQ ID NO:36 to 39. According to an even more preferred embodiment, said polypeptide consists of any of SEQ ID NO:36 to 39.

According to another specific embodiment of the invention, the polypeptide having a sclareol synthase activity as intended in any embodiment of the method of the invention is a polypeptide comprising an amino acid sequence at least 50% identical to SEQ ID NO:74, which is a truncated form of SEQ ID NO:3. Preferably said polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and most preferably at least 98% identical to SEQ ID NO:74. According to a more preferred embodiment, said polypeptide comprises SEQ ID NO:74. According to an even more preferred embodiment, said polypeptide consists of SEQ ID NO:74.

According to another specific embodiment, the fusion polypeptide used in any of the above-described embodiments or encoded by the nucleic acid of any of the above-described embodiments comprises an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:36 to 39. In an even more preferred embodiment, it comprises any of SEQ ID NO:36 to 39.

According to another specific embodiment, the fusion polypeptide used in any of the above-described embodiments or encoded by the nucleic acid of any of the above-described embodiments comprises an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:74. In an even more preferred embodiment, it comprises SEQ ID NO:74.

In an even more preferred embodiment, the fusion polypeptide used in any of the above-described embodiments or encoded by the nucleic acid of any of the above-described embodiments consists of any of SEQ ID NO:36 to 39 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:74. Alternatively, the fusion polypeptide used in any of the above-described embodiments or encoded by the nucleic acid of any of the above-described embodiments consists of SEQ ID NO:74 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:36 to 39. Alternatively, the fusion polypeptide consists of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:36 to 39 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:77. In a most preferred embodiment, the fusion polypeptide used in any of the above-described embodiments or encoded by the nucleic acid of any of the above-described embodiments consists of any of SEQ ID NO:36 to 39 and of SEQ ID NO:74.

According to a further embodiment, the nucleic acid encoding a LPP synthase used in any of the above-described embodiments comprises a nucleotide sequence at least 50% identical to any of SEQ ID NO:28 to 31, which are truncated forms of SEQ ID NO:4, or to the complement thereof. Preferably said nucleic acid comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and most preferably at least 98% identical to any of SEQ ID NO:28 to 31 or the complement thereof. According to a more preferred embodiment, said nucleic acid comprises any of SEQ ID NO:28 to 31 or the complement thereof. According to an even more preferred embodiment, said nucleic acid consists of any of SEQ ID NO:28 to 31 or the complement thereof.

According to another specific embodiment of the invention, the nucleic acid encoding a sclareol synthase used in any of the above-described embodiment comprises a nucleotide sequence at least 50% identical to SEQ ID NO:73, which is a truncated form of SEQ ID NO:6, or to the complement thereof. Preferably said nucleic acid comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and most preferably at least 98% identical to SEQ ID NO:73 or the complement thereof. According to a more preferred embodiment, said nucleic acid comprises SEQ ID NO:73 or the complement thereof. According to an even more preferred embodiment, said nucleic acid consists of SEQ ID NO:73 or the complement thereof.

According to another specific embodiment, the nucleic acid encoding a fusion polypeptide as used in any of the above-described embodiments comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:28 to 31 or the complement thereof. In an even more preferred embodiment, it comprises the nucleotide sequence of any of SEQ ID NO:28 to 31 or the complement thereof.

According to another specific embodiment, the nucleic acid encoding a fusion polypeptide as used in any of the above-described embodiments comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:73 or the complement thereof. In an even more preferred embodiment, it comprises the nucleotide sequence of SEQ ID NO:73 or the complement thereof.

In an even more preferred embodiment, the nucleic acid encoding a fusion polypeptide as used in any of the above-described embodiments consists of any of SEQ ID NO:28 to 31 or the complement thereof and of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:73 or the complement thereof. Alternatively, nucleic acid encoding the fusion polypeptide as used in any of the above-described embodiments consists of SEQ ID NO:73 or the complement thereof and of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:28 to 31 or the complement thereof. Alternatively, the nucleic acid encoding the fusion polypeptide consists of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:28 to 31 or the complement thereof and of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:73 or the complement thereof. In a most preferred embodiment, the nucleic acid encoding the fusion polypeptide as used in any of the above-described embodiments consists of any of SEQ ID NO:28 to 31 or the complement thereof and of SEQ ID NO:73 or the complement thereof.

According to another preferred embodiment, the polypeptide or the nucleic acid used in the method of any of the embodiments above is derived from *Salvia sclarea*.

An important tool to carry out the method of the invention is the fusion polypeptide itself. A fusion polypeptide capable of catalyzing the transformation of GGPP to sclareol and comprising an amino acid sequence at least 50% identical to SEQ ID NO:1 or 2 and an amino acid sequence at least 50% identical to SEQ ID NO:3 is therefore another object of the present invention.

According to a preferred embodiment, the fusion polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 2. According to a more preferred embodiment, the fusion polypeptide comprises the amino acid sequence SEQ ID NO:1 or 2.

According to another preferred embodiment, the fusion polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:3. According to a more preferred embodiment, said fusion polypeptide comprises the amino acid sequence SEQ ID NO:3.

In an even more preferred embodiment, the fusion polypeptide consists of SEQ ID NO:1 or 2 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:3. Alternatively, the fusion polypeptide consists of SEQ ID NO:3 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 2. In a most preferred embodiment, the fusion polypeptide consists of SEQ ID NO:1 or 2 and of SEQ ID NO:3.

According to a particular embodiment of the invention, the fusion polypeptide comprises the sequence of a truncated form of SEQ ID NO:1, such as SEQ ID NO:36 to 39, and/or the sequence of a truncated form of SEQ ID NO:3, such as SEQ ID NO:74.

Therefore, according to a particular embodiment of the invention the fusion polypeptide comprises an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:36 to 39. In an even more preferred embodiment, it comprises any of SEQ ID NO:36 to 39.

According to another specific embodiment, the fusion polypeptide comprises an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:74. In an even more preferred embodiment, it comprises SEQ ID NO:74.

In an even more preferred embodiment, the fusion polypeptide consists of any of SEQ ID NO:36 to 39 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:74. Alternatively, the fusion polypeptide consists of SEQ ID NO:74 and of an amino acid sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:36 to 39. In a most preferred embodiment, the fusion polypeptide consists of any of SEQ ID NO:36 to 39 and of SEQ ID NO:74.

According to another particularly preferred embodiment, the fusion polypeptide of the invention comprises an amino acid sequence at least 50%, preferably at least 55%, preferably at least 60%, preferably at least 65%, preferably at least 70%, preferably at least 75%, preferably at least 80%, preferably at least 85%, more preferably at least 90%, even more preferably at least 95%, most preferably at least 98% identical to SEQ ID NO:88. According to a more preferred embodiment, the fusion polypeptide comprises the amino acid sequence SEQ ID NO:88. According to an even more preferred embodiment, the fusion polypeptide consists of SEQ ID NO:88.

As used herein, the polypeptide is intended as a polypeptide or peptide fragment that encompasses the amino acid sequences identified herein, as well as truncated or variant polypeptides, provided that they keep their activity as defined above and that they share at least the defined percentage of identity with the corresponding fragment of SEQ ID NO:1, 2 or 3.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

As mentioned above, the nucleic acid encoding the fusion polypeptide of the invention is a useful tool to modify non-human host organisms or cells intended to be used when the method is carried out in vivo.

A nucleic acid encoding a fusion polypeptide according to any of the above-described embodiments is therefore also an object of the present invention.

According to a preferred embodiment, the nucleic acid comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:4, 5 or the complement thereof. According to a more preferred embodiment, the nucleic acid comprises the nucleotide sequence SEQ ID NO:4, 5 or the complement thereof.

According to another preferred embodiment, the nucleic acid comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:6 or the complement thereof. According to a more preferred embodiment, said fusion polypeptide comprises the amino acid sequence SEQ ID NO:6 or the complement thereof.

In an even more preferred embodiment, the nucleic acid consists of SEQ ID NO:4, 5 or the complement thereof and of a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:6 or the complement thereof. Alternatively, the nucleic acid consists of SEQ ID NO:6 or the complement thereof and of a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:4, 5 or the complement thereof. Alternatively, the nucleic acid consists of a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:4, 5 or the complement thereof and of a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:6 or the complement thereof. In a most preferred embodiment, the nucleic acid consists of SEQ ID NO:4, 5 or the complement thereof and of SEQ ID NO:6 or the complement thereof.

Particularly useful nucleic acid are those that encode fusion polypeptides comprising truncated forms of SEQ ID NO:1 and/or 3. Therefore nucleic acid comprising a truncated form of SEQ ID NO:4, such as SEQ ID NO:28 to 31, or the complement thereof and/or comprising a truncated form of SEQ ID NO:6, such as SEQ ID NO:73, or the complement thereof are particularly useful embodiments of the invention.

Therefore, according to another specific embodiment, the nucleic acid comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:28 to 31 or the complement thereof. In an even more preferred embodiment, it comprises the nucleotide sequence of any of SEQ ID NO:28 to 31 or the complement thereof.

According to another specific embodiment, the nucleic acid comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:73 or the complement thereof. In an even more preferred embodiment, it comprises the nucleotide sequence of SEQ ID NO:73 or the complement thereof.

In an even more preferred embodiment, the nucleic acid consists of any of SEQ ID NO:28 to 31 or the complement thereof and of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:73 or the complement thereof. Alternatively, nucleic acid consists of SEQ ID NO:73 or the complement thereof and of a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:28 to 31 or the complement thereof. In a most preferred embodiment, the nucleic acid consists of any of SEQ ID NO:28 to 31 or the complement thereof and of SEQ ID NO:73 or the complement thereof.

According to another particularly preferred embodiment, the nucleic acid comprises a nucleotide sequence at least 50%, preferably at least 55%, preferably at least 60%, preferably at least 65%, preferably at least 70%, preferably at least 75%, preferably at least 80%, preferably at least 85%, more preferably at least 90%, even more preferably at least 95%, most preferably at least 98% identical to SEQ ID NO:87. According to a more preferred embodiment, the nucleic acid comprises the nucleotide sequence SEQ ID NO:87. According to an even more preferred embodiment, the nucleic acid consists of SEQ ID NO:87.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above.

The nucleic acids comprising a sequence obtained by mutation of SEQ ID NO:4, 5 or of the complement thereof and/or a sequence obtained by mutation of SEQ ID NO:6 or of the complement thereof are also encompassed by the invention, provided that that the sequences they comprise share at least the defined percentage of identity with the corresponding fragments of SEQ ID NO:4, 5 or 6 or with the complement thereof and provided that they encode a fusion polypeptide capable of catalyzing the transformation of GGPP to sclareol as defined above. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention.

Another important tool for transforming host organisms or cells suitable to carry out the method of the invention in vivo is an expression vector comprising a nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for producing or making polypeptides having a sclareol synthase activity, as disclosed further below.

Recombinant non-human host organisms and cells transformed to harbor at least one nucleic acid encoding a polypeptide having a LPP synthase activity and comprising an amino acid sequence at least 50% identical to SEQ ID NO:1 or 2 and at least one nucleic acid encoding a polypeptide having a sclareol synthase activity and comprising an amino acid sequence at least 50% identical to SEQ ID NO:3, so that it heterologously expresses or over-expresses said polypeptides are also very useful tools to carry out the method of the invention. Such non-human host organisms and cells are therefore another object of the present invention.

According to a preferred embodiment, said polypeptide having a LPP synthase activity comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1 or 2. According to a more preferred embodiment, said polypeptide comprises SEQ ID NO:1 or 2. According to an even more preferred embodiment said polypeptide consists of SEQ ID NO:1 or 2.

According to another preferred embodiment, said polypeptide having a sclareol synthase activity comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:3. According to a more preferred embodiment, said polypeptide comprises SEQ ID NO:3. According to an even more preferred embodiment said polypeptide consists of SEQ ID NO:3.

According to a further preferred embodiment, said nucleic acid encoding a polypeptide having a LPP synthase activity comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:4, 5 or the complement thereof. According to a more preferred embodiment, said nucleic acid comprises SEQ ID NO:4, 5 or the complement thereof. According to an even more preferred embodiment said nucleic acid consists of SEQ ID NO:4, 5 or the complement thereof.

According to a further preferred embodiment, said nucleic acid encoding a polypeptide having a sclareol synthase activity comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:6 or the complement thereof. According to a more preferred embodiment, said nucleic acid comprises SEQ ID NO:6 or the complement thereof. According to an even more preferred embodiment said nucleic acid consists of SEQ ID NO:6 or the complement thereof.

According to another preferred embodiment, said polypeptide having a LPP synthase activity comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:36 to 39. According to a more preferred embodiment, said polypeptide comprises any of SEQ ID NO:36 to 39. According to an even more preferred embodiment said polypeptide consists of any of SEQ ID NO:36 to 39.

According to another preferred embodiment, said polypeptide having a sclareol synthase activity comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:73. According to a more preferred embodiment, said polypeptide comprises SEQ ID NO:73. According to an even more preferred embodiment said polypeptide consists of SEQ ID NO:73.

According to a further preferred embodiment, said nucleic acid encoding a polypeptide having a LPP synthase activity comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to any of SEQ ID NO:28 to 31 or the complement thereof. According to a more preferred embodiment, said nucleic acid comprises any of SEQ ID NO:28 to 31 or the complement thereof. According to an even more preferred embodiment said nucleic acid consists of any of SEQ ID NO:28 to 31 or the complement thereof.

According to a further preferred embodiment, said nucleic acid encoding a polypeptide having a sclareol synthase activity comprises a nucleotide sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:73 or the complement thereof. According to a more preferred embodiment, said nucleic acid comprises SEQ ID NO:73 or the complement thereof. According to an even more preferred embodiment said nucleic acid consists of SEQ ID NO:73 or the complement thereof.

According to another preferred embodiment, the non-human host organisms and cells are transformed to harbor at least one nucleic acid encoding a fusion polypeptide, as described in any of the above embodiments of the invention, so that it heterologously expresses or over-expresses said fusion polypeptide.

The non-human organism or cell can advantageously be further transformed with at least one gene encoding a polypeptide involved in the metabolism of production of GGPP, such as for example enzymes of the MEP pathway, of the MVA pathway and/or prenyl transferases. Transforming a non-human organism or cell capable of producing GGPP with a LPP synthase and a sclareol synthase, or with a fusion polypeptide, as described in any of the embodiments of the invention, is sufficient for the production of sclareol. Nevertheless, further transformation with at least one enzyme involved in the production of GGPP and/or of one precursor of GGPP, i.e. isopentenyl diphosphate (IPP) and dimethylallyl diphosphate (DMAPP), has the advantage of increasing the amount of precursor available for conversion to sclareol.

Non-human host organisms of the invention may be any non-human multicellular or unicellular organisms. In a preferred embodiment, the non-human host organism is a plant, a prokaryote or a fungus. Any plant, prokaryote or fungus is suitable to be transformed according to the present invention. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism is a microorganism. Any microorganism is suitable for the present invention, but according to an even more preferred embodiment said microorganism is a bacteria or fungus. Preferably, said fungus is yeast. Most preferably, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Preferred higher eukaryotic cells are plant cells.

The term "transformed" refers to the fact that the host was subjected to genetic engineering to comprise one, two or more copies of each of the nucleic acids required in any of the above-described embodiment. Preferably the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., Cloning Vectors: A Laboratory Manual, 1985, Elsevier, New York and Sambrook et al., Molecular Cloning: A Laboratory Manual, $2^{nd}$ edition, 1989, Cold Spring Harbor Laboratory Press. Cloning and expression vectors for higher plants and/or plant cells in particular are available to the skilled person. See for example Schardl et al. Gene 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, agrobacterium-mediated transformation, polyethylene-glycol-mediated transformation, particle bombardement, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

In order to carry out the method for producing sclareol in vitro, as exposed herein above, it is very advantageous to provide a method of making at least one fusion polypeptide having a diterpene synthase activity as described in any embodiment of the invention. Therefore, the invention provides a method for producing at least one fusion polypeptide capable of catalyzing the transformation of GGPP to sclareol comprising a) culturing a non-human host organism or cell transformed with the expression vector of the invention, so that it harbors a nucleic acid according to the invention and expresses or over-expresses a polypeptide encoded by said nucleic acid and capable of catalyzing the transformation of GGPP to sclareol;

b) isolating the polypeptide capable of catalyzing the transformation of GGPP to sclareol from the non-human host organism or cell cultured in step a).

According to a preferred embodiment, said method further comprises, prior to step a), transforming a non-human host organism or cell with at least one expression vector of the invention, so that it harbors at least one nucleic acid according to the invention and expresses or over-expresses the polypeptide encoded by said nucleic acid.

Transforming and culturing of the non-human host organism or cell can be carried out as described above for the method of producing sclareol in vivo. Step b) may be performed using any technique well known in the art to isolate a particular polypeptide from an organism or cell.

A "polypeptide variant" as referred to herein means a fusion polypeptide capable of catalyzing the transformation of GGPP to sclareol and being substantially homologous to the polypeptide according to any of the above embodiments, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physicochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, Biochemistry, Addison-Wesley Pub. Co., (1983). The effects of such substitutions can be calculated using substitution score matrices such a PAM-120, PAM-200, and PAM-250 as discussed in Altschul, (J. Mol. Biol. 219:555-65, 1991). Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or site directed mutant may be made by any method known in the art. Variants and derivatives of native polypeptides can be obtained by isolating naturally-occurring variants, or the nucleotide sequence of variants, of other or same plant lines or species, or by artificially programming mutations of nucleotide sequences coding for the fusion polypeptides of the invention. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides.

Therefore, in an embodiment, the present invention provides a method for preparing a variant fusion polypeptide capable of catalyzing the transformation of GGPP to sclareol and comprising the steps of:

(a) selecting a nucleic acid according to any of the embodiments exposed above;

(b) modifying the selected nucleic acid to obtain at least one mutant nucleic acid;

(c) transforming host cells or unicellular organisms with the mutant nucleic acid sequence to express a polypeptide encoded by the mutant nucleic acid sequence;

(d) screening the polypeptide for at least one modified property; and, (e) optionally, if the polypeptide has no desired variant sclareol synthase activity, repeat the process steps (a) to (d) until a polypeptide with a desired variant sclareol synthase activity is obtained;

(f) optionally, if a polypeptide having a desired variant sclareol synthase activity was identified in step d), isolating the corresponding mutant nucleic acid obtained in step (c).

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution. Proc Natl Acad Sci USA., 1994, 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, the fusion polypeptide comprising SEQ ID NO:4 or 5 and SEQ ID NO:6 may be recombined with any other diterpene synthase encoding nucleic acids, for example isolated from an organism other than Salvia sclarea. Thus, mutant nucleic acids may be obtained and separated, which may be used for transforming a host cell according to standard procedures, for example such as disclosed in the present Examples.

In step (d), the polypeptide obtained in step (c) is screened for at least one modified property, for example a desired modified enzymatic activity. Examples of desired enzymatic activities, for which an expressed polypeptide may be screened, include enhanced or reduced enzymatic activity, as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present Examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

All the publications mentioned in this application are incorporated by reference to disclose and describe the methods and/or materials in connection with which the publications are cited.

DESCRIPTION OF THE DRAWINGS

FIG. 7: (A) N-terminal sequences of the full-length and truncated SsLPPs3 recombinant diterpene synthases (SEQ ID NO:1 and SEQ ID NO:36 to 39). (B) SDS-PAGE analysis of the full-length and truncated versions of the SsLPPs3 diterpene synthases expressed in *E. coli*. Lane M, molecular weight standard; lane 1, crude soluble protein extract from control cells; lane 2, crude soluble protein extract from cells transformed with pET28-SsLPPs3; lane 3, purified histidine tagged-SsLPPs3; lane 4 and 5: respectively 1 and 0.5 μL of crude soluble protein extract from cells transformed with pETDuet-SsLPPs3; lanes 5 to 9, 0.5 μL of crude soluble protein extract from cells transformed with pETDuet containing the four sequential deletions. The gel was stained for total protein using Coomassie blue.

FIG. 9: Alignment of the amino acid sequences from the 1132 constructs (SEQ ID NO:3 and 74) for heterologous expression in *E coli*.

FIG. 13: Structure of the plasmids used for the transformation of *E. coli* cells in Examples 10 and 11.

SPECIFIC EMBODIMENTS OF THE INVENTION OR EXAMPLES

Figure 1:
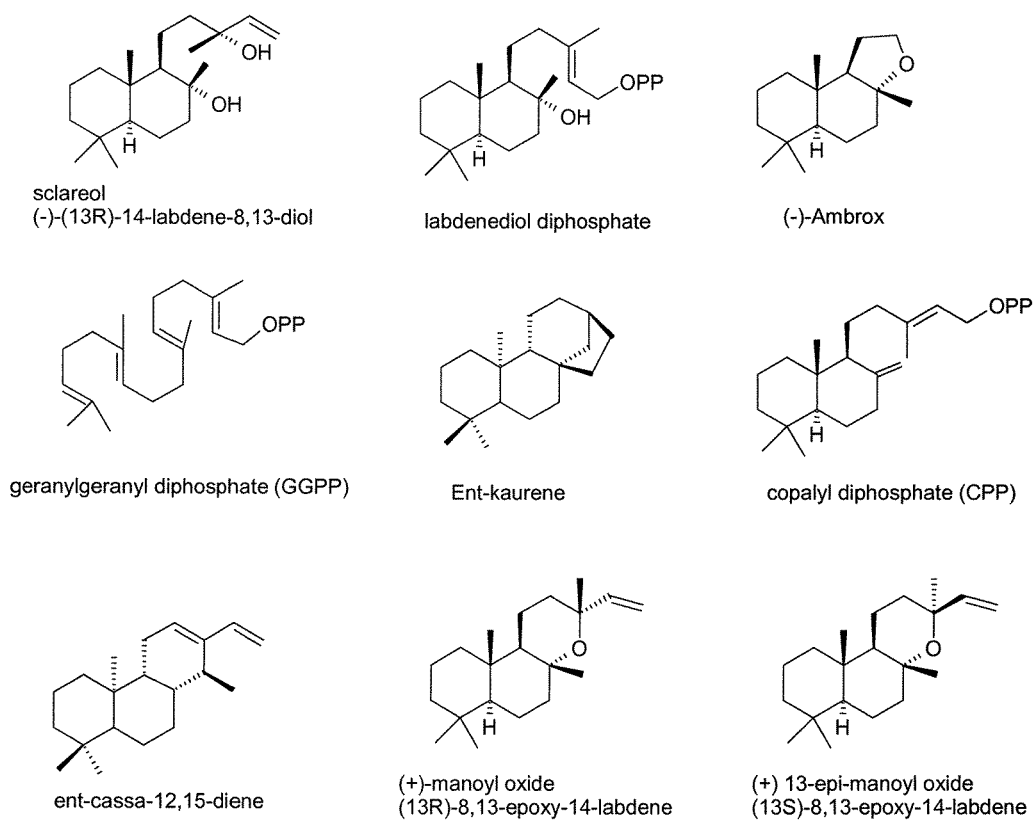
FIG. 1: Structures of the diverse compounds cited in the description.
Figure 2:
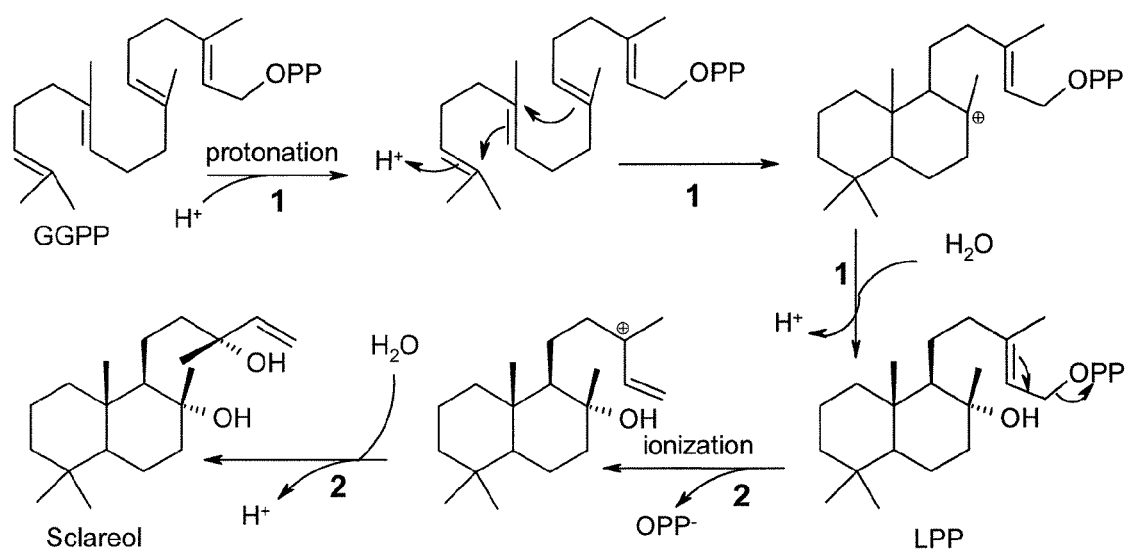
FIG. 2: Mechanism of the biosynthesis of sclareol from GGPP. The enzymatic steps 1 and 2 can be catalyzed by two distinct proteins (a LPP synthase and a sclareol synthase) or by a single bi-functional enzyme (fusion polypeptide).

The invention will now be described in further detail by way of the following Examples.

Example 1

Isolation of LPP Synthase Encoding cDNAs from *Salvia clarea* by a PCR Approach

A. Plant Material and RNA Extraction.

*Salvia sclarea* developing flower buds (1.5 to 2 cm length, 1-2 days old) were collected in fields of Bassins (Switzerland) and directly frozen in liquid nitrogen. Total RNA was extracted using the Concert™ Plant RNA Reagent from Invitrogen (Carlsbad, Calif.) and the mRNA was purified by oligodT-cellulose affinity chromatography using the FastTrack® 2.0 mRNA isolation Kit (Invitrogen, Carlsbad, Calif.) according to the manufacturer's instructions. A cDNA library was constructed using the Marathon™ cDNA Amplification Kit (Clontech, Mountain View, Calif.).

B. Polymerase Chain Reactions for Amplification of Diterpene Synthases cDNAs

Amino acid sequences of class I and II diterpene synthases from different plants were aligned and conserved motifs were selected. Degenerate oligonucleotides sequences were deduced from these conserved amino acid motifs. The Motif DxDDTAM (x being any amino acid), found in the central part of diterpene synthases amino acid sequences and postulated to be involved in the interaction with the diphosphate moiety of GGPP in class II diterpene synthases, was used to design the forward primer DT3F (5'-(SEQ ID NO:7)).

Another motif, DVW(I/L)GK(T/S), found in some diterpene synthases, was used to design the reverse primer DT4R (SEQ ID NO:8)).

PCR were performed using these primers in all possible combinations of reverse and forward primers. The PCR mixture contained 0.4 μM of each primer, 300 μM each dNTPs, 5 μL of 10× HotStartTaq® DNA polymerase buffer (Qiagen), 2 μL of 100 fold diluted cDNA, 0.5 μL of HotStartTaq® DNA polymerase in a final volume of 50 μL. The cycling conditions were: 35 cycles of 45 sec at 94° C., 45 sec at 50° C. and 2 min at 72° C.; and 10 min at 72° C. The sizes of the PCR products were evaluated on a 1% agarose gel. The bands corresponding to the expected size were excised from the gel, purified using the QIAquick® Gel Extraction Kit (Qiagen) and cloned in the pCR®2.1-TOPO vector using the TOPO TA cloning Kit (Invitrogen, Carlsbad, Calif.). Inserted cDNA fragments were then subjected to DNA sequencing and the sequence was compared against the GenBank non-redundant protein database (NCBI) using the BLASTX algorithm (Altschul et al, *J. Mol. Biol.* 215, 403-410, 1990). From the different PCR performed, only the combination of primers DT3F (SEQ ID NO:7) and DT4R (SEQ ID NO:8) gave a DNA fragment with the expected size and with sequence homology to diterpene synthases. All fragments issued from this amplification had the exact same sequence. This 354 bp sequence was named FN23 (SEQ ID NO:9).

C. Full Length cDNA Isolation by Rapid Amplification of cDNA Ends (RACE).

Oligonucleotides specific for the FN23 sequence (SEQ ID NO:9) were designed: FN23-F1' (SEQ ID NO:10)), FN23-F2 (SEQ ID NO:11)) and FN23-F3 (SEQ ID NO:12)). These primers were used in RT-PCR in combination with oligodT primers extended with an adaptor sequence (SEQ ID NO:13). The composition of the RT-PCR reaction mixture was the following: 10 μl 5× Qiagen OneStep RT-PCR buffer, 400 μM each dNTP, 400 nM each primer, 2 μl Qiagen OneStep RT-PCR Enzyme Mix, 1 μl RNasin® Ribonuclease Inhibitor (Promega Co., Madisson, Wis.) and 1250 ng total RNA in a final volume of 50 ml. The thermal cycler conditions were: 30 min at 50° C. (reverse transcription); 15 min at 95° C. (DNA polymerase activation); 35 cycles of 45 sec at 94° C., 45 sec at 50° C. and 90 sec at 72° C.; and 10 min at 72° C. A second round of PCR was performed using the RT-PCR products as template with the adapterP primer (SEQ ID NO:14) in combination with the same or nested FN23-specific primers. This PCR approach provided a 1271 bp cDNA fragment (FN30 (SEQ ID NO:15)) having a 192 bp perfect overlap with the FN23 fragment (SEQ ID NO:9) and containing the 3'end including the stop codon and the 3' non-coding sequence of the corresponding cDNA.

For amplification of the 5' end of the cDNA, anti-sense oligonucleotides specific for FN23 (SEQ ID NO:9) were designed: FN23-R1 (SEQ ID NO:16)), FN23-R2 (SEQ ID NO:17)), FN23-R3 (SEQ ID NO:18)). These primers were used for 5'RACE using the *S. sclarea* cDNA library following the Marathon™ cDNA Amplification Kit protocol (Clontech, Mountain View, Calif.). The thermal cycling conditions were as follows: 1 min at 94° C., 5 cycles of 30 sec at 94° C. and 4 min at 72° C., 5 cycles of 30 sec at 94° C. and 4 min at 70° C., 20 cycles of 30 sec at 94° C. and 4 min at 68° C. This 5'RACE provided a 1449 bp cDNA fragment (FN40 (SEQ ID NO:19) having a 227 bp perfect overlap with FN23 (SEQ ID NO:9). Comparison with known diterpene synthase sequences revealed that the FN40 fragment (SEQ ID NO:19) contained the translation initiation codon and a 87 bp non-coding region. The assembling of the three cDNA fragments (FN23, FN30 and FN40 (SEQ ID NO:9, 15 and 19) provided a full length cDNA sequence (SaTps1) of 2655 bp with an open reading frame of 2355 bp (SEQ ID NO:20) coding for a 785 residues protein (SEQ ID NO:21) having strong homology with diterpene synthases and namely with copalyl diphosphate synthases. The DxDD motif, involved in protonation initiated cyclization, was present in the amino acid sequence (position 372) and the DDxD motif, involved in ionization initiated cyclization, was not found. Thus this protein sequence has the typical characteristics of a class II diterpene synthase catalyzing exclusively protonation-dependent cyclizations of GGPP. The heterologous expression and enzymatic characterization of this protein are detailed in the following Examples 2-4.

Example 2

Heterologous Expression of the *S. sclarea* LPP Synthase in *E. coli*

The pETDuet-1 (Novagen, Madison, Wis.), designed for expression under the control of a T7 promoter, was used for expression in *E. coli* cells. To construct the expression plasmid, the open reading frame of SaTps1 (SEQ ID NO:20) was amplified by PCR from the cDNA library with the forward and reverse primers SaTps-Nde (SEQ ID NO:22)) and SaTps-Kpn (SEQ ID NO:23)) designed to introduce an NdeI site immediately before the start codon and a KpnI site after the stop codon. Since the open reading frame contains an NdeI site at position of 1614 of the open reading frame, this amplification was performed in two steps by overlap extension PCR (Horton et al, Gene 78, 61-68, 1989), using the primers SaTps-Nde (SEQ ID NO:22) and SaTps-Kpn (SEQ ID NO:23) in combination with the primers Satps-mut1f (SEQ ID NO:24)) and Satps-mut1r (SEQ ID NO:25)), designed to remove the NdeI site without altering the amino acid sequence. The resulting cDNA were first ligated in the PCR2.1-Topo plasmid using the TOPO TA Cloning Kit (Invitrogen, Carlsbad, Calif.) and the sequences of the inserts were verified prior to sub-cloning as NdeI-KpnI fragment into the pETDuet-1 vector.

Analysis of the sequence of several clones obtained by amplification from the cDNA library with the SaTps1 specific primers showed some variability in several positions of the cDNA sequence. Seven positions were identified, in which two different amino acids can be found. One position was found were insertion of a serine residue occurred in some of the clones. These positions are listed in the table below.

| Positions (relative to the aminoacid sequence) | Amino acid |
| --- | --- |
| 34 | Ile or Thr |
| 40 | Phe or Leu |
| 174 | Gln or His |
| 222 | Gly or Asp |
| 538 | Gln or His |
| 560 | Arg or Leu |
| 596 | Asn or Lys |
| 612 | Insertion of a Ser |

Figure 3:
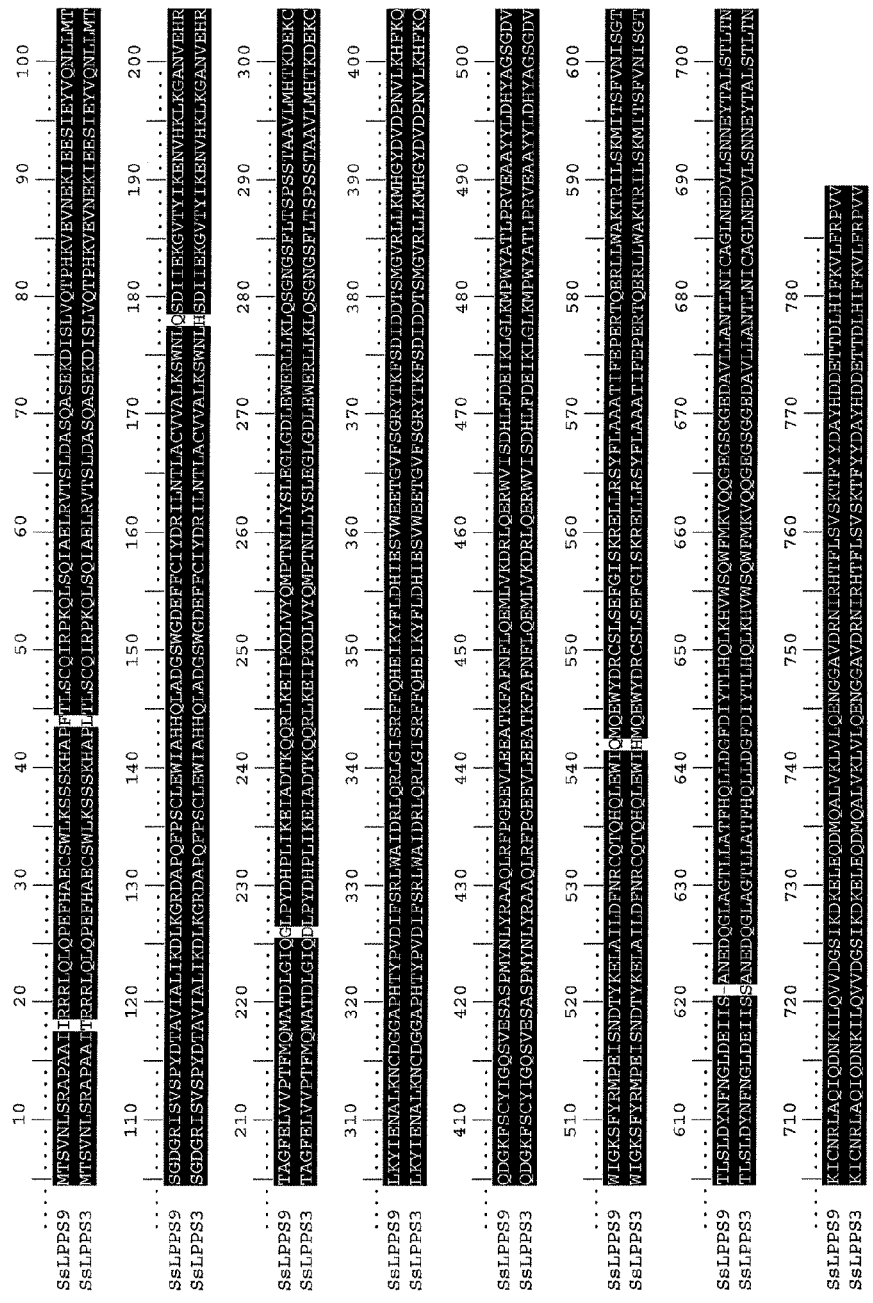
FIG. 3: Alignment of the amino acid sequences SEQ ID NO:1 and 2 deduced from SsLPPs3 (SEQ ID NO:4) and SsLPPs9 (SEQ ID NO:5), two closely related diterpene synthases encoding cDNAs, isolated for the purpose of the present invention. Identical residues are in white letters and residues differing between the two sequences are in black letters.

These variations seemed to occur in a random manner in eleven different clones sequenced, suggesting that at least two very closely related isoforms of a diterpene synthase are present in the *S. sclarea* genome and that the PCR amplification approach leaded to shuffling of the sequences. Two clones, SsLPPs3 (SEQ ID NO:4) and SsLPPs9 (SEQ ID NO:5) representative of the sequences variability (FIG. 3), were selected for the heterologous expression and enzyme characterization experiments.

The plasmids pETDuet-SsLPPs3 and pETDuet-SsLPPs9 were transferred into B121(DE3) *E. Coli* cells (Novagen, Madison, Wis.). Single colonies of transformed cells were used to inoculate 5 ml LB medium. After 5 to 6 hours incubation at 37° C., the cultures were transferred to a 20° C. incubator and left 1 hour for equilibration. Expression of the protein was then induced by the addition of 1 mM IPTG and the culture was incubated over-night at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g), and the supernatants containing the soluble proteins were used for further experiments.

Figure 4:
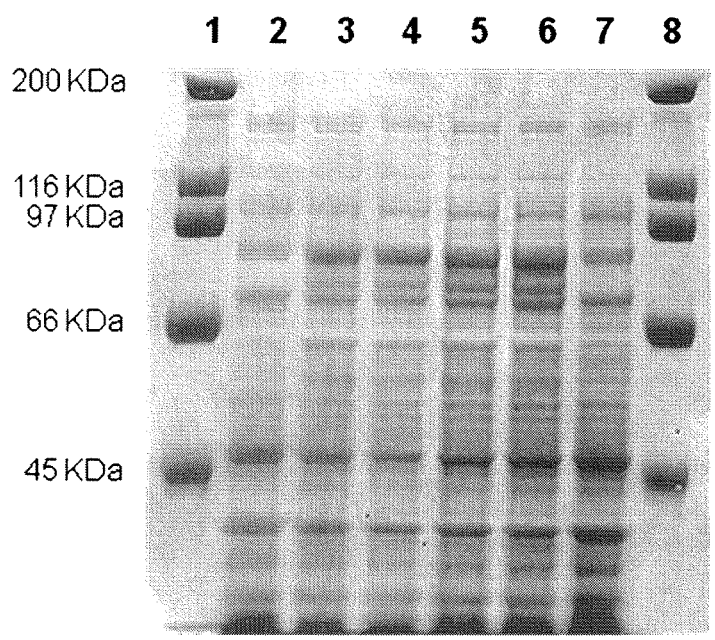
FIG. 4: SDS-PAGE analysis of the crude soluble protein extracts from *E. coli* cells expressing the SsLPPs3 and SsLPPs9 proteins (SEQ ID NO:1 and 2). Lanes 1 and 8: molecular weight standards; lanes 2 and 7: control proteins obtained from cells transformed with the plasmid without insert; lanes 3 and 4: proteins from cells transformed with pETDue-SsLPPs3; lanes 5 and 6 proteins from cells transformed with pETDuet-SsLPPs9. The gel was stained for total protein using Coomassie blue.

The crude protein extracts from pETDuet-SsLPPs3 and pETDuet-SsLPPs9 transformed cells were analyzed by SDS-PAGE and compared to protein extracts obtained from cells transformed with the empty pETDuet plasmid. The recombinant SsLPPs3 and SsLPPs9 proteins (SEQ ID NO:1 and 2) were clearly detected and the apparent molecular weight estimated at 90 KDa, a value in concordance with the calculated molecular weight of 83 KDa (FIG. 4).

Example 3

Purification of the *S. sclarea* LPP Synthase and Enzymatic Activities

To further characterize the recombinant diterpene synthases, we undertook to purify the SsLPPs3 and SsLPPs9 enzymes (SEQ ID NO:1 and 2).

Figure 5:
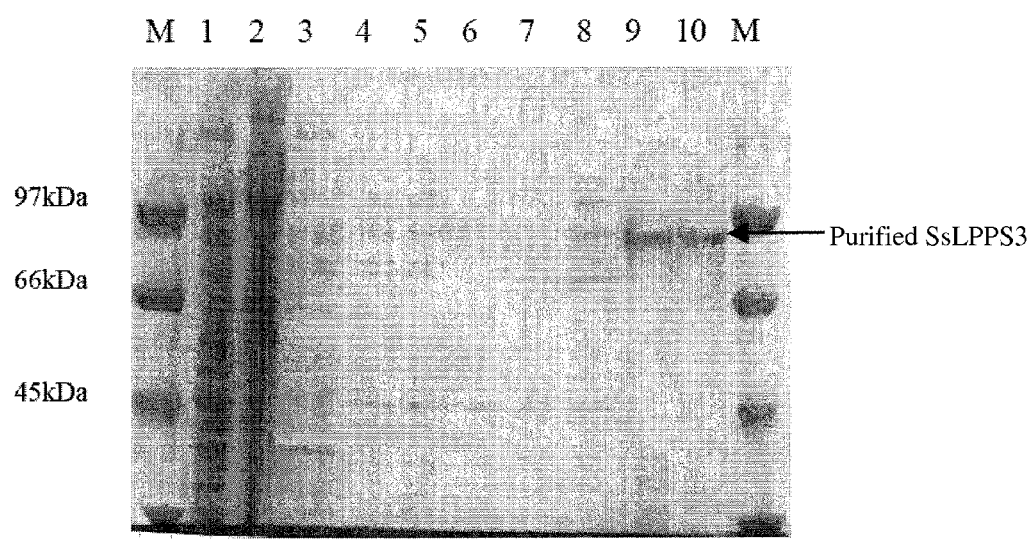
FIG. 5: SDS-PAGE analysis of the affinity purified recombinant sage diterpene synthase SsLPPs3 (SEQ ID NO:1) expressed in *E. coli*. Lane M, molecular weight standard; lane 1, crude soluble protein extract from control cells; lane 2, crude soluble protein extract from cells transformed with pET28-SsLPPs3; lane 3, flow-through fractions; lanes 4 to 7, washing fractions; lanes 8 to 10, elution fractions with 250 mM L-histidine. The gel was stained for total protein using Coomassie blue.

The PCR2.1-Topo plasmids containing the SsLPPs3 and SsLPPs9 cDNA (SEQ ID NO:4 and 5) (Example 2) were digested with NdeI and SacI and the inserts were ligated into the pET28a(+) plasmid (Novagen). The resulting expression plasmids (pET28-SsLPPs3 and pET28-SsLPPs9) contain the cDNAs with a 5'-end modification (SEQ ID NO:26 and 27) designed to express the proteins with an N-terminal hexahistidine tag. Purification was performed under native conditions using the ProBond™ Purification System (Invitrogen) following the manufacturer protocol excepted that, for the elution, imidazole was replaced by L-histidine to minimize inhibition of the enzyme. Using this approach, the SsLPPs3 and SsLPPs9 recombinant enzymes could be purified to apparent homogeneity (FIG. 5).

Figure 6:
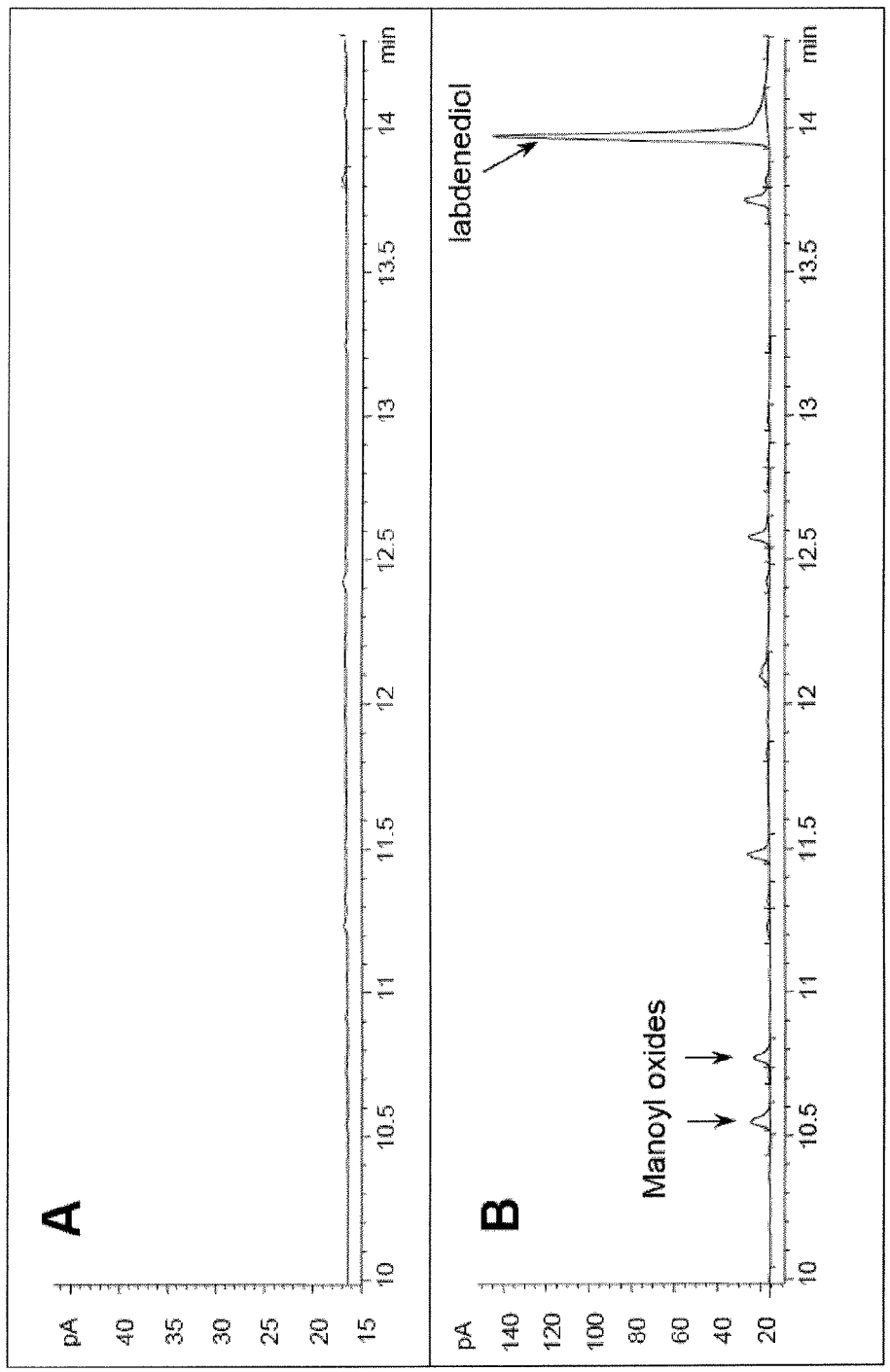
FIG. 6: GC analysis of the products obtained after incubation of the affinity purified SsLPPs3 (SEQ ID NO:1) with GGPP. (A) direct solvent extract; (B) Solvent extract of the same sample after alkaline phosphatase treatment.

The affinity purified enzymes were incubated 12 hours at 30° C. with 200 μM GGPP and 1 mM DTT in MOPSO pH 7, 10% glycerol. No diterpene product was observed by extracting the incubation with pentane and analysis of the extract by GC or GC-MS. Treatment of the same extract by alkaline phosphatase (Sigma, 6 units/ml), followed by extraction with pentane and GC analysis, showed the formation of labdenediol (FIG. 6) and demonstrated the enzymatic formation of labdenediol-diphosphate (LPP) as unique product from GGPP by the recombinant diterpene synthase.

The GC analysis was performed on an 6890 Series GC system (Agilent Technologies) equipped with a flame ionization detector using a 0.25 mm inner diameter by 30 m SPB-1 capillary column (Supelco, Bellefonte, Pa.). The carrier gas was He at a constant flow of 1 mL/minute. The initial oven temperature was 100° C. (1 minute hold) followed by a gradient of 10° C./minute to 300° C.

The GC-MS analysis was performed on a 6890 Series GC system (Agilent) coupled to 5975 mass detector (Agilent Technologies). The column was equipped with a 0.25 mm inner diameter by 30 m length DB-1MS column (Agilent Technologies). The carrier gas was He at a constant flow of 1 mL/minute. The initial oven temperature was 80° C. followed by a gradient of 10° C./minute to 280° C. The spectra were recorded at 70 eV with an electron multiplier voltage of 2200V. The identity of product was confirmed by concordance of the retention times and matching of the mass spectrum with the spectrum of authentic standards.

Example 4

N-Terminal Deletions of the *Salvia sclarea* LPP Synthase

In plants, diterpene synthases are located in the plastids. This compartmentalization is controlled by a transport mechanism that recognizes an N-terminal transit peptide signal. Thus, diterpene synthases are generally expressed as pre-proteins and are processed in the plastids by cleavage of the peptide signal resulting in a mature protein. Analysis of the N-terminal sequence of SsLPPs3 and SsLPPs9 (SEQ ID NO:1 and 2), using the ChloroP method (Emanuelsson et al, *Protein Science* 8, 978-984, 1999), did not reveal any clear evidence for the presence of a transit peptide. Experiments were thus performed to evaluate the effect of N-terminal deletions on the enzymatic activity. Four truncated cDNA were made for SsLPPs3 resulting in deletion of 17, 37, 53 and 63 amino acids respectively (SEQ ID NO:28 to 31). Each construct was made by PCR using four different forward primers each designed to anneal at the position of the one of desired truncation and introducing an NdeI restriction site followed by a ATG translation initiation codon (SsLPPs3_del1, (SEQ ID NO:32); SsLPPs3_del2, (SEQ ID NO:33); SsLPPs3_del3, (SEQ ID NO:34), SsLPPs3_del4, (SEQ ID NO:35). These primers were used in combination with the primer SaTps-Kpn (SEQ ID NO:23) (Example 2) and the four cDNAs obtained (SEQ ID NO:28 to 31) were ligated in the pETDuet-1 plasmid. Heterolgous expression of the proteins (SEQ ID NO:36 to 39) was performed in *E coli* as described in Example 2. FIG. 7 shows an SDS-PAGE analysis comparing the level of production of the heterologous proteins obtained with the different full-length and truncated constructs. An improved expression level was clearly observed specially for the two largest deletions. These results are typical for plastid-localized terpene synthases and reflect an improved solubility and/or stability of the mature protein compared to the pre-protein.

Example 5

Massively Parallel Sequencing of a *S. sclarea* Flower cDNA Library

We used the technology of massive parallel sequencing of small DNA fragments developed by Illumina (San Diego, Calif.) to obtain sequence information of all the transcripts (transcriptome) present in the *Salvia sclarea* flowers. This sequencing technique uses a reversible terminator-based sequencing chemistry and the Cluster Station and Genome Sequencer apparatuses developed by Solexa and Illumina.

The technology and equipment was set up at Fasteris SA (Geneva, Switzerland) and the preparation of the DNA samples and the sequencing were performed by Fasteris SA. An aliquot (1 µg) of the cDNA library generated from *S. sclarea* developping flowers and using the Marathon™ cDNA Amplification Kit (Clontech, Mountain View, Calif.) (Example 1), was treated using the Genomic Sample Prep Kit (Illumina). Briefly, the DNA is fragmented by nebulization, the ends are repaired to generate blunt ends, adapters are ligated to the ends of the DNA fragments and the adapter-modified DNA fragments are amplified by PCR. After controlling the quality of the library by gel electrophoresis, the generation of the DNA clusters on the flow cell and the sequencing reaction is performed on the Cluster Station and Genome Sequencer equipments. Using this technology, 1.9 millions of short sequences (reads) of 35 bases were obtained.

The Edena software (Hernandez et al, *Genome res.* 15(5), 802-809, 2008) was used to reassemble contiguous sequences. The five last bases were first removed from each read because of possible miss-incorporations due to the lower fidelity in the last cycles of the sequencing procedure. The parameters of the software were set such as to allow 15 bases minimum length for the overlaps with strict (100%) identity. The contigs (contiguous sequences) with a length of at least 50 bases were retained. In these conditions, 2054 contigs of 50 to 1330 bases in length could be reconstituted.

To evaluate the quality of the assembling, the contigs were searched for sequence identity with the DNA sequence of SsLPPs3, the class II diterpene synthases first isolated from the *S. sclarea* cDNA library (SEQ ID NO:4, Example 2). This search was performed using the BLASTn method (Altschul et al, *J. Mol. Biol.* 215, 403-410, 1990). Surprisingly, only 3 contigs of lengths of 81, 73 and 52 bases (contigs 1 to 3, SEQ ID NO: 40 to 42) were found and only forty reads had been used by the Eland software to generate these contigs. Alignment with the SsLPPs3 reference sequence showed that the 3 contigs covered only 8.7% of the full-length sequence although with an identity of 99%.

Very limited sequence information has been reported in the public databases for *Salvia sclarea*. The only gene sequence available from the NCBI database was the sequence of the large subunit of the ribulose-1,5-bisphosphate carboxylase (RuBisCO) from salvia sclarea (NCBI access No. Z37450). Search of the contigs for DNA identity with this S. sclarea RuBisCO DNA sequence (BLASTn Search) provided two contigs of 870 and 547 bases respectively (contigs 4 and 5, SEQ ID NO:43 and 44). Alignment of the two contigs with the RuBisCO sequence showed coverage of 98%: only 27 bases (between position 858 and 884) out of 1420 bases were not present in the contigs. In addition to this almost complete coverage, the identity between the reference sequence and the contigs was 99.5%, representing a difference of only 7 nucleotides.

All reads (non-assembled data) were then searched for sequence identity with the SsLPPs3 sequence (SEQ ID NO:4). The Eland software (Illumina) was used to perform this search allowing a maximum of 2 mismatches with the reference sequence. A total of 616 reads where recovered. Alignment of the selected fragments with the reference sequence revealed that the SsLPPs3 sequence was covered on the whole length with a slightly higher coverage (more reads) towards the 3'end. The same manipulation with the RuBisCO sequence showed that 1650 reads were obtained for this sequence. The coverage of the reference sequence with the reads was much higher for the RuBisCo than for SsLPPs3. For SsLPPs3 (SEQ ID NO:4), several small regions with no coverage and regions with sequence ambiguity between reads were found. This incomplete coverage prevents the complete re-assembling and is certainly the reason for the generation of only a few very small contigs.

Example 6

Extraction of Class I Diterpene Synthases-Like Sequences from the Sequencing Data The Blast algorithm (Altschul et al, *J. Mol. Biol.* 215, 403-410, 1990) was used to search for homology of the deduced amino acid sequences with class I diterpene synthase sequences.

A Blastx search against a protein database was first performed with the 2054 contigs. This search provided only one contig (contig1610, SEQ ID NO:45) presenting sequence homology with class I diterpene synthases. The amino acid sequence deduced from this contig contained the DDxxD motif characteristic of ionization-initiated cyclization of prenyl-diphosphates.

A fraction of the row data, representing approximately $3 \times 10^5$ reads was then searched for homology with class I diterpene synthases. The reads were searched using the tBlastn algorithm with five selected type I diterpene synthase amino acid sequences (NCBI accession numbers AAC39443, BAB19275, BAB12441, AAD34295, AAS98912). This search selected 462 reads, which were then processes using the CAP program (Huang, Genomics 14(1), 18-25, 1992) to identify overlapping sequences. A small portion of the reads could be assembled in short contigs of maximum length of 111 bases. These contigs as well as the remaining isolated reads were used for Blastx search against a protein database to confirm their identity with class I diterpene synthases. Finally, 5 DNA fragments were retained (SEQ ID NO: 46 to 50).

Figure 8:
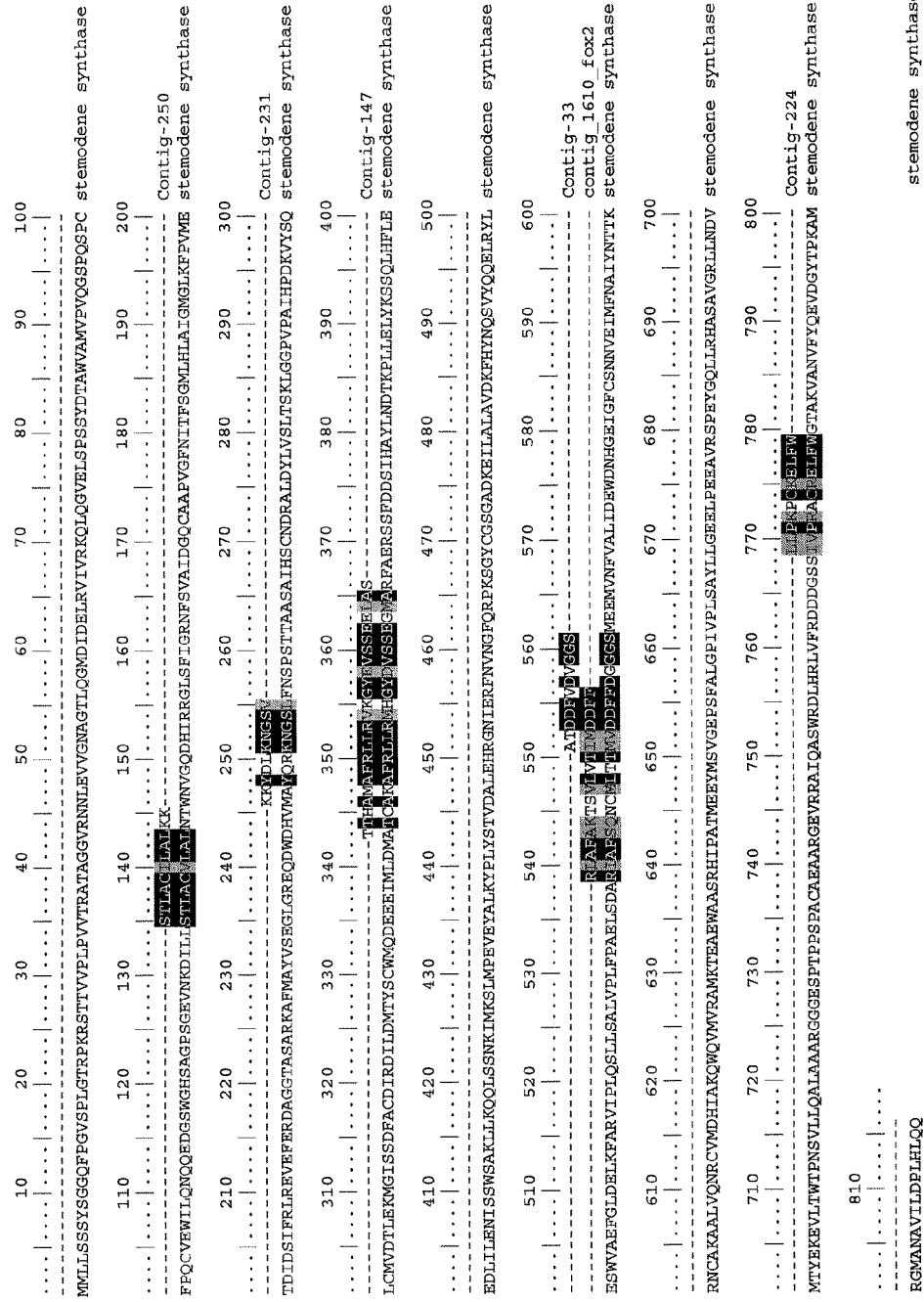
FIG. 8: Alignment of amino acid sequences from the class II diterpene synthase-like fragments with the sequence of the stemodene synthase from *Oriza sativa* (Access. No. AAZ76733).

The amino acid sequences (SEQ ID NO:51 to 55) were deduced from the selected fragments and were aligned with reference diterpene synthase sequences, allowing their relative positioning. FIG. 8 shows an alignment of these sequences with the full-length sequence of the stemodene synthase from *Oriza sativa* (Marrone et al, 2006; NCBI access No. AAZ76733), taken as reference.

Example 7

PCR Amplification of Full-Length Class I Diterpene Synthases cDNAs

A set of forward and reverse oligonucleotides was deduced from the diterpene synthase-related DNA sequences selected from the sequencing of the *S. sclarea* cDNA library (Example 6). These primers were used in combination with cDNA adaptor primers in 3'/5'RACE type PCR amplifications. The amplifications were performed using the *S. sclarea* cDNA library, prepared as described above in Example 1, following the Marathon™ cDNA Amplification Kit protocol (Clontech, Mountain View, Calif.). The thermal cycling conditions were as follows: 1 min at 94° C., 5 cycles of 30 sec at 94° C. and 4 min at 72° C., 5 cycles of 30 sec at 94° C. and 4 min at 70° C., 20 cycles of 30 sec at 94° C. and 4 min at 68° C.

Using the Cont250-Fwd primer (SEQ ID NO:56) a 547 bp DNA sequence (1130Cont250, SEQ ID NO:66) was obtained. Analysis of the sequence revealed that it corresponded to the 5'end of a diterpene synthase cDNA and contained 348 bp of the coding region. With the primer Cont147_fw1 (SEQ ID NO:57) and Cont147_fw2 (SEQ ID NO:58) we obtained a 1473 bp sequence (1132Cont147, SEQ ID NO:67) containing the 3'end and 1293 bp of the coding region of a diterpene synthase cDNA. The Cont147_rev1 (SEQ ID NO:59) and Cont147_rev2 (SEQ ID NO:60) primers allowed the amplification of a 464 bp DNA fragment (1134Cont147, SEQ ID NO:68). The deduced amino acid showed homology with diterpene synthases but alignment with other diterpene synthases sequences suggested that 200 to 300 codons where still missing to reach the 5'end. All the sequences obtained by this series of amplification differed significantly from the sequences of SsLPPs previously isolated (SsLPPs3 and SsLPPs9, SEQ ID NO:4 and 5).

A 5'RACE approach was used to identify the 5'end of the ORF corresponding to the 1132Cont147 sequence (SEQ ID NO:67). Using the primers 1132_race1 (SEQ ID NO:62) and 1132_race2 (SEQ ID NO:63), a 536 bp sequence (1132RACE, SEQ ID NO:69) was obtained which had 41 bases overlap with the 1132Cont147 fragment (SEQ ID NO:67). The N-term of this RACE product was identical to the previously obtained 1134Cont147 sequence (SEQ ID NO:68) and thus no extension at the 5'end was observed. As observed previously, this sequence had homology with diterpene synthases but seemed shorter by at least 200 codons than all other published diterpene synthases sequences. 5'RACE experiments were performed, in order to try to extend the sequence toward the 5'end of the 1132Cont147 (SEQ ID NO:67) sequence and to identify the true translation initiation codon. Several sets of oligonucleotides were designed but no additional sequence information was obtained. This led us to suppose that one of the ATG codons in the 1134Cont147 sequence (SEQ ID NO:68) was actually the initiation codon of the corresponding diterpene synthase gene. The sequence of this putative diterpene synthase (named SsTps1132, SEQ ID NO:6)) was reconstituted from the 1132Cont147 (SEQ ID NO:67) and 1132RACE (SEQ ID NO:69) sequences. Taking the first ATG, the 1728 bp ORF of SsTps1132 (SEQ ID NO:6) encoded for a 575 amino acid protein (SEQ ID NO:3). This protein contained the ionization-dependent motif (DDFFD) and shared homology, but relatively low, with published diterpene synthases; the closest sequence being a terpene synthase from *Nicotiana tabacum* (NCBI access No. AAS98912), with 37% identity. This protein also shared only 23% identity with the SsLPPs isolated from *S. Sclarea* in Examples 1 to 4. SsTps1132 has been aligned with selected diterpene synthase sequences. These alignments showed that SsTps1132 (SEQ ID NO:3) is truncated at the N-terminal end by 150 to 240 amino acids compared to the other diterpene synthases.

The ChloroP method (Emanuelsson et al, *Protein Science* 8, 978-984, 1999) was used to predict the presence of a chloroplast transit peptide in SsTps1132 (SEQ ID NO:3). A chloroplast transit peptide of 51 amino acids was predicted, arguing for a chloroplast localization of this protein.

Search of all reads for sequences identical to the SsTps1132 (SEQ ID NO:6) DNA sequence, provided 425 reads. The expression level of SsTps1132 (220 reads/Kb) was similar to the expression level of SsLPPs (SEQ ID NO:4 and 5) (260 reads/Kb). With the assumption that enzymes catalyzing steps in the same metabolic pathway are generally expressed at the similar level, it can be speculated that SsTps1132 is involved in the same metabolic pathway as SsLPPs.

The contigs generated with the Edena software (Example 5) were searched for DNA sequences identical to the sequences of the new putative class I diterpene synthase SsTps1132 (SEQ ID NO:3). Four contigs were found. The previously identified contig1610 (SEQ ID NO:45) and three additional contigs (of length of 53 to 96 bp, SEQ ID NO:70 to 72) not previously identified as fragment of a diterpene synthase. Blastx search with these three sequences did not show homology with known protein sequences. The failure in finding homology for these contigs is due to the short lengths of these fragments and to the low homology of SsTps1132 with the diterpene synthases present in the databases.

Example 8

Heterologous Expression of the *S. Sclarea* Class I Diterpene Synthases in *E Coli*

To assign an enzymatic activity to SsTps1132 (SEQ ID NO:3), the recombinant protein was expressed in *E coli*. The full-length cDNAs was inserted into the pet101/D-TOPO vector using the Champion pET101 Directional TOPO Expression Kit.

Two constructs were prepared: one to express the full-length protein and one to express a truncated protein based on the chloroplast transit peptide prediction. The full-length SsTps1132 (SEQ ID NO:6) open reading frame was amplified from the cDNA library using the primer pair 1132_start_1 (SEQ ID NO:64) and 1132-stop (SEQ ID NO:61). The primers 1132_start2 (SEQ ID NO:65) and 1132_stop (SEQ ID NO:61) were used to prepare the construct for the expression of SsTps1132 (SEQ ID NO:3) with a 50 amino acid N-terminal deletion. All amplifications of cDNA for expression of the expression constructs were performed using the Pfu DNA polymerase (Promega), in a final volume of 50 µl containing 5 µl of Pfu DNA polymerase 10× buffer, 200 µM each dNTP, 0.4 µM each forward and reverse primer, 2.9 units Pfu DNA polymerase and 5 µl of 100-fold diluted cDNA (prepared as described herein in Example 1 using the Marathon™ cDNA Amplification Kit (Clontech)). The thermal cycling conditions were as follows: 1.5 min at 95° C.; 30 cycles of 45 sec at 95° C., 30 sec at 58° C. and 5 min at 72° C.; and 10 min at 72° C.

After the ligation in the pET101 vector, several clones were selected and were sequenced to ensure that no mutation had been introduced during the PCR amplification. Two constructs were selected: SsTps1132 (SEQ ID NO:6) and 1132-2-5 (SEQ ID NO:73). The alignment of the two amino acid sequences deduced from these constructs is shown in FIG. 9.

The plasmids pET101-SsTps1132, and pET101-1132-2-5 were transferred into B121(DE3) *E. Coli* cells (Novagene, Madison, Wis.). Single colonies of transformed cells were used to inoculate 5 ml LB medium. After 5 to 6 hours incubation at 37° C., the cultures were transferred to a 20° C. incubator and left 1 hour for equilibration. Expression of the protein was then induced by the addition of 1 mM IPTG and the culture was incubated over-night at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g), and the supernatants containing the soluble proteins were used for further experiments. The crude protein extracts were analysed by SDS-PAGE and compared to protein extracts obtained from cells transformed with the empty pET101 plasmid. It appeared that the deletion of the peptide signal improved the heterologous expression in *E coli*.

Example 9

Enzymatic Activity of the Recombinant *S. Sclarea* Class I Diterpene Synthases in *E Coli*

The crude *E coli* protein extracts containing the recombinant proteins and prepared as described in Example 8 were used for the characterization of the enzymatic activities. The enzymatic assays were performed as described in Example 3. All assays were performed in 50 mM MOPSO pH 7, 10% glycerol, 1 mM DTT.

Figure 10:
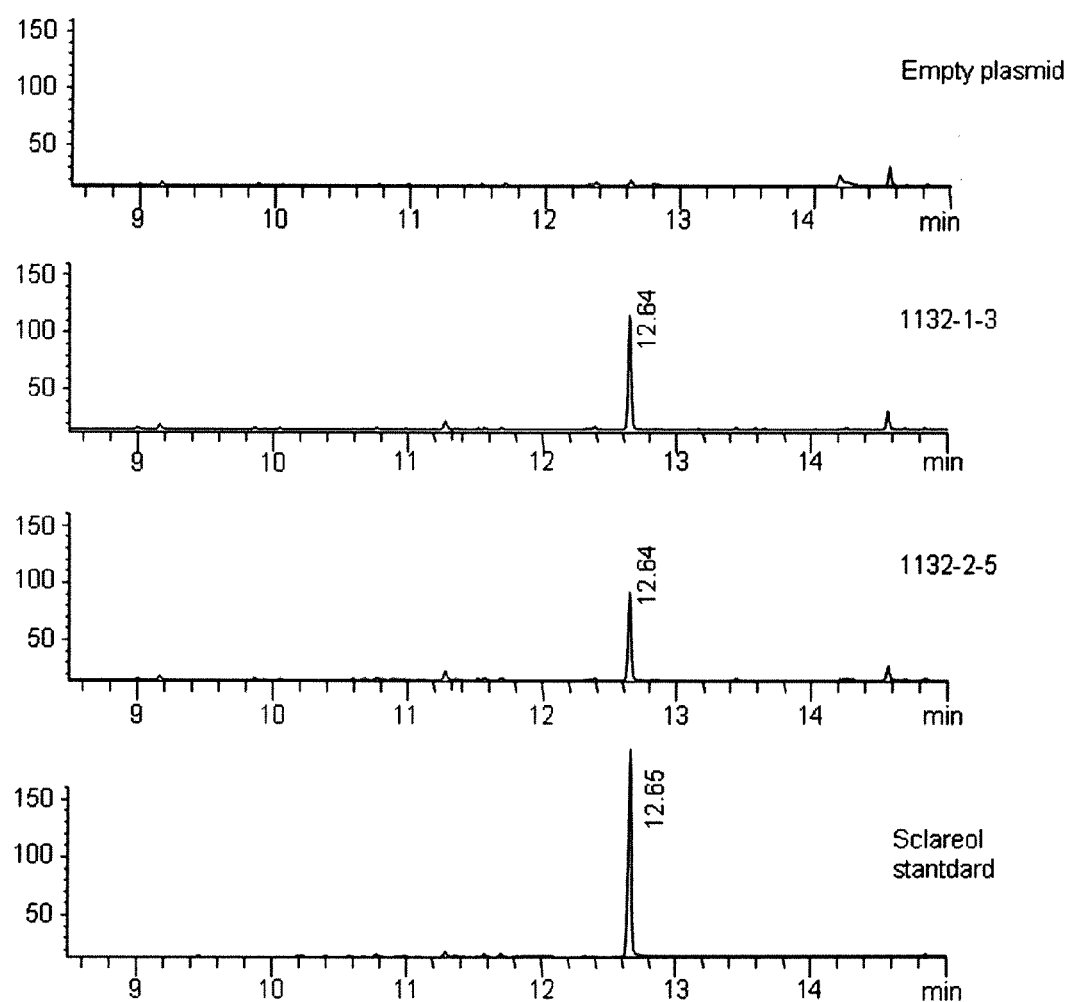
FIG. 10: GC analysis of the products obtained after incubation of the different 1132 recombinant proteins with LPP. Crude protein extracts from *E. coli* expressing the recombinant SsTps1132(1132-1-3, SEQ ID NO:3) and 1132-2-5 (SEQ ID NO:74) proteins were incubated with LPP in a in a final volume of 1 mL 50 mM MOPSO pH 7 supplemented with 15 mM $MgCl_2$.
Figure 11:
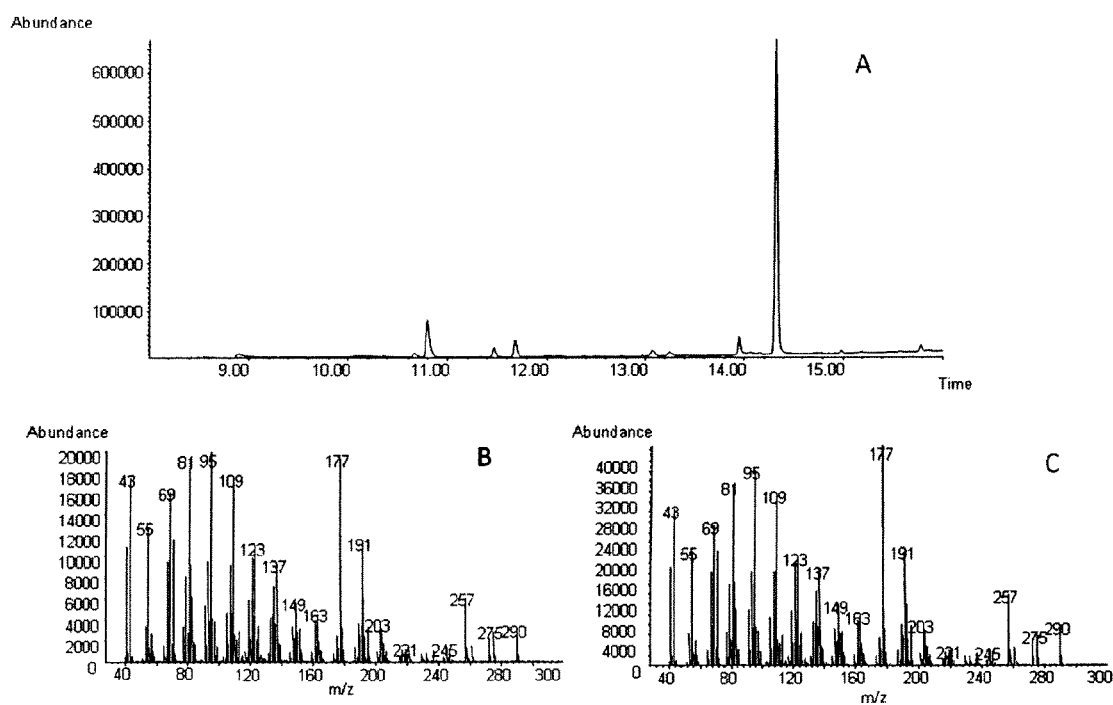
FIG. 11: GC-MS analysis of the products generated from LPP by the recombinant 1132-2-5 protein (SEQ ID NO:74). (A) Total ion chromatogram of the products obtained from the incubation of LPP with a crude protein extract from *E. coli* transformed with pET101-1132-2-5. (B) Mass spectrum of the peak at retention time of 14.3. (C) Mass spectrum of an authentic sclareol standard.

The enzymatic activities were first evaluated using as substrate either GGPP or LLP, the product of SsLPPs and the presumed intermediate in the biosynthesis of sclareol (Examples 1 to 4). GGPP was synthesized as described by Keller and Thompson (*J. Chromatogr* 645(1), 1993, 161-167) and LPP was prepared enzymatically as described in Example 3. The assays were performed in the presence of 10 to 100 µM of substrate, 15 mM $MgCl_2$ and 0.1 to 0.5 mg of crude protein in a total volume of 1 mL. The tubes were incubated 4 to 12 hours at 30° C. and extracted twice with one volume of pentane. After concentration under a nitrogen flux, the extracts were analysed by GC and GC/MS (using the conditions described in Example 3) and compared to extracts from assay with control proteins (obtained from cells transformed with the empty plasmid). With GGPP as substrate, no activity was observed with any of recombinant proteins (data not shown). With LPP as substrate, activity was observed with both SsTps1132 (SEQ ID NO:3) and 1132-2-5 (SEQ ID NO:74) (FIG. 10). The enzymes were also active in the absence of $MgCl_2$ and the same product profiles were observed with an overall activity roughly the same. The identity of product was confirmed by concordance of the retention times (FIG. 10) and matching of the mass spectrum with the spectrum of an authentic standard (FIG. 11). In all assays, a single peak of sclareol was observed with no trace of additional product.

Figure 12:
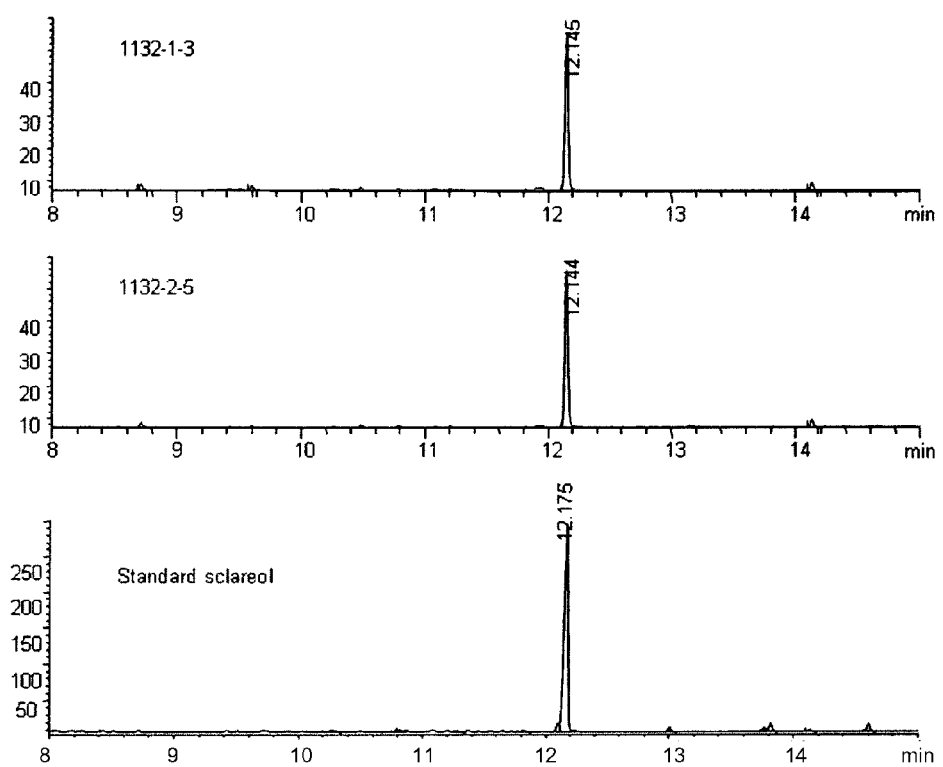
FIG. 12: GC analysis of the products obtained after co-incubation of the 1132 recombinant proteins (SEQ ID NOs:3 and 74) with the SsLPPs3 recombinant protein (SEQ ID NO:1) in the presence of GGPP.

Assays were then performed with co-incubation of the class II diterpene synthase (SsLPPs3, SEQ ID NO:1; Examples 1-4) and the class I diterpene synthases (1132 series, SEQ ID NO:3 and 74). Assays were performed in 50 mM MOPSO pH 7, 10% glycerol, 1 mM DTT, 50 µM GGPP, with 1 mM $MgCl_2$ and in the presence of 50 µL of the crude protein extracts from *E coli* expressing the different constructs. Thus assays in the presence of 50 µL of crude protein extracts containing the SsLPPs3 recombinant enzyme (SEQ ID NO:1) and 50 µL of extracts containing either SsTps1132 (SEQ ID NO:3) or 1132-2-5 (SEQ ID NO:74) recombinant proteins were evaluated for the production of diterpene products. FIG. 12 shows the GC profiles of extracts from such incubations in the presence of $MgCl_2$. Sclareol was produced with both 1132 constructs (SEQ ID NO:3 and 74), a result consistent with the assay described above with LPP as substrate. No significant difference was observed when omitting $MgCl_2$ from the incubations (data not shown).

In conclusion SsTps1132 (SEQ ID NO:6) encodes for the sclareol synthase and catalyses the conversion of LPP to sclareol.

We have thus shown that, in Salvia sclarea, sclareol is synthesized from GGPP in two steps by two distinct enzymes, an LPP synthase and a sclareol synthase. We have isolated cDNAs encoding for each of this two diterpene synthases. The LPP synthase, encoded by the SsLPPs3 and SsLPPs9 cDNAs catalyses the conversion of GGPP to LPP and contains the characteristic features of class II diterpene synthases. The sclareol synthase, encoded by the SsTps1132 cDNA, catalyses the conversion of LPP to sclareol and is related to class I diterpene synthases although with some particularities, i.e a large deletion at the N-terminal end.

Example 10

In-Vivo Production of Sclareol in *E coli* by Coexpression of the Two Diterpene Synthases.

To evaluate the in-vivo production of slareol in *E coli* cells, plasmids and transformed cells are prepared for the co-expression of the two diterpene synthases (the LPP synthase and the sclareol synthase). In addition to the two diterpene synthases, a FPP synthase and a GGPP synthase are also co-expressed to ensure a sufficient pool of GGPP in the cells. To further increase the carbon flux in the pathway and increase the level of GGPP and subsequently the level of sclareol produced, the genes encoding for a partial mevalonate pathway are also expressed in the same cells. These later genes encode for a mevalonate kinase (mvaK1), a phosphomevalonate kinase (mvaK2), a mevalonate diphosphate decarboxylase (MvaD) and a isopentenyl diphosphate isomerase (idi) and convert mevalonate to isopentenyl diphosphate (IPP) and dimethylallyl diphosphate (DMAPP), the two substrates of the FPP synthase.

The yeast FPP synthase gene (Accession number J05091) is amplified from *S. cerevisiae* genomic DNA using the primers FPPy_NcoI (SEQ ID NO:75) and FPPY-Eco (SEQ ID NO:76). The genomic DNA is isolated from *S. cerevisiae* using the Qiagen RNA/DNA Maxi Kit (Qiagen AG, Basel, Switzerland). The PCR is performed with the Pfu DNA polymerase (Promega AG, Dubendorf, Switzerland) in a final volume of 50 µl containing 0.4 µl of each primer, 200 µM dNTPs, 0.5 µl DNA polymerase, 5 µl *S. cerevisiae* genomic DNA. The PCR cycling condition are as follows: 90 sec at 95° C.; 28 cycles of 45 sec at 95° C., 30 sec at 54° C. and 4 min at 72° C.; 10 min at 72° C. The amplified DNA is ligated as NdeI-EcorI fragment in the first multi cloning site (MCS1) of the pACYCDuet-1 plasmid providing the plasmid pACYCDuet-FPPs harbouring the FPPs gene under the control of a T7 promoter.

An operon containing the genes encoding for mvaK1, mvaK2, MvaD and idi is amplified from genomic DNA of *Streptococcus pneumoniae* (ATCC BAA-334, LGC Standards, Molsheim, France) with the primers MVA-up1-start (SEQ ID NO:77) and MVA-up2-stop (SEQ ID NO:78). The PCR is performed using the PfuUltra™ II Fusion HS DNA polymerase (Stratagene), the composition of the PCR mix being according to the manufacturer instructions. The thermal cycling condition are 2 min at 95° C.; 30 cycles of 20 sec at 95° C., 20 sec at 58° C. and 90 sec at 72° C.; and 3 min at 72° C. The 3.8 Kb fragment is purified on an agarose gel and ligated using the In-Fusion™ Dry-Down PCR Cloning Kit (clontech) into the second MCS of the pACYCDuet-FPPs plasmid digested with NdeI and XhoI providing the plasmid pACYCDuet-4506 (FIG. 13A). The sequences of the two inserts are fully sequenced to exclude any mutation.

The CrtE gene from *Pantoea agglomerans* encoding for a GGPP synthase (Accession number M90698) is selected and is synthesized with codon optimization (DNA2.0, Menlo Park, Calif. 94025, USA). The CrtE gene is amplified with the primers CrtE_Nco (SEQ ID NO:79) and CrtE_Bam (SEQ ID NO:80) in order to introduce the NcoI and BamHI restriction sites at the 5'-end and 3'-end respectively. The PCR is performed with the Pfu DNA polymerase (Promega AG, Dubendorf, Switzerland) in the same conditions as described above. The product of this amplification is ligated into the first MCS of pETDuet plasmid between the NcoI and BamHI restriction sites, providing the plasmid pETDuet-CrtE. The plasmid pETDuet-SsLPPS3-del4 (containing the SsLPPS3 cDNA with a 63-codons deletion (SsLPPS3-del4, SEQ ID NO:31, Example 4) is digested with the NdeI and KpnI restriction enzymes. The insert is recovered and transferred into the same sites of the pETDuet-CrtE plasmid resulting in the plasmid pETDuet-CrtE-SsLPPS3-del4 containing both the SsLPPS and CrtE genes under the control of a T7 promoter (FIG. 13B).

The plasmid pET101-1132-2-5 (containing the SsTps1132 cDNA with a 50-codons deletion (SsTps1132-2-5, SEQ ID NO:73, Example 8)) is digested with NcoI and SacI restriction enzymes and the insert transferred in the same sites of the plasmid pRSDuet-1 providing the plasmid pRSDuet-1132-2-5 (not represented in FIG. 13).

BL21 Star™(DE3) *E. coli* cells (Invitrogen) can be co-transformed with the 3 plasmids pACYCDuet-4506 (FIG. 13A), pETDuet-CrtE-SsLPPS3-del4 (FIG. 13B) and pRSDuet-1132-2-5 (each harbouring a different origin of replication and resistance gene). Transformed cells are selected on carbenicillin (50 μg/ml) chloramphenicol (34 μg/ml) kanamycin (35 μg/ml) LB-agarose plates. Single colonies are used to inoculate 5 mL liquid LB medium supplemented with the same antibiotics. The culture is incubated overnight at 37° C. The next day 2 mL of TB medium supplemented with the same antibiotics are inoculated with 0.2 mL of the overnight culture. After 6 hours incubation at 37° C., the culture is cooled down to 28° C. and 1 mM IPTG, 2 mg/mL mevalonate (prepared by dissolving mevalonolactone (Sigma) in 0.5N NaOH at a concentration of 1 g/mL and incubating the solution for 30 min at 37° C.) and 0.2 ml decane are added to each tube. The cultures are incubated for 48 hours at 28° C. The cultures are then extracted twice with 2 volumes of ethyl acetate, the organic phase is concentrated to 500 μL and analyzed by GC-MS as described above in Example 3.

This example shows that an *E. coli* cell transformed with both a LPP synthase and a sclareol synthase, as defined in the present invention, is capable of producing sclareol. The other enzymes with which the *E. coli* cell is transformed are not essential for the production of sclareol. Indeed sclareol is also produced when an *E. coli* cell is transformed with the LPP synthase and the sclareol synthase only, but in lower amounts. The other enzymes with which the *E. coli* cell is transformed are added for the only purpose of increasing the amount of precursor available to the LPP synthase and sclareol synthase.

Example 11

In Vivo Production of Sclareol in *E. coli* by Expression of a Fusion Protein Containing a LPP Synthase and a Sclareol Synthase The same approach is used for the production of sclareol with a fusion protein containing the LPP synthase and the sclareol synthase linked together in a unique polypeptide. A plasmid is prepared containing a new cDNA comprising the SsLLPS3-del4 sequence (SEQ ID NO:31) in the 5' part and 1132-2-5 sequence (SEQ ID NO:73) in the 3'part (SEQ ID NO:87). In this fusion cDNA, the stop codon of SsLPPS3-del4 cDNA and the start codon of the 1132-2-5 cDNA are deleted. The two cDNA are linked by a 15 bp sequence (SEQ ID NO:81) encoding for a peptide (SEQ ID NO:82) which constitutes the linker between the two protein domains. The amino acid sequence of the encoded fusion polypeptide is provided in SEQ ID NO:88.

The SsLPPS3-del4 cDNA (SEQ ID NO:31) is re-amplified from the pETDuet-SsLPPS3-del4 plasmid using the primers Sa3del4-fusion-inf1 (SEQ ID NO:83) and Sa3del-fusion-inf2 (SEQ ID NO:84). The first primer is designed to add at the 5'end a 15 bp sequence complementary to the NdeI region of the pETDuet-1 plasmid. The second primer is designed to remove the stop codon and add the sequence encoding for the linker peptide. The 1132-2-5 cDNA (SEQ ID NO:73) is reamplified from the plasmid pET101-1132-2-5 with the primers 1132-fusion-inf1 (SEQ ID NO:85) and 1132-inf2 (SEQ ID NO:86). As for SsLPPS-del4, these primers are designed to add the linker sequence at the 3'end and a 15 bp sequence complementary to the sequence of the KpnI region of the pETDuet-1 plasmid. The PCR is performed with the Pfu DNA polymerase (Promega AG, Dubendorf, Switzerland) in the same conditions as described above in Example 10. The plasmid pETDuet-CrtE-SsLPPS3-del4 is digested with the NdeI and KpnI enzymes and the linear plasmid DNA is purified from the insert. The two PCR products and the linear plasmid are combined and ligated together using In-Fusion™ Dry-Down PCR Cloning Kit (clontech). The plasmid obtained, pETDuet-CrtE-fusion-SsLPPS-1132 (FIG. 13C) is controlled DNA by sequencing of the insert.

To evaluate the production of sclareol from GGPP by this enzyme, BL21 Star™(DE3) *E. coli* cells (Invitrogen) can be co-transformed with the plasmids pACYCDuet-4506 (FIG. 13A) and pETDuet-CrtE-SsLPPS-1132-fusion (FIG. 13C). Transformed cells are selected on carbenicillin (50 μg/ml) chloramphenicol (34 μg/ml) LB-agarose plates. The culture, induction, supplementation with mevalonate, extraction and analysis are performed as described in Example 10.

This example shows that an *E. coli* cell transformed to express a fusion protein composed by a LPP synthase domain and a sclareol synthase domain, as defined in the present invention, is capable of producing sclareol. The other enzymes with which the *E. coli* cell is transformed are not essential for the production of sclareol. Indeed sclareol is also produced when an *E. coli* cell is transformed with the LPP synthase and the sclareol synthase only, but in much lower amount. The other enzymes with which the *E. coli* cell is transformed, are added for the unique purpose of increasing the amount of precursor available to the LPP synthase and sclareol synthase.

---

The invention claimed is:

1. A method for producing sclareol comprising
a) incubating geranylgeranyl pyrophosphate (GGPP) with an isolated polypeptide comprising the amino acid sequence of SEQ ID NO: 1 or 2, under conditions effective to form labdenediol diphosphate (LPP);
b) incubating the LPP produced in step a) with an isolated polypeptide comprising the amino acid sequence of SEQ ID NO: 3, under conditions effective to produce sclareol, thereby producing sclareol.

2. The method of claim 1, wherein steps a) and b) are carried out simultaneously by contacting GGPP with said polypeptide comprising the amino acid sequence SEQ ID NO: 1 or 2, together with said polypeptide comprising the amino acid sequence of SEQ ID NO: 3.

3. The method of claim 1, wherein steps a) and b) are carried out simultaneously by contacting GGPP with at least one fusion polypeptide comprising the amino acid sequence of SEQ ID NO: 1 or 2 and further comprising the amino acid sequence of SEQ ID NO: 3.

4. A method of producing sclareol comprising a) cultivating a non-human host organism or cell capable of producing GGPP and transformed to express a polypeptide comprising the amino acid sequence of SEQ ID NO: 1 or 2, and a polypeptide comprising the amino acid sequence of SEQ ID NO: 3, under conditions conducive to the production of sclareol, thereby producing sclareol.

5. The method of claim 4, further comprising, prior to step a), transforming a non-human host organism or cell capable of producing GGPP with a nucleic acid sequence encoding said polypeptide comprising the amino acid sequence of SEQ ID NO: 1 or 2 and with a nucleic acid sequence encoding said polypeptide comprising the amino acid sequence of SEQ ID NO: 3, so that said organism or cell expresses said polypeptides.

6. The method of claim 5, wherein said nucleic acid sequence encoding said polypeptide comprising the amino acid sequence of SEQ ID NO: 1 comprises the nucleic acid sequence of SEQ ID NO: 4, or said nucleic acid sequence encoding said polypeptide comprising the amino acid sequence of SEQ ID NO: 2 comprises the nucleic acid sequence of SEQ ID NO: 5, and said nucleic acid sequence encoding said polypeptide comprising the amino acid sequence of SEQ ID NO: 3 comprises the nucleic acid sequence of SEQ ID NO: 6.

7. The method according to claim 4, wherein said non-human host organism or cell is transformed with a nucleic acid sequence encoding a fusion polypeptide comprising the amino acid sequence of SEQ ID NO: 1 or 2 and the amino acid sequence of SEQ ID NO: 3, so that said organism or cell expresses said fusion polypeptide.

8. The method of claim 4, wherein said non-human host organism is a plant, a prokaryote or a fungus.

9. The method of claim 4, wherein said non-human host organism is a microorganism.

10. The method of claim 9, wherein said microorganism is a bacteria or yeast.

11. The method of claim 10, wherein said bacteria is *E. coli* and said yeast is *Saccharomyces cerevisiae*.

12. The method of claim 4, wherein said non-human host cell is a plant cell.

13. A fusion polypeptide capable of catalyzing the synthesis of geranylgeranyl pyrophosphate (GGPP) to sclareol and comprising the amino acid sequence of SEQ ID NO: 1 or 2 and the amino acid sequence of SEQ ID NO: 3.

14. A nucleic acid comprising a nucleotide sequence encoding the fusion polypeptide of claim 13.

15. The nucleic acid sequence of claim 14, comprising the nucleotide sequence of SEQ ID NO:4 or 5 and further comprising the nucleotide sequence of SEQ ID NO:6.

16. An expression vector comprising the nucleic acid sequence of claim 14.

17. The expression vector of claim 16, wherein said vector is a viral vector, a bacteriophage or a plasmid.

18. The expression vector of claim 16, wherein said nucleic acid sequence encoding said fusion polypeptide is operably linked to at least one nucleic acid regulatory sequence which controls transcription, translation initiation or termination.

19. A non-human host organism or cell transformed to harbor both a nucleic acid sequence encoding a polypeptide comprising the amino acid sequence of SEQ ID NO:1 or 2 and a nucleic acid sequence encoding a polypeptide comprising the amino acid sequence of SEQ ID NO:3, so that said organism or cell heterologously expresses or over-expresses said polypeptides.

20. The non-human host organism or cell of claim 19, transformed to harbor a nucleic acid sequence encoding a fusion polypeptide comprising the amino acid sequence of SEQ ID NO:1 or 2 and the amino acid sequence of SEQ ID NO:3.

21. The non-human host organism of claim 19, wherein said non-human host organism is a plant, a prokaryote or a fungus.

22. The non-human host organism of claim 19, wherein said non-human host organism is a microorganism.

23. The non-human host organism of claim 22, wherein said microorganism is a bacteria or yeast.

24. The non-human host organism of claim 23, wherein said bacteria is *E. coli* and said yeast is *Saccharomyces cerevisiae*.

25. The cell of claim 19, wherein said cell is a plant cell.

26. A method for producing at least one fusion polypeptide capable of catalyzing the synthesis of geranylgeranyl pyrophosphate (GGPP) to sclareol comprising
   a) culturing a non-human host organism or cell transformed with the expression vector of claim 16 to express or over-express the polypeptide encoded by said nucleotide sequence; and
   b) isolating said fusion polypeptide from the non-human host organism or cell cultured in step a).

27. The method of claim 26, further comprising, prior to step a), transforming said non-human host organism or cell with said expression vector.

28. A method for preparing a variant fusion polypeptide capable of catalyzing the synthesis of geranylgeranyl pyrophosphate (GGPP) to sclareol comprising the steps of:
   a) providing a nucleic acid sequence according to claim 14;
   b) modifying said nucleic acid sequence to obtain at least one mutant nucleic acid sequence;
   c) transforming host cells or unicellular organisms with the mutant nucleic acid sequence to express a polypeptide encoded by the mutant nucleic acid sequence;
   d) screening the polypeptide for at least one desired modified enzymatic activity; and,
   e) optionally, if the polypeptide has no desired modified enzymatic activity, repeating the process steps (a) to (d) until a polypeptide with at least one desired modified enzymatic activity is obtained;
   f) optionally, if a polypeptide having at least one desired modified enzymatic activity was identified in step (d), isolating the corresponding mutant nucleic acid obtained in step (c).

29. The method of claim 1, further comprising isolating sclareol.

30. The method of claim 4, further comprising isolating sclareol.

* * * * *

SEQUENCE LISTING

```
<160> NUMBER OF SEQ ID NOS: 88

<210> SEQ ID NO 1
<211> LENGTH: 785
<212> TYPE: PRT
<213> ORGANISM: Salvia sclarea

<400> SEQUENCE: 1

Met Thr Ser Val Asn Leu Ser Arg Ala Pro Ala Ala Ile Thr Arg Arg
1               5                   10                  15

Arg Leu Gln Leu Gln Pro Glu Phe His Ala Glu Cys Ser Trp Leu Lys
            20                  25                  30

Ser Ser Ser Lys His Ala Pro Leu Thr Leu Ser Cys Gln Ile Arg Pro
```

```
                35                  40                  45
Lys Gln Leu Ser Gln Ile Ala Glu Leu Arg Val Thr Ser Leu Asp Ala
 50                  55                  60
Ser Gln Ala Ser Glu Lys Asp Ile Ser Leu Val Gln Thr Pro His Lys
 65                  70                  75                  80
Val Glu Val Asn Glu Lys Ile Glu Ser Ile Glu Tyr Val Gln Asn
                 85                  90                  95
Leu Leu Met Thr Ser Gly Asp Gly Arg Ile Ser Val Ser Pro Tyr Asp
                100                 105                 110
Thr Ala Val Ile Ala Leu Ile Lys Asp Leu Lys Gly Arg Asp Ala Pro
                115                 120                 125
Gln Phe Pro Ser Cys Leu Glu Trp Ile Ala His His Gln Leu Ala Asp
                130                 135                 140
Gly Ser Trp Gly Asp Glu Phe Phe Cys Ile Tyr Asp Arg Ile Leu Asn
145                 150                 155                 160
Thr Leu Ala Cys Val Val Ala Leu Lys Ser Trp Asn Leu His Ser Asp
                165                 170                 175
Ile Ile Glu Lys Gly Val Thr Tyr Ile Lys Glu Asn Val His Lys Leu
                180                 185                 190
Lys Gly Ala Asn Val Glu His Arg Thr Ala Gly Phe Glu Leu Val Val
                195                 200                 205
Pro Thr Phe Met Gln Met Ala Thr Asp Leu Gly Ile Gln Asp Leu Pro
                210                 215                 220
Tyr Asp His Pro Leu Ile Lys Glu Ile Ala Asp Thr Lys Gln Gln Arg
225                 230                 235                 240
Leu Lys Glu Ile Pro Lys Asp Leu Val Tyr Gln Met Pro Thr Asn Leu
                245                 250                 255
Leu Tyr Ser Leu Glu Gly Leu Gly Asp Leu Glu Trp Glu Arg Leu Leu
                260                 265                 270
Lys Leu Gln Ser Gly Asn Gly Ser Phe Leu Thr Ser Pro Ser Ser Thr
                275                 280                 285
Ala Ala Val Leu Met His Thr Lys Asp Glu Lys Cys Leu Lys Tyr Ile
                290                 295                 300
Glu Asn Ala Leu Lys Asn Cys Asp Gly Gly Ala Pro His Thr Tyr Pro
305                 310                 315                 320
Val Asp Ile Phe Ser Arg Leu Trp Ala Ile Asp Arg Leu Gln Arg Leu
                325                 330                 335
Gly Ile Ser Arg Phe Phe Gln Glu Ile Lys Tyr Phe Leu Asp His
                340                 345                 350
Ile Glu Ser Val Trp Glu Glu Thr Gly Val Phe Ser Gly Arg Tyr Thr
                355                 360                 365
Lys Phe Ser Asp Ile Asp Asp Thr Ser Met Gly Val Arg Leu Leu Lys
                370                 375                 380
Met His Gly Tyr Asp Val Asp Pro Asn Val Leu Lys His Phe Lys Gln
385                 390                 395                 400
Gln Asp Gly Lys Phe Ser Cys Tyr Ile Gly Gln Ser Val Glu Ser Ala
                405                 410                 415
Ser Pro Met Tyr Asn Leu Tyr Arg Ala Ala Gln Leu Arg Phe Pro Gly
                420                 425                 430
Glu Glu Val Leu Glu Glu Ala Thr Lys Phe Ala Phe Asn Phe Leu Gln
                435                 440                 445
Glu Met Leu Val Lys Asp Arg Leu Gln Glu Arg Trp Val Ile Ser Asp
                450                 455                 460
```

```
His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
            500                 505                 510

Ser Asn Asp Thr Tyr Lys Glu Leu Ala Ile Leu Asp Phe Asn Arg Cys
        515                 520                 525

Gln Thr Gln His Gln Leu Glu Trp Ile His Met Gln Glu Trp Tyr Asp
    530                 535                 540

Arg Cys Ser Leu Ser Glu Phe Gly Ile Ser Lys Arg Glu Leu Leu Arg
545                 550                 555                 560

Ser Tyr Phe Leu Ala Ala Thr Ile Phe Glu Pro Glu Arg Thr Gln
                565                 570                 575

Glu Arg Leu Leu Trp Ala Lys Thr Arg Ile Leu Ser Lys Met Ile Thr
                580                 585                 590

Ser Phe Val Asn Ile Ser Gly Thr Leu Ser Leu Asp Tyr Asn Phe
                595                 600                 605

Asn Gly Leu Asp Glu Ile Ile Ser Ser Ala Asn Glu Asp Gln Gly Leu
610                 615                 620

Ala Gly Thr Leu Leu Ala Thr Phe His Gln Leu Leu Asp Gly Phe Asp
625                 630                 635                 640

Ile Tyr Thr Leu His Gln Leu Lys His Val Trp Ser Gln Trp Phe Met
                645                 650                 655

Lys Val Gln Gln Gly Gly Ser Gly Gly Asp Ala Val Leu Leu
                660                 665                 670

Ala Asn Thr Leu Asn Ile Cys Ala Gly Leu Asn Glu Asp Val Leu Ser
                675                 680                 685

Asn Asn Glu Tyr Thr Ala Leu Ser Thr Leu Thr Asn Lys Ile Cys Asn
            690                 695                 700

Arg Leu Ala Gln Ile Gln Asp Asn Lys Ile Leu Gln Val Val Asp Gly
705                 710                 715                 720

Ser Ile Lys Asp Lys Glu Leu Glu Gln Asp Met Gln Ala Leu Val Lys
                725                 730                 735

Leu Val Leu Gln Glu Asn Gly Gly Ala Val Asp Arg Asn Ile Arg His
                740                 745                 750

Thr Phe Leu Ser Val Ser Lys Thr Phe Tyr Tyr Asp Ala Tyr His Asp
                755                 760                 765

Asp Glu Thr Thr Asp Leu His Ile Phe Lys Val Leu Phe Arg Pro Val
            770                 775                 780

Val
785

<210> SEQ ID NO 2
<211> LENGTH: 784
<212> TYPE: PRT
<213> ORGANISM: Salvia sclarea

<400> SEQUENCE: 2

Met Thr Ser Val Asn Leu Ser Arg Ala Pro Ala Ile Ile Arg Arg
1               5                   10                  15

Arg Leu Gln Leu Gln Pro Glu Phe His Ala Glu Cys Ser Trp Leu Lys
                20                  25                  30

Ser Ser Ser Lys His Ala Pro Phe Thr Leu Ser Cys Gln Ile Arg Pro
            35                  40                  45
```

```
Lys Gln Leu Ser Gln Ile Ala Glu Leu Arg Val Thr Ser Leu Asp Ala
             50                  55                  60

Ser Gln Ala Ser Glu Lys Asp Ile Ser Leu Val Gln Thr Pro His Lys
 65                  70                  75                  80

Val Glu Val Asn Glu Lys Ile Glu Glu Ser Ile Glu Tyr Val Gln Asn
                     85                  90                  95

Leu Leu Met Thr Ser Gly Asp Gly Arg Ile Ser Val Ser Pro Tyr Asp
                    100                 105                 110

Thr Ala Val Ile Ala Leu Ile Lys Asp Leu Lys Gly Arg Asp Ala Pro
                115                 120                 125

Gln Phe Pro Ser Cys Leu Glu Trp Ile Ala His Gln Leu Ala Asp
            130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu Gln Ser Asp
                165                 170                 175

Ile Ile Glu Lys Gly Val Thr Tyr Ile Lys Glu Asn Val His Lys Leu
                180                 185                 190

Lys Gly Ala Asn Val Glu His Arg Thr Ala Gly Phe Glu Leu Val Val
                195                 200                 205

Pro Thr Phe Met Gln Met Ala Thr Asp Leu Gly Ile Gln Gly Leu Pro
                210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
                260                 265                 270

Lys Leu Gln Ser Gly Asn Gly Ser Phe Leu Thr Ser Pro Ser Ser Thr
                275                 280                 285

Ala Ala Val Leu Met His Thr Lys Asp Glu Lys Cys Leu Lys Tyr Ile
            290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335

Gly Ile Ser Arg Phe Phe Gln His Glu Ile Lys Tyr Phe Leu Asp His
                340                 345                 350

Ile Glu Ser Val Trp Glu Glu Thr Gly Val Phe Ser Gly Arg Tyr Thr
                355                 360                 365

Lys Phe Ser Asp Ile Asp Asp Thr Ser Met Gly Val Arg Leu Leu Lys
                370                 375                 380

Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
                405                 410                 415

Ser Pro Met Tyr Asn Leu Tyr Arg Ala Ala Gln Leu Arg Phe Pro Gly
                420                 425                 430

Glu Glu Val Leu Glu Glu Ala Thr Lys Phe Ala Phe Asn Phe Leu Gln
                435                 440                 445

Glu Met Leu Val Lys Asp Arg Leu Gln Glu Arg Trp Val Ile Ser Asp
            450                 455                 460

His Leu Phe Asp Glu Ile Lys Leu Gly Leu Lys Met Pro Trp Tyr Ala
465                 470                 475                 480
```

```
Thr Leu Pro Arg Val Glu Ala Ala Tyr Tyr Leu Asp His Tyr Ala Gly
            485                 490                 495
Ser Gly Asp Val Trp Ile Gly Lys Ser Phe Tyr Arg Met Pro Glu Ile
        500                 505                 510
Ser Asn Asp Thr Tyr Lys Glu Leu Ala Ile Leu Asp Phe Asn Arg Cys
    515                 520                 525
Gln Thr Gln His Gln Leu Glu Trp Ile Gln Met Gln Glu Trp Tyr Asp
530                 535                 540
Arg Cys Ser Leu Ser Glu Phe Gly Ile Ser Lys Arg Glu Leu Leu Arg
545                 550                 555                 560
Ser Tyr Phe Leu Ala Ala Thr Ile Phe Glu Pro Glu Arg Thr Gln
                565                 570                 575
Glu Arg Leu Leu Trp Ala Lys Thr Arg Ile Leu Ser Lys Met Ile Thr
            580                 585                 590
Ser Phe Val Asn Ile Ser Gly Thr Thr Leu Ser Leu Asp Tyr Asn Phe
        595                 600                 605
Asn Gly Leu Asp Glu Ile Ile Ser Ala Asn Glu Asp Gln Gly Leu Ala
    610                 615                 620
Gly Thr Leu Leu Ala Thr Phe His Gln Leu Leu Asp Gly Phe Asp Ile
625                 630                 635                 640
Tyr Thr Leu His Gln Leu Lys His Val Trp Ser Gln Trp Phe Met Lys
            645                 650                 655
Val Gln Gln Gly Glu Gly Ser Gly Glu Asp Ala Val Leu Leu Ala
        660                 665                 670
Asn Thr Leu Asn Ile Cys Ala Gly Leu Asn Glu Asp Val Leu Ser Asn
    675                 680                 685
Asn Glu Tyr Thr Ala Leu Ser Thr Leu Thr Asn Lys Ile Cys Asn Arg
    690                 695                 700
Leu Ala Gln Ile Gln Asp Asn Lys Ile Leu Gln Val Val Asp Gly Ser
705                 710                 715                 720
Ile Lys Asp Lys Glu Leu Glu Gln Asp Met Gln Ala Leu Val Lys Leu
            725                 730                 735
Val Leu Gln Glu Asn Gly Gly Ala Val Asp Arg Asn Ile Arg His Thr
        740                 745                 750
Phe Leu Ser Val Ser Lys Thr Phe Tyr Tyr Asp Ala Tyr His Asp Asp
    755                 760                 765
Glu Thr Thr Asp Leu His Ile Phe Lys Val Leu Phe Arg Pro Val Val
    770                 775                 780

<210> SEQ ID NO 3
<211> LENGTH: 575
<212> TYPE: PRT
<213> ORGANISM: Salvia sclarea

<400> SEQUENCE: 3

Met Ser Leu Ala Phe Asn Val Gly Val Thr Pro Phe Ser Gly Gln Arg
1               5                   10                  15
Val Gly Ser Arg Lys Glu Lys Phe Pro Val Gln Gly Phe Pro Val Thr
            20                  25                  30
Thr Pro Asn Arg Ser Arg Leu Ile Val Asn Cys Ser Leu Thr Thr Ile
        35                  40                  45
Asp Phe Met Ala Lys Met Lys Glu Asn Phe Lys Arg Glu Asp Asp Lys
    50                  55                  60
Phe Pro Thr Thr Thr Leu Arg Ser Glu Asp Ile Pro Ser Asn Leu
65                  70                  75                  80
```

```
Cys Ile Ile Asp Thr Leu Gln Arg Leu Gly Val Asp Gln Phe Phe Gln
                85                  90                  95
Tyr Glu Ile Asn Thr Ile Leu Asp Asn Thr Phe Arg Leu Trp Gln Glu
            100                 105                 110
Lys His Lys Val Ile Tyr Gly Asn Val Thr Thr His Ala Met Ala Phe
            115                 120                 125
Arg Leu Leu Arg Val Lys Gly Tyr Glu Val Ser Ser Glu Glu Leu Ala
        130                 135                 140
Pro Tyr Gly Asn Gln Glu Ala Val Ser Gln Gln Thr Asn Asp Leu Pro
145                 150                 155                 160
Met Ile Ile Glu Leu Tyr Arg Ala Ala Asn Glu Arg Ile Tyr Glu Glu
                165                 170                 175
Glu Arg Ser Leu Glu Lys Ile Leu Ala Trp Thr Thr Ile Phe Leu Asn
            180                 185                 190
Lys Gln Val Gln Asp Asn Ser Ile Pro Asp Lys Lys Leu His Lys Leu
        195                 200                 205
Val Glu Phe Tyr Leu Arg Asn Tyr Lys Gly Ile Thr Ile Arg Leu Gly
    210                 215                 220
Ala Arg Arg Asn Leu Glu Leu Tyr Asp Met Thr Tyr Tyr Gln Ala Leu
225                 230                 235                 240
Lys Ser Thr Asn Arg Phe Ser Asn Leu Cys Asn Glu Asp Phe Leu Val
                245                 250                 255
Phe Ala Lys Gln Asp Phe Asp Ile His Glu Ala Gln Asn Gln Lys Gly
            260                 265                 270
Leu Gln Gln Leu Gln Arg Trp Tyr Ala Asp Cys Arg Leu Asp Thr Leu
        275                 280                 285
Asn Phe Gly Arg Asp Val Val Ile Ile Ala Asn Tyr Leu Ala Ser Leu
    290                 295                 300
Ile Ile Gly Asp His Ala Phe Asp Tyr Val Arg Leu Ala Phe Ala Lys
305                 310                 315                 320
Thr Ser Val Leu Val Thr Ile Met Asp Asp Phe Phe Asp Cys His Gly
                325                 330                 335
Ser Ser Gln Glu Cys Asp Lys Ile Ile Glu Leu Val Lys Glu Trp Lys
            340                 345                 350
Glu Asn Pro Asp Ala Glu Tyr Gly Ser Glu Glu Leu Glu Ile Leu Phe
        355                 360                 365
Met Ala Leu Tyr Asn Thr Val Asn Glu Leu Ala Glu Arg Ala Arg Val
    370                 375                 380
Glu Gln Gly Arg Ser Val Lys Glu Phe Leu Val Lys Leu Trp Val Glu
385                 390                 395                 400
Ile Leu Ser Ala Phe Lys Ile Glu Leu Asp Thr Trp Ser Asn Gly Thr
                405                 410                 415
Gln Gln Ser Phe Asp Glu Tyr Ile Ser Ser Ser Trp Leu Ser Asn Gly
            420                 425                 430
Ser Arg Leu Thr Gly Leu Leu Thr Met Gln Phe Val Gly Val Lys Leu
        435                 440                 445
Ser Asp Glu Met Leu Met Ser Glu Cys Thr Asp Leu Ala Arg His
450                 455                 460
Val Cys Met Val Gly Arg Leu Asn Asp Val Cys Ser Ser Glu Arg
465                 470                 475                 480
Glu Arg Glu Glu Asn Ile Ala Gly Lys Ser Tyr Ser Ile Leu Leu Ala
                485                 490                 495
Thr Glu Lys Asp Gly Arg Lys Val Ser Glu Asp Glu Ala Ile Ala Glu
```

```
                500             505             510
Ile Asn Glu Met Val Glu Tyr His Trp Arg Lys Val Leu Gln Ile Val
            515                 520                 525

Tyr Lys Lys Glu Ser Ile Leu Pro Arg Arg Cys Lys Asp Val Phe Leu
        530                 535                 540

Glu Met Ala Lys Gly Thr Phe Tyr Ala Tyr Gly Ile Asn Asp Glu Leu
545                 550                 555                 560

Thr Ser Pro Gln Gln Ser Lys Glu Asp Met Lys Ser Phe Val Phe
                565                 570                 575

<210> SEQ ID NO 4
<211> LENGTH: 2358
<212> TYPE: DNA
<213> ORGANISM: Salvia sclarea

<400> SEQUENCE: 4
atgacttctg taaatttgag cagagcacca gcagcgatta cccggcgcag gctgcagcta      60
cagccggaat tcatgccga gtgttcatgg ctgaaaagca gcagcaaaca cgcgcccttg     120
accttgagtt gccaaatccg tcctaagcaa ctctcccaaa tagctgaatt gagagtaaca     180
agcctggatg cgtcgcaagc gagtgaaaaa gacatttccc ttgttcaaac tccgcataag     240
gttgaggtta atgaaaagat cgaggagtca atcgagtacg tccaaaatct gttgatgacg     300
tcgggcgacg ggcgaataag cgtgtcaccc tatgacacgg cagtgatcgc cctgatcaag     360
gacttgaaag gcgcgacgc cccgcagttt ccgtcatgtc tcgagtggat cgcgcaccac     420
caactggctg atggctcatg gggcgacgaa ttcttctgta tttatgatcg gattctaaat     480
acattggcat gtgtcgtagc cttgaaatca tggaaccttc actctgatat tattgaaaaa     540
ggagtgacgt acatcaagga gaatgtgcat aaacttaaag gtgcaaatgt tgagcacagg     600
acagcggggt cgaacttgt ggttcctact tttatgcaaa tggccacaga tttgggcatc     660
caagatctgc cctatgatca tcccctcatc aaggagattg ctgacacaaa acaacaaaga     720
ttgaaagaga tacccaagga tttggtttac caaatgccaa cgaatttact gtacagttta     780
gaagggttag agatttgga gtgggaaagg ctactgaaac tgcagtcggg caatggctcc     840
ttcctcactt cgccgtcgtc caccgccgcc gtcttgatgc ataccaaaga tgaaaaatgt     900
ttgaaataca tcgaaaacgc cctcaagaat tgcgacggag gagcaccaca tacttatcca     960
gtcgatatct tctcaagact ttgggcaatc gataggctac aacgcctagg aatttctcgt    1020
ttcttccagc acgagatcaa gtatttctta gatcacatcg aaagcgtttg ggaggagacc    1080
ggagttttca gtggaagata cgaaatttag cgatattg atgacacgtc catgggcgtt    1140
aggcttctca aaatgcacgg atacgacgtc gatccaaatg tactaaaaca tttcaagcaa    1200
caagatggta atttttcctg ctacattggt caatcggtcg agtctgcatc tccaatgtac    1260
aatctttata gggctgctca actaagattt ccaggagaag aagttcttga agaagccact    1320
aaatttgcct ttaacttctt gcaagaaatg ctagtcaaag atcgacttca agaaagatgg    1380
gtgatatccg accacttatt tgatgagata aagctgggt tgaagatgcc atggtacgcc    1440
actctacccc gagtcgaggc tgcatattat ctagaccatt atgctggttc tggtgatgta    1500
tggattggca agagtttcta caggatgcca gaaatcagca atgatacata caaggagctt    1560
gcgatattgg atttcaacag atgccaaaca caacatcagt tggagtggat ccacatgcag    1620
gaatggtacg acagatgcag ccttagcgaa ttcgggataa gcaaaagaga gttgcttcgc    1680
tcttactttc tggccgcagc aaccatattc gaaccggaga gaactcaaga gaggcttctg    1740
```

-continued

```
tgggccaaaa ccagaattct ttctaagatg atcacttcat tgtcaacat tagtggaaca    1800 acactatctt tggactacaa tttcaatggc ctcgatgaaa taattagtag tgccaatgaa    1860
gatcaaggac tggctgggac tctgctggca accttccatc aacttctaga cggattcgat    1920
atatacactc tccatcaact caaacatgtt tggagccaat ggttcatgaa agtgcagcaa    1980
ggagagggaa gcggcgggga agacgcggtg ctcctagcga acacgctcaa catctgcgcc    2040
ggcctcaacg aagacgtgtt gtccaacaat gaatacacgg ctctgtccac cctcacaaat    2100
aaaatctgca atcgcctcgc ccaaattcaa gacaataaga ttctccaagt tgtggatggg    2160
agcataaagg ataaggagct agaacaggat atgcaggcgt tggtgaagtt agtgcttcaa    2220
gaaaatggcg gcgccgtaga cagaaacatc agacacacgt ttttgtcggt ttccaagact    2280
ttctactacg atgcctacca cgacgatgag acgaccgatc ttcatatctt caaagtactc    2340
tttcgaccgg ttgtatga                                                 2358
```

<210> SEQ ID NO 5
<211> LENGTH: 2355
<212> TYPE: DNA
<213> ORGANISM: Salvia sclarea

<400> SEQUENCE: 5

```
atgacttctg taaatttgag cagagcacca gcagcgatta tccggcgcag gctgcagcta     60
cagccggaat tcatgccga gtgttcatgg ctgaaaagca gcagcaaaca cgcgcccttc     120
accttgagtt gccaaatccg tcctaagcaa ctctcccaaa tagctgaatt gagagtaaca    180
agcctggatg cgtcgcaagc gagtgaaaaa gacatttccc ttgttcaaac tccgcataag    240
gttgaggtta atgaaaagat cgaggagtca atcgagtacg tccaaaatct gttgatgacg    300
tcgggcgacg ggcgaataag cgtgtcaccc tatgacacgg cagtgatcgc cctgatcaag    360
gacttgaaag ggcgcgacgc cccgcagttt ccgtcatgtc tcgagtggat cgcgcaccac    420
caactggctg atgctcatg gggcgacgaa ttcttctgta tttatgatcg gattctaaat    480
acattggcat gtgtcgtagc cttgaaatca tggaaccttc aatctgatat tattgaaaaa    540 ggtgtgcacgt acatcaagga gaatgtgcat aaacttaaag gtgcaaatgt tgagcacagg    600
acagcggggt tcgaacttgt ggttcctact tttatgcaaa tggccacaga tttgggcatc    660
caaggtctgc cctatgatca tcccctcatc aaggagattg ctgacacaaa acaacaaaga    720
ttgaaagaga tacccaagga tttggtttac caaatgccaa cgaatttact gtacagttta    780
gaagggttag gagatttgga gtgggaaagg ttactgaaac tgcagtcggg caatggctcc    840
ttcctcactt cgccgtcgtc caccgccgcc gtcttgatgc ataccaaaga tgaaaaatgt    900
ttgaaataca tcgaaaacgc cctcaagaat tgcgacggag gagcaccaca tacttatcca    960
gtcgatatct tctcaagact ttgggcaatc gataggctac aacgctagg aatttctcgt    1020 ttcttccagc acgagatcaa gtatttctta gatcacatcg aaagcgttg ggaggagacc    1080 ggagtttca gtggaagata tacgaaattt agcgatattg atgacacgtc catgggcgtt    1140
aggcttctca aaatgcacgg atacgacgtc gatccaaatg tactaaaaca tttcaagcaa    1200
caagatggta atttcctg ctacattggt caatcggtcg agtctgcatc tccaatgtac    1260
aatctttata gggctgctca actaagattt ccaggagaag aagttcttga agaagccact    1320
aaatttgcct ttaacttctt gcaagaaatg ctagtcaaag atcgacttca gaaagatgg    1380 gtgatatccg accacttatt tgatgagata aagctggggt tgaagatgcc atggtacgcc    1440
actctacccc gagtcgaggc tgcatattat ctagaccatt atgctggttc tggtgatgta    1500
```

-continued

```
tggattggca agagtttcta caggatgcca gaaatcagca atgatacata caaggagctt    1560
gcgatattgg atttcaacag atgccaaaca caacatcagt tggagtggat ccagatgcag    1620
gaatggtacg acagatgcag ccttagcgaa ttcgggataa gcaaaagaga gttgcttcgc    1680
tcttactttc tggccgcagc aaccatattc gaaccggaga gaactcaaga gaggcttctg    1740
tgggccaaaa ccagaattct ttctaagatg atcacttcat tgtcaacat  tagtggaaca    1800 acactatctt tggactacaa tttcaatggc ctcgatgaaa taattagtgc caatgaagat    1860
caaggactgg ctgggactct gctggcaacc ttccatcaac ttctagacgg attcgatata    1920
tacactctcc atcaactcaa acatgtttgg agccaatggt tcatgaaagt gcagcaagga    1980
gagggaagcg gcggggaaga cgcggtgctc ctagcgaaca cgctcaacat ctgcgccggc    2040
ctcaacgaag acgtgttgtc caacaatgaa tacacggctc tgtccaccct cacaaataaa    2100
atctgcaatc gcctcgccca aattcaagac aataagattc tccaagttgt ggatgggagc    2160
ataaaggata aggagctaga acaggatatg caggcgttgg tgaagttagt gcttcaagaa    2220
aatggcggcg ccgtagacag aaacatcaga cacacgtttt tgtcggtttc caagactttc    2280
tactacgatg cctaccacga cgatgagacg accgatcttc atatcttcaa agtactcttt    2340
cgaccggttg tatga                                                     2355
```

<210> SEQ ID NO 6
<211> LENGTH: 1728
<212> TYPE: DNA
<213> ORGANISM: Salvia sclarea

<400> SEQUENCE: 6

```
atgtcgctcg ccttcaacgt cggagttacg cctttctccg gccaaagagt tgggagcagg      60
aaagaaaaat ttccagtcca aggatttcct gtgaccaccc ccaataggtc acgtctcatc     120
gttaactgca gccttactac aatagatttc atggcgaaaa tgaaagagaa tttcaagagg     180
gaagacgata aatttccaac gacaacgact cttcgatccg aagatatacc ctctaatttg     240
tgtataatcg acacccttca aaggttgggg gtcgatcaat tcttccaata tgaaatcaac     300
actattctag ataacacatt caggttgtgg caagaaaaac acaaagttat atatggcaat     360
gttactactc atgcaatggc atttaggctt ttgcgagtga aggatacga  agtttcatca     420 gaggagttgg ctccatatgg taaccaagag gctgttagcc agcaaacaaa tgacctgccg     480
atgattattg agctttatag agcagcaaat gagagaatat atgaagaaga gaggagtctt     540
gaaaaaattc ttgcttggac taccatcttt ctcaataagc aagtgcaaga taactcaatt     600
cccgacaaaa aactgcacaa actggtggaa ttctacttga ggaattacaa aggcataacc     660
ataagattgg gagctagacg aaacctcgag ctatatgaca tgacctacta tcaagctctg     720
aaatctacaa acaggttctc taatttatgc aacgaagatt ttctagtttt cgcaaagcaa     780
gatttcgata tacatgaagc ccagaaccag aaaggacttc aacaactgca aaggtggtat     840
gcagattgta ggttggacac cttaaacttt ggaagagatg tagttattat tgctaattat     900
ttggcttcat taattattgg tgatcatgcg tttgactatg ttcgtctcgc atttgccaaa     960
acatctgtgc ttgtaacaat tatggatgat ttttcgact  gtcatggctc tagtcaagag    1020
tgtgacaaga tcattgaatt agtaaaagaa tggaaggaga atccggatgc agagtacgga    1080
tctgaggagc ttgagatcct ttttatggcg ttgtacaata cagtaaatga gttggcggag    1140
agggctcgtg ttgaacaggg cgtagtgtc  aaagagtttc tagtcaaact gtgggttgaa    1200
atactctcag ctttcaagat agaattagat acatggagca atggcacgca gcaaagcttc    1260
```

-continued

```
gatgaataca tttcttcgtc gtggttgtcg aacggttccc ggctgacagg tctcctgacg    1320
atgcaattcg tcggagtaaa attgtccgat gaaatgctta tgagtgaaga gtgcactgat    1380
ttggctaggc atgtctgtat ggtcggccgg ctgctcaacg acgtgtgcag ttctgagagg    1440
gagcgcgagg aaaatattgc aggaaaaagt tatagcattc tactagcaac tgagaaagat    1500
ggaagaaaag ttagtgaaga tgaagccatt gcagagatca atgaaatggt tgaatatcac    1560
tggagaaaag tgttgcagat tgtgtataaa aagaaagca ttttgccaag aagatgcaaa     1620
gatgtatttt tggagatggc taagggtacg ttttatgctt atgggatcaa cgatgaattg    1680
acttctcctc agcaatccaa ggaagatatg aaatcctttg tcttttga                1728

<210> SEQ ID NO 7
<211> LENGTH: 22
<212> TYPE: DNA
<213> ORGANISM: Artificial sequence
<220> FEATURE:
<223> OTHER INFORMATION: Oligonucleotide primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 7
gayrtngayg ayacngcnat gg                                              22

<210> SEQ ID NO 8
<211> LENGTH: 24
<212> TYPE: DNA
<213> ORGANISM: Artificial sequence
<220> FEATURE:
<223> OTHER INFORMATION: Oligonucleotide primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 8
gtyttnccna kccanacrtc ryyt                                            24

<210> SEQ ID NO 9
<211> LENGTH: 354
<212> TYPE: DNA
<213> ORGANISM: Salvia sclarea

<400> SEQUENCE: 9
gcgttaggct tctcaaaatg cacggatacg acgtcgatcc aaatgtacta aaacatttca     60
agcaacaaga tggtaaattt tcctgctaca ttggtcaatc ggtcgagtct gcatctccaa    120
tgtacaatct ttatagggct gctcaactaa gatttccagg agaagaagtt cttgaagaag    180
ccactaaatt tgcctttaac ttcttgcaag aaatgctagt caaagatcga cttcaagaaa    240
```

```
gatgggtgat atccgaccac ttatttgatg agataaagct ggggttgaag atgccatggt    300
acgccactct accccgagtc gaggctgcat attatctaga ccattatgct ggtt          354
```

<210> SEQ ID NO 10
<211> LENGTH: 29
<212> TYPE: DNA
<213> ORGANISM: Artificial sequence
<220> FEATURE:
<223> OTHER INFORMATION: Synthetic oligonucleotide primer

<400> SEQUENCE: 10

```
gcacggatac gacgtcgatc caaatgtac                                       29
```

<210> SEQ ID NO 11
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 11

```
gggctgctca actaagattt ccaggag                                         27
```

<210> SEQ ID NO 12
<211> LENGTH: 29
<212> TYPE: DNA
<213> ORGANISM: Artificial sequence
<220> FEATURE:
<223> OTHER INFORMATION: Synthetic oligonucleotide primer

<400> SEQUENCE: 12

```
gggtgatatc cgaccactta tttgatgag                                       29
```

<210> SEQ ID NO 13
<211> LENGTH: 36
<212> TYPE: DNA
<213> ORGANISM: Artificial sequence
<220> FEATURE:
<223> OTHER INFORMATION: Synthetic oligonucleotide primer

<400> SEQUENCE: 13

```
aattcggtac ccgggatcct tttttttttt tttttt                               36
```

<210> SEQ ID NO 14
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 14

```
aattcggtac ccgggatcc                                                  19
```

<210> SEQ ID NO 15
<211> LENGTH: 1271
<212> TYPE: DNA
<213> ORGANISM: Salvia sclarea

<400> SEQUENCE: 15

```
aagaagttct tgaagaagcc actaaatttg cctttaactt cttgcaagaa atgctagtca     60
aagatcgact tcaagaaaga tgggtgatat ccgaccactt atttgatgag ataaagctgg    120
ggttgaagat gccatggtac gccactctac cccgagtcga ggctgcatat tatctagacc    180
attatgctgg ttctggtgat gtatggattg gcaagagttt ctacaggatg ccagaaatca    240
```

-continued

```
gcaatgatac atacaaggag cttgcgatat tggatttcaa cagatgccaa acacaacatc      300
agttggagtg gatccatatg caggaatggt acgacagatg cagccttagc gaattcggga      360
taagcaaaag agagttgctt cgctcttact ttctggccgc agcaaccata ttcgaaccgg      420
agagaactca agagaggctt ctgtgggcca aaaccagaat tctttctaag atgatcactt      480
catttgtcaa cattagtgga acaacactat ctttggacta caatttcaat ggcctcgatg      540
aaataattag tagtgccaat gaagatcaag gactggctgg gactctgctg caaccttcc       600 atcaacttct agacggattc gatatataca ctctccatca actcaaacat gtttggagcc      660
aatggttcat gaaagtgcag caaggagagg gaagcggcgg ggaagacgcg gtgctcctag      720
cgaacacgct caacatctgc gccggcctca acgaagacgt gttgtccaac aatgaataca      780
cggctctgtc caccctcaca aataaaatct gcaatcgcct cgcccaaatt caagacaata      840
agattctcca agttgtggat gggagcataa aggataagga gctagaacag gatatgcagg      900
cgttggtgaa gttagtgctt caagaaaatg gcggcgccgt agacagaaac atcagacaca      960 cgttttttgtc ggtttccaag actttctact acgatgccta ccacgacgat gagacgaccg    1020
atcttcatat cttcaaagta ctctttcgac cggttgtatg aaaaatattt taagctcgtc     1080
tgcagtccac gtagataatt attttaaaat aaaggataaa ttaacgagaa acgacgccat     1140
tttaaaataa tatgttaaga atggaccccta aataagagcg tcgaaacatg cattgggata    1200
taatttatta attgttacac catttcggaa taaaatgatg ttatttctttt tcatatgta    1260 aaaaaaaaaa a                                                            1271
```

<210> SEQ ID NO 16
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 16
catggcatct tcaaccccag ctttatctca tc                                      32

<210> SEQ ID NO 17
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 17
gtggtcggat atcacccatc tttcttgaag tcg                                     33

<210> SEQ ID NO 18
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 18
cattggagat gcagactcga ccgattgacc                                         30

<210> SEQ ID NO 19
<211> LENGTH: 1449
<212> TYPE: DNA
<213> ORGANISM: Salvia sclarea

<400> SEQUENCE: 19

```
caaaattctc ttccattttt aagataaatag taatattcta attttccctc caaaaactcg      60
tgggaaattg aaaaatagaa aataaagatg acttctgtaa atttgagcag agcaccagca     120
gcgattatcc ggcgcaggct gcagctacag ccggaatttc atgccgagtg ttcatggctg     180
aaaagcagca gcaaacacgc gcccttgacc ttgagttgcc aaatccgtcc taagcaactc     240
tcccaaatag ctgaattgag agtaacaagc ctggatgcgt cgcaagcgag tgaaaaagac     300
atttcccttg ttcaaactcc gcataaggtt gaggttaatg aaaagatcga ggagtcaatc     360
gagtacgtcc aaaatctgtt gatgacgtcg ggcgacgggc gaataagcgt gtcaccctat     420
gacacggcag tgatcgccct gatcaaggac ttgaaagggc gcgacgcccc gcagtttccg     480
tcatgtctcg agtggatcgc gcaccaccaa ctggctgatg gctcatgggg cgacgaattc     540 ttctgtatt atgatcggat tctaaataca ttggcatgtg tcgtagcctt gaaatcatgg     600
aaccttcact ctgatattat tgaaaaagga gtgacgtaca tcaaggagaa tgtgcataaa     660
cttaaaggtg caaatgttga gcacaggaca gcggggttcg aacttgtggt tcctactttt     720
atgcaaatgg ccacagattt gggcatccaa gatctgccct atgatcatcc cctcatcaag     780
gagattgctg acacaaaaca acaaagattg aaagagatac caaggatttt ggttaccaa      840 atgccaacga atttactgta cagtttagaa gggttaggag atttggagtg ggaaaggcta     900
ctgaaactgc agtcgggcaa tggctccttc tcacttcgc gtcgtccac cgccgccgtc       960 ttgatgcata ccaaagatga aaatgttttg aaatacatcg aaaacgccct caagaattgc    1020
gacggaggag caccacatac ttatccagtc gatatcttct caagactttg ggcaatcgat    1080
aggctacaac gcctaggaat ttctcgtttc ttccagcacg agatcaagta tttcttagat    1140
cacatcgaaa gcgtttggga ggagaccgga gttttcagtg aagatatac gaaatttagc     1200 gatattgatg acacgtccat gggcgttagg cttctcaaaa tgcacggata cgacgtcgat    1260
ccaaatgtac taaacatttt caagcaacaa gatggtaaat tttcctgcta cattggtcaa    1320
tcggtcgagt ctgcatctcc aatgtacaat ctttataggg ctgctcaact aagatttcca    1380
ggagaagaag ttcttgaaga agccactaaa tttgccttta acttcttgca agaaatgcta    1440
gtcaaagat                                                            1449

<210> SEQ ID NO 20
<211> LENGTH: 2655
<212> TYPE: DNA
<213> ORGANISM: Salvia sclarea

<400> SEQUENCE: 20
caaaattctc ttccattttt aagataaatag taatattcta attttccctc caaaaactcg      60
tgggaaattg aaaaatagaa aataaagatg acttctgtaa atttgagcag agcaccagca     120
gcgattatcc ggcgcaggct gcagctacag ccggaatttc atgccgagtg ttcatggctg     180
aaaagcagca gcaaacacgc gcccttgacc ttgagttgcc aaatccgtcc taagcaactc     240
tcccaaatag ctgaattgag agtaacaagc ctggatgcgt cgcaagcgag tgaaaaagac     300
atttcccttg ttcaaactcc gcataaggtt gaggttaatg aaaagatcga ggagtcaatc     360
gagtacgtcc aaaatctgtt gatgacgtcg ggcgacgggc gaataagcgt gtcaccctat     420
gacacggcag tgatcgccct gatcaaggac ttgaaagggc gcgacgcccc gcagtttccg     480
tcatgtctcg agtggatcgc gcaccaccaa ctggctgatg gctcatgggg cgacgaattc     540 ttctgtatt atgatcggat tctaaataca ttggcatgtg tcgtagcctt gaaatcatgg      600
aaccttcact ctgatattat tgaaaaagga gtgacgtaca tcaaggagaa tgtgcataaa     660
```

-continued

```
cttaaaggtg caaatgttga gcacaggaca gcggggttcg aacttgtggt tcctactttt    720
atgcaaatgg ccacagattt gggcatccaa gatctgccct atgatcatcc cctcatcaag    780
gagattgctg acacaaaaca acaaagattg aaagagatac ccaaggattt ggtttaccaa    840
atgccaacga atttactgta cagtttagaa gggttaggag atttggagtg gaaaggcta    900
ctgaaactgc agtcgggcaa tggctccttc ctcacttcgc cgtcgtccac cgccgccgtc    960
ttgatgcata ccaaagatga aaatgtttg aaatacatcg aaaacgccct caagaattgc   1020
gacggaggag caccacatac ttatccagtc gatatcttct caagactttg gcaatcgat   1080
aggctacaac gcctaggaat ttctcgtttc ttccagcacg agatcaagta tttcttagat   1140
cacatcgaaa gcgtttggga ggagaccgga gttttcagtg aagatatac gaaatttagc   1200
gatattgatg acacgtccat gggcgttagg cttctcaaaa tgcacggata cgacgtcgat   1260
ccaaatgtac taaaacattt caagcaacaa gatggtaaat tttcctgcta cattggtcaa   1320
tcggtcgagt ctgcatctcc aatgtacaat ctttataggg ctgctcaact aagatttcca   1380
ggagaagaag ttcttgaaga agccactaaa tttgccttta acttcttgca agaaatgcta   1440
gtcaaagatc gacttcaaga agatgggtg atatccgacc acttatttga tgagataaag   1500
ctggggttga agatgccatg gtacgccact ctaccccgag tcgaggctgc atattatcta   1560
gaccattatg ctggttctgg tgatgtatgg attggcaaga gttctacag gatgccagaa   1620
atcagcaatg atacatacaa ggagcttgcg atattggatt caacagatg ccaaacacaa   1680
catcagttgg agtggatcca tatgcaggaa tggtacgaca gatgcagcct tagcgaattc   1740
gggataagca aaagagagtt gcttcgctct tactttctgg ccgcagcaac catattcgaa   1800
ccggagagaa ctcaagagag gcttctgtgg gccaaaacca gaattctttc taagatgatc   1860
acttcatttg tcaacattag tggaacaaca ctatctttgg actacaattt caatggcctc   1920
gatgaaataa ttagtagtgc caatgaagat caaggactgg ctgggactct gctggcaacc   1980
ttccatcaac ttctagacgg attcgatata tacactctcc atcaactcaa acatgtttgg   2040
agccaatggt tcatgaaagt gcagcaagga gagggaagcg gcgggaaga cgcggtgctc   2100
ctagcgaaca cgctcaacat ctgcgccggc ctcaacgaag acgtgttgtc caacaatgaa   2160
tacacggctc tgtccaccct cacaaataaa atctgcaatc gcctcgccca aattcaagac   2220
aataagattc tccaagttgt ggatgggagc ataaggata aggagctaga acaggatatg   2280
caggcgttgg tgaagttagt gcttcaagaa aatggcggcg ccgtagacag aaacatcaga   2340
cacacgtttt tgtcggtttc caagactttc tactacgatg cctaccacga cgatgagacg   2400
accgatcttc atatcttcaa agtactcttt cgaccggttg tatgaaaaat attttaagct   2460
cgtctgcagt ccacgtagat aattatttta aaataaagga taaattaacg agaaacgacg   2520
ccatttttaaa ataatatgtt aagaatggac cctaaataag agcgtcgaaa catgcattgg   2580
gatataattt attaattgtt acaccatttc ggaataaaat gatgttattt cttttcata   2640
tgtaaaaaaa aaaaa                                                    2655
```

<210> SEQ ID NO 21
<211> LENGTH: 785
<212> TYPE: PRT
<213> ORGANISM: Salvia sclarea

<400> SEQUENCE: 21

```
Met Thr Ser Val Asn Leu Ser Arg Ala Pro Ala Ala Ile Ile Arg Arg
1               5                   10                  15

Arg Leu Gln Leu Gln Pro Glu Phe His Ala Glu Cys Ser Trp Leu Lys
```

```
                 20                  25                  30
Ser Ser Ser Lys His Ala Pro Leu Thr Leu Ser Cys Gln Ile Arg Pro
        35                  40                  45

Lys Gln Leu Ser Gln Ile Ala Glu Leu Arg Val Thr Ser Leu Asp Ala
50                  55                  60

Ser Gln Ala Ser Glu Lys Asp Ile Ser Leu Val Gln Thr Pro His Lys
65                  70                  75                  80

Val Glu Val Asn Glu Lys Ile Glu Glu Ser Ile Glu Tyr Val Gln Asn
                85                  90                  95

Leu Leu Met Thr Ser Gly Asp Gly Arg Ile Ser Val Ser Pro Tyr Asp
                100                 105                 110

Thr Ala Val Ile Ala Leu Ile Lys Asp Leu Lys Gly Arg Asp Ala Pro
            115                 120                 125

Gln Phe Pro Ser Cys Leu Glu Trp Ile Ala His His Gln Leu Ala Asp
        130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu His Ser Asp
                165                 170                 175

Ile Ile Glu Lys Gly Val Thr Tyr Ile Lys Glu Asn Val His Lys Leu
                180                 185                 190

Lys Gly Ala Asn Val Glu His Arg Thr Ala Gly Phe Glu Leu Val Val
            195                 200                 205

Pro Thr Phe Met Gln Met Ala Thr Asp Leu Gly Ile Gln Asp Leu Pro
        210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
                260                 265                 270

Lys Leu Gln Ser Gly Asn Gly Ser Phe Leu Thr Ser Pro Ser Ser Thr
            275                 280                 285

Ala Ala Val Leu Met His Thr Lys Asp Glu Lys Cys Leu Lys Tyr Ile
        290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335

Gly Ile Ser Arg Phe Phe Gln His Glu Ile Lys Tyr Phe Leu Asp His
            340                 345                 350

Ile Glu Ser Val Trp Glu Glu Thr Gly Val Phe Ser Gly Arg Tyr Thr
        355                 360                 365

Lys Phe Ser Asp Ile Asp Asp Thr Ser Met Gly Val Arg Leu Leu Lys
        370                 375                 380

Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
                405                 410                 415

Ser Pro Met Tyr Asn Leu Tyr Arg Ala Ala Gln Leu Arg Phe Pro Gly
            420                 425                 430

Glu Glu Val Leu Glu Glu Ala Thr Lys Phe Ala Phe Asn Phe Leu Gln
        435                 440                 445
```

Glu Met Leu Val Lys Asp Arg Leu Gln Glu Arg Trp Val Ile Ser Asp
450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
                500                 505                 510

Ser Asn Asp Thr Tyr Lys Glu Leu Ala Ile Leu Asp Phe Asn Arg Cys
            515                 520                 525

Gln Thr Gln His Gln Leu Glu Trp Ile His Met Gln Glu Trp Tyr Asp
530                 535                 540

Arg Cys Ser Leu Ser Glu Phe Gly Ile Ser Lys Arg Glu Leu Leu Arg
545                 550                 555                 560

Ser Tyr Phe Leu Ala Ala Ala Thr Ile Phe Glu Pro Glu Arg Thr Gln
                565                 570                 575

Glu Arg Leu Leu Trp Ala Lys Thr Arg Ile Leu Ser Lys Met Ile Thr
                580                 585                 590

Ser Phe Val Asn Ile Ser Gly Thr Thr Leu Ser Leu Asp Tyr Asn Phe
            595                 600                 605

Asn Gly Leu Asp Glu Ile Ile Ser Ser Ala Asn Glu Asp Gln Gly Leu
610                 615                 620

Ala Gly Thr Leu Leu Ala Thr Phe His Gln Leu Leu Asp Gly Phe Asp
625                 630                 635                 640

Ile Tyr Thr Leu His Gln Leu Lys His Val Trp Ser Gln Trp Phe Met
                645                 650                 655

Lys Val Gln Gln Gly Glu Gly Ser Gly Gly Glu Asp Ala Val Leu Leu
                660                 665                 670

Ala Asn Thr Leu Asn Ile Cys Ala Gly Leu Asn Glu Asp Val Leu Ser
            675                 680                 685

Asn Asn Glu Tyr Thr Ala Leu Ser Thr Leu Thr Asn Lys Ile Cys Asn
690                 695                 700

Arg Leu Ala Gln Ile Gln Asp Asn Lys Ile Leu Gln Val Val Asp Gly
705                 710                 715                 720

Ser Ile Lys Asp Lys Glu Leu Glu Gln Asp Met Gln Ala Leu Val Lys
                725                 730                 735

Leu Val Leu Gln Glu Asn Gly Gly Ala Val Asp Arg Asn Ile Arg His
                740                 745                 750

Thr Phe Leu Ser Val Ser Lys Thr Phe Tyr Tyr Asp Ala Tyr His Asp
            755                 760                 765

Asp Glu Thr Thr Asp Leu His Ile Phe Lys Val Leu Phe Arg Pro Val
770                 775                 780

Val
785

<210> SEQ ID NO 22
<211> LENGTH: 38
<212> TYPE: DNA
<213> ORGANISM: Artificial sequence
<220> FEATURE:
<223> OTHER INFORMATION: Oligonucleotide primer

<400> SEQUENCE: 22
tactgacata tgacttctgt aaatttgagc agagcacc                                38

<210> SEQ ID NO 23

```
<211> LENGTH: 36
<212> TYPE: DNA
<213> ORGANISM: Artificial sequence
<220> FEATURE:
<223> OTHER INFORMATION: Oligonucleotide primer

<400> SEQUENCE: 23
ttggtacctc atacaaccgg tcgaaagagt actttg                                36

<210> SEQ ID NO 24
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 24
gttggagtgg atccacatgc aggaatggta c                                     31

<210> SEQ ID NO 25
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 25
gtaccattcc tgcatctgga tccactccaa c                                     31

<210> SEQ ID NO 26
<211> LENGTH: 805
<212> TYPE: PRT
<213> ORGANISM: Salvia sclarea

<400> SEQUENCE: 26
```

Met Gly Ser Ser His His His His His His Ser Ser Gly Leu Val Pro
1               5                   10                  15

Arg Gly Ser His Met Thr Ser Val Asn Leu Ser Arg Ala Pro Ala Ala
            20                  25                  30

Ile Thr Arg Arg Leu Gln Leu Gln Pro Glu Phe His Ala Glu Cys
        35                  40                  45

Ser Trp Leu Lys Ser Ser Lys His Ala Pro Leu Thr Leu Ser Cys
    50                  55                  60

Gln Ile Arg Pro Lys Gln Leu Ser Gln Ile Ala Glu Leu Arg Val Thr
65                  70                  75                  80

Ser Leu Asp Ala Ser Gln Ala Ser Glu Lys Asp Ile Ser Leu Val Gln
                85                  90                  95

Thr Pro His Lys Val Glu Val Asn Glu Lys Ile Glu Glu Ser Ile Glu
            100                 105                 110

Tyr Val Gln Asn Leu Leu Met Thr Ser Gly Asp Gly Arg Ile Ser Val
        115                 120                 125

Ser Pro Tyr Asp Thr Ala Val Ile Ala Leu Ile Lys Asp Leu Lys Gly
    130                 135                 140

Arg Asp Ala Pro Gln Phe Pro Ser Cys Leu Glu Trp Ile Ala His His
145                 150                 155                 160

Gln Leu Ala Asp Gly Ser Trp Gly Asp Glu Phe Phe Cys Ile Tyr Asp
                165                 170                 175

Arg Ile Leu Asn Thr Leu Ala Cys Val Val Ala Leu Lys Ser Trp Asn
            180                 185                 190

Leu His Ser Asp Ile Ile Glu Lys Gly Val Thr Tyr Ile Lys Glu Asn
        195                 200                 205

```
Val His Lys Leu Lys Gly Ala Asn Val Glu His Arg Thr Ala Gly Phe
    210                 215                 220

Glu Leu Val Val Pro Thr Phe Met Gln Met Ala Thr Asp Leu Gly Ile
225                 230                 235                 240

Gln Asp Leu Pro Tyr Asp His Pro Leu Ile Lys Glu Ile Ala Asp Thr
                245                 250                 255

Lys Gln Gln Arg Leu Lys Glu Ile Pro Lys Asp Leu Val Tyr Gln Met
            260                 265                 270

Pro Thr Asn Leu Leu Tyr Ser Leu Glu Gly Leu Gly Asp Leu Glu Trp
        275                 280                 285

Glu Arg Leu Leu Lys Leu Gln Ser Gly Asn Gly Ser Phe Leu Thr Ser
    290                 295                 300

Pro Ser Ser Thr Ala Ala Val Leu Met His Thr Lys Asp Glu Lys Cys
305                 310                 315                 320

Leu Lys Tyr Ile Glu Asn Ala Leu Lys Asn Cys Asp Gly Gly Ala Pro
                325                 330                 335

His Thr Tyr Pro Val Asp Ile Phe Ser Arg Leu Trp Ala Ile Asp Arg
            340                 345                 350

Leu Gln Arg Leu Gly Ile Ser Arg Phe Phe Gln His Glu Ile Lys Tyr
        355                 360                 365

Phe Leu Asp His Ile Glu Ser Val Trp Glu Glu Thr Gly Val Phe Ser
370                 375                 380

Gly Arg Tyr Thr Lys Phe Ser Asp Ile Asp Thr Ser Met Gly Val
385                 390                 395                 400

Arg Leu Leu Lys Met His Gly Tyr Asp Val Asp Pro Asn Val Leu Lys
                405                 410                 415

His Phe Lys Gln Gln Asp Gly Lys Phe Ser Cys Tyr Ile Gly Gln Ser
            420                 425                 430

Val Glu Ser Ala Ser Pro Met Tyr Asn Leu Tyr Arg Ala Ala Gln Leu
        435                 440                 445

Arg Phe Pro Gly Glu Glu Val Leu Glu Glu Ala Thr Lys Phe Ala Phe
    450                 455                 460

Asn Phe Leu Gln Glu Met Leu Val Lys Asp Arg Leu Gln Glu Arg Trp
465                 470                 475                 480

Val Ile Ser Asp His Leu Phe Asp Glu Ile Lys Leu Gly Leu Lys Met
                485                 490                 495

Pro Trp Tyr Ala Thr Leu Pro Arg Val Glu Ala Ala Tyr Tyr Leu Asp
            500                 505                 510

His Tyr Ala Gly Ser Gly Asp Val Trp Ile Gly Lys Ser Phe Tyr Arg
        515                 520                 525

Met Pro Glu Ile Ser Asn Asp Thr Tyr Lys Glu Leu Ala Ile Leu Asp
    530                 535                 540

Phe Asn Arg Cys Gln Thr Gln His Leu Glu Trp Ile His Met Gln
545                 550                 555                 560

Glu Trp Tyr Asp Arg Cys Ser Leu Ser Glu Phe Gly Ile Ser Lys Arg
                565                 570                 575

Glu Leu Leu Arg Ser Tyr Phe Leu Ala Ala Ala Thr Ile Phe Glu Pro
            580                 585                 590

Glu Arg Thr Gln Glu Arg Leu Leu Trp Ala Lys Thr Arg Ile Leu Ser
        595                 600                 605

Lys Met Ile Thr Ser Phe Val Asn Ile Ser Gly Thr Thr Leu Ser Leu
    610                 615                 620

Asp Tyr Asn Phe Asn Gly Leu Asp Glu Ile Ile Ser Ser Ala Asn Glu
```

```
                625                 630                 635                 640
Asp Gln Gly Leu Ala Gly Thr Leu Leu Ala Thr Phe His Gln Leu Leu
                    645                 650                 655

Asp Gly Phe Asp Ile Tyr Thr Leu His Gln Leu Lys His Val Trp Ser
                    660                 665                 670

Gln Trp Phe Met Lys Val Gln Gln Gly Glu Ser Gly Gly Glu Asp
                    675                 680                 685

Ala Val Leu Leu Ala Asn Thr Leu Asn Ile Cys Ala Gly Leu Asn Glu
                    690                 695                 700

Asp Val Leu Ser Asn Asn Glu Tyr Thr Ala Leu Ser Thr Leu Thr Asn
705                 710                 715                 720

Lys Ile Cys Asn Arg Leu Ala Gln Ile Gln Asp Asn Lys Ile Leu Gln
                    725                 730                 735

Val Val Asp Gly Ser Ile Lys Asp Lys Glu Leu Glu Gln Asp Met Gln
                    740                 745                 750

Ala Leu Val Lys Leu Val Leu Gln Glu Asn Gly Gly Ala Val Asp Arg
                    755                 760                 765

Asn Ile Arg His Thr Phe Leu Ser Val Ser Lys Thr Phe Tyr Tyr Asp
                    770                 775                 780

Ala Tyr His Asp Asp Glu Thr Thr Asp Leu His Ile Phe Lys Val Leu
785                 790                 795                 800

Phe Arg Pro Val Val
                805

<210> SEQ ID NO 27
<211> LENGTH: 804
<212> TYPE: PRT
<213> ORGANISM: Salvia sclarea

<400> SEQUENCE: 27

Met Gly Ser Ser His His His His His His Ser Ser Gly Leu Val Pro
1               5                   10                  15

Arg Gly Ser His Met Thr Ser Val Asn Leu Ser Arg Ala Pro Ala Ala
                20                  25                  30

Ile Ile Arg Arg Arg Leu Gln Leu Gln Pro Glu Phe His Ala Glu Cys
            35                  40                  45

Ser Trp Leu Lys Ser Ser Lys His Ala Pro Phe Thr Leu Ser Cys
        50                  55                  60

Gln Ile Arg Pro Lys Gln Leu Ser Gln Ile Ala Glu Leu Arg Val Thr
65                  70                  75                  80

Ser Leu Asp Ala Ser Gln Ala Ser Glu Lys Asp Ile Ser Leu Val Gln
                85                  90                  95

Thr Pro His Lys Val Glu Val Asn Glu Lys Ile Glu Glu Ser Ile Glu
                100                 105                 110

Tyr Val Gln Asn Leu Leu Met Thr Ser Gly Asp Gly Arg Ile Ser Val
            115                 120                 125

Ser Pro Tyr Asp Thr Ala Val Ile Ala Leu Ile Lys Asp Leu Lys Gly
        130                 135                 140

Arg Asp Ala Pro Gln Phe Pro Ser Cys Leu Glu Trp Ile Ala His His
145                 150                 155                 160

Gln Leu Ala Asp Gly Ser Trp Gly Asp Glu Phe Phe Cys Ile Tyr Asp
                165                 170                 175

Arg Ile Leu Asn Thr Leu Ala Cys Val Val Ala Leu Lys Ser Trp Asn
            180                 185                 190

Leu Gln Ser Asp Ile Ile Glu Lys Gly Val Thr Tyr Ile Lys Glu Asn
```

-continued

```
            195                 200                 205
Val His Lys Leu Lys Gly Ala Asn Val Glu His Arg Thr Ala Gly Phe
210                 215                 220

Glu Leu Val Val Pro Thr Phe Met Gln Met Ala Thr Asp Leu Gly Ile
225                 230                 235                 240

Gln Gly Leu Pro Tyr Asp His Pro Leu Ile Lys Glu Ile Ala Asp Thr
                245                 250                 255

Lys Gln Gln Arg Leu Lys Glu Ile Pro Lys Asp Leu Val Tyr Gln Met
                260                 265                 270

Pro Thr Asn Leu Leu Tyr Ser Leu Glu Gly Leu Gly Asp Leu Glu Trp
                275                 280                 285

Glu Arg Leu Leu Lys Leu Gln Ser Gly Asn Gly Ser Phe Leu Thr Ser
290                 295                 300

Pro Ser Ser Thr Ala Ala Val Leu Met His Thr Lys Asp Glu Lys Cys
305                 310                 315                 320

Leu Lys Tyr Ile Glu Asn Ala Leu Lys Asn Cys Asp Gly Gly Ala Pro
                325                 330                 335

His Thr Tyr Pro Val Asp Ile Phe Ser Arg Leu Trp Ala Ile Asp Arg
                340                 345                 350

Leu Gln Arg Leu Gly Ile Ser Arg Phe Phe Gln His Glu Ile Lys Tyr
                355                 360                 365

Phe Leu Asp His Ile Glu Ser Val Trp Glu Glu Thr Gly Val Phe Ser
                370                 375                 380

Gly Arg Tyr Thr Lys Phe Ser Asp Ile Asp Asp Thr Ser Met Gly Val
385                 390                 395                 400

Arg Leu Leu Lys Met His Gly Tyr Asp Val Asp Pro Asn Val Leu Lys
                405                 410                 415

His Phe Lys Gln Gln Asp Gly Lys Phe Ser Cys Tyr Ile Gly Gln Ser
                420                 425                 430

Val Glu Ser Ala Ser Pro Met Tyr Asn Leu Tyr Arg Ala Ala Gln Leu
                435                 440                 445

Arg Phe Pro Gly Glu Glu Val Leu Glu Glu Ala Thr Lys Phe Ala Phe
450                 455                 460

Asn Phe Leu Gln Glu Met Leu Val Lys Asp Arg Leu Gln Glu Arg Trp
465                 470                 475                 480

Val Ile Ser Asp His Leu Phe Asp Glu Ile Lys Leu Gly Leu Lys Met
                485                 490                 495

Pro Trp Tyr Ala Thr Leu Pro Arg Val Glu Ala Ala Tyr Tyr Leu Asp
                500                 505                 510

His Tyr Ala Gly Ser Gly Asp Val Trp Ile Gly Lys Ser Phe Tyr Arg
                515                 520                 525

Met Pro Glu Ile Ser Asn Asp Thr Tyr Lys Glu Leu Ala Ile Leu Asp
530                 535                 540

Phe Asn Arg Cys Gln Thr Gln His Gln Leu Glu Trp Ile Gln Met Gln
545                 550                 555                 560

Glu Trp Tyr Asp Arg Cys Ser Leu Ser Glu Phe Gly Ile Ser Lys Arg
                565                 570                 575

Glu Leu Leu Arg Ser Tyr Phe Leu Ala Ala Ala Thr Ile Phe Glu Pro
                580                 585                 590

Glu Arg Thr Gln Glu Arg Leu Leu Trp Ala Lys Thr Arg Ile Leu Ser
                595                 600                 605

Lys Met Ile Thr Ser Phe Val Asn Ile Ser Gly Thr Thr Leu Ser Leu
610                 615                 620
```

| | | | | | | | | | | | | | | |
|---|---|---|---|---|---|---|---|---|---|---|---|---|---|---|
|Asp|Tyr|Asn|Phe|Asn|Gly|Leu|Asp|Glu|Ile|Ile|Ser|Ala|Asn|Glu|Asp|
|625| | | | |630| | | | |635| | | | |640|

| | | | | | | | | | | |
|---|---|---|---|---|---|---|---|---|---|---|
|Gln|Gly|Leu|Ala|Gly|Thr|Leu|Leu|Ala|Thr|Phe|His|Gln|Leu|Leu|Asp|
| | | | | |645| | | | |650| | | | |655|

Gly Phe Asp Ile Tyr Thr Leu His Gln Leu Lys His Val Trp Ser Gln
          660                 665                 670

Trp Phe Met Lys Val Gln Gln Gly Glu Gly Ser Gly Gly Glu Asp Ala
        675                 680                 685

Val Leu Leu Ala Asn Thr Leu Asn Ile Cys Ala Gly Leu Asn Glu Asp
    690                 695                 700

Val Leu Ser Asn Asn Glu Tyr Thr Ala Leu Ser Thr Leu Thr Asn Lys
705                 710                 715                 720

Ile Cys Asn Arg Leu Ala Gln Ile Gln Asp Asn Lys Ile Leu Gln Val
                725                 730                 735

Val Asp Gly Ser Ile Lys Asp Lys Glu Leu Glu Gln Asp Met Gln Ala
            740                 745                 750

Leu Val Lys Leu Val Leu Gln Glu Asn Gly Gly Ala Val Asp Arg Asn
        755                 760                 765

Ile Arg His Thr Phe Leu Ser Val Ser Lys Thr Phe Tyr Tyr Asp Ala
770                 775                 780

Tyr His Asp Asp Glu Thr Thr Asp Leu His Ile Phe Lys Val Leu Phe
785                 790                 795                 800

Arg Pro Val Val

```
<210> SEQ ID NO 28
<211> LENGTH: 2310
<212> TYPE: DNA
<213> ORGANISM: Salvia sclarea

<400> SEQUENCE: 28
atgctgcagc tacagccgga atttcatgcc gagtgttcat ggctgaaaag cagcagcaaa        60
cacgcgccct tgaccttgag ttgccaaatc cgtcctaagc aactctccca aatagctgaa       120
ttgagagtaa caagcctgga tgcgtcgcaa gcgagtgaaa aagacatttc ccttgttcaa       180
actccgcata aggttgaggt taatgaaaag atcgaggagt caatcgagta cgtccaaaat       240
ctgttgatga cgtcgggcga cgggcgaata agcgtgtcac cctatgacac ggcagtgatc       300
gccctgatca aggacttgaa agggcgcgac gccccgcagt ttccgtcatg tctcgagtgg       360
atcgcgcacc accaactggc tgatggctca tggggcgacg aattcttctg tatttatgat       420
cggattctaa atacattggc atgtgtcgta gccttgaaat catggaaccct tcactctgat       480 attattgaaa aggagtgac gtacatcaag gagaatgtgc ataaacttaa aggtgcaaat       540
gttgagcaca ggacagcggg gttcgaactt gtggttccta ctttatgca atggccaca       600 gatttgggca tccaagatct gccctatgat catcccctca tcaaggagat tgctgacaca       660
aaacaacaaa gattgaaaga gatacccaag gatttggttt accaaatgcc aacgaattta       720
ctgtacagtt tagaagggtt aggagatttg gagtgggaaa ggctactgaa actgcagtcg       780
ggcaatggct ccttcctcac ttcgccgtcg tccaccgccg ccgtcttgat gcataccaaa       840
gatgaaaaat gtttgaaata catcgaaaac gccctcaaga attgcgacgg aggagcacca       900
catacttatc cagtcgatat cttctcaaga ctttgggcaa tcgataggct acaacgccta       960
ggaatttctc gtttcttcca gcacgagatc aagtatttct tagatcacat cgaaagcgtt      1020
tgggaggaga ccggagtttt cagtggaaga tatacgaaat ttagcgatat tgatgacacg      1080
tccatgggcg ttaggcttct caaaatgcac ggatacgacg tcgatccaaa tgtactaaaa      1140
```

```
catttcaagc aacaagatgg taaattttcc tgctacattg gtcaatcggt cgagtctgca   1200
tctccaatgt acaatcttta tagggctgct caactaagat tccaggaga agaagttctt   1260 gaagaagcca ctaaatttgc ctttaacttc ttgcaagaaa tgctagtcaa agatcgactt   1320
caagaaagat gggtgatatc cgaccactta tttgatgaga taaagctggg gttgaagatg   1380
ccatggtacg ccactctacc ccgagtcgag gctgcatatt atctagacca ttatgctggt   1440
tctggtgatg tatggattgg caagagtttc tacaggatgc agaaatcag caatgataca   1500 tacaaggagc ttgcgatatt ggatttcaac agatgccaaa cacaacatca gttggagtgg   1560
atccacatgc aggaatggta cgacagatgc agccttagcg aattcgggat aagcaaaaga   1620
gagttgcttc gctcttactt tctggccgca gcaaccatat tcgaaccgga gagaactcaa   1680
gagaggcttc tgtgggccaa aaccagaatt ctttctaaga tgatcacttc atttgtcaac   1740
attagtggaa caacactatc tttggactac aatttcaatg gcctcgatga ataattagt    1800 agtgccaatg aagatcaagg actggctggg actctgctgg caaccttcca tcaacttcta   1860
gacggattcg atatatacac tctccatcaa ctcaaacatg tttggagcca atggttcatg   1920
aaagtgcagc aaggagaggg aagcggcggg aagacgcgg tgctcctagc gaacacgctc    1980
aacatctgcg ccggcctcaa cgaagacgtg ttgtccaaca atgaatacac ggctctgtcc   2040
accctcacaa ataaaatctg caatcgcctc gcccaaattc aagacaataa gattctccaa   2100
gttgtggatg ggagcataaa ggataaggag ctagaacagg atatgcaggc gttggtgaag   2160
ttagtgcttc aagaaaatgg cggcgccgta gacagaaaca tcagacacac gttttttgtcg  2220 gtttccaaga ctttctacta cgatgcctac cacgacgatg agacgaccga tcttcatatc   2280
ttcaaagtac tctttcgacc ggttgtatga                                    2310

<210> SEQ ID NO 29
<211> LENGTH: 2253
<212> TYPE: DNA
<213> ORGANISM: Salvia sclarea

<400> SEQUENCE: 29
atgcacgcgc ccttgacctt gagttgccaa atccgtccta agcaactctc ccaaatagct    60
gaattgagag taacaagcct ggatgcgtcg caagcgagtg aaaaagacat ttcccttgtt   120
caaactccgc ataaggttga ggttaatgaa aagatcgagg agtcaatcga gtacgtccaa   180
aatctgttga tgacgtcggg cgacgggcga ataagcgtgt caccctatga cacggcagtg   240
atcgccctga tcaaggactt gaaagggcgc gacgccccgc agtttccgtc atgtctcgag   300
tggatcgcgc accaccaact ggctgatggc tcatggggcg acgaattctt ctgtatttat   360
gatcggattc taaatacatt ggcatgtgtc gtagccttga aatcatggaa ccttcactct   420
gatattattg aaaaggagt gacgtacatc aaggagaatg tgcataaact taaaggtgca   480
aatgttgagc acaggacagc ggggttcgaa cttgtggttc ctacttttat gcaaatggcc   540
acagatttgg gcatccaaga tctgccctat gatcatcccc tcatcaagga gattgctgac   600
acaaaacaac aaagattgaa agagatacc aaggatttgg tttaccaaat gccaacgaat   660
ttactgtaca gtttagaagg gttaggagat ttggagtggg aaaggctact gaaactgcag   720
tcgggcaatg gctccttcct cacttcgccg tcgtccaccg ccgccgtctt gatgcatacc   780
aaagatgaaa atgtttgaa atacatcgaa aacgccctca gaattgcga cggaggagca   840 ccacatactt atccagtcga tatcttctca agactttggg caatcgatag ctacaacgc    900 ctaggaattt ctcgtttctt ccagcacgag atcaagtatt tcttagatca catcgaaagc   960
```

```
gtttgggagg agaccggagt tttcagtgga agatatacga aatttagcga tattgatgac      1020
acgtccatgg gcgttaggct tctcaaaatg cacggatacg acgtcgatcc aaatgtacta      1080
aaacatttca agcaacaaga tggtaaattt tcctgctaca ttggtcaatc ggtcgagtct      1140
gcatctccaa tgtacaatct ttatagggct gctcaactaa gatttccagg agaagaagtt      1200
cttgaagaag ccactaaatt tgcctttaac ttcttgcaag aaatgctagt caaagatcga      1260
cttcaagaaa gatgggtgat atccgaccac ttatttgatg agataaagct ggggttgaag      1320
atgccatggt acgccactct accccgagtc gaggctgcat attatctaga ccattatgct      1380
ggttctggtg atgtatggat tggcaagagt ttctacagga tgccagaaat cagcaatgat      1440
acatacaagg agcttgcgat attggatttc aacagatgcc aaacacaaca tcagttggag      1500
tggatccaca tgcaggaatg gtacgacaga tgcagcctta gcgaattcgg gataagcaaa      1560
agagagttgc ttcgctctta ctttctggcc gcagcaacca tattcgaacc ggagagaact      1620
caagagaggc ttctgtgggc caaaaccaga attctttcta agatgatcac ttcatttgtc      1680
aacattagtg gaacaacact atctttggac tacaatttca atggcctcga tgaaataatt      1740
agtagtgcca atgaagatca aggactggct gggactctgc tggcaaccct tccatcaactt     1800
ctagacggat tcgatatata cactctccat caactcaaac atgtttggag ccaatggttc      1860
atgaaagtgc agcaaggaga gggaagcggc ggggaagacg cggtgctcct agcgaacacg      1920
ctcaacatct gcgccggcct caacgaagac gtgttgtcca acaatgaata cacggctctg      1980
tccaccctca caaataaaat ctgcaatcgc ctcgcccaaa ttcaagacaa taagattctc      2040
caagttgtgg atgggagcat aaaggataag gagctagaac aggatatgca ggcgttggtg      2100
aagttagtgc ttcaagaaaa tggcggcgcc gtagacagaa acatcagaca cacgtttttg      2160
tcggtttcca agactttcta ctacgatgcc taccacgacg atgagacgac cgatcttcat      2220
atcttcaaag tactctttcg accggttgta tga                                   2253

<210> SEQ ID NO 30
<211> LENGTH: 2202
<212> TYPE: DNA
<213> ORGANISM: Salvia sclarea

<400> SEQUENCE: 30
atgatagctg aattgagagt aacaagcctg gatgcgtcgc aagcgagtga aaaagacatt       60
tcccttgttc aaactccgca taaggttgag gttaatgaaa agatcgagga gtcaatcgag      120
tacgtccaaa atctgttgat gacgtcgggc gacgggcgaa taagcgtgtc accctatgac      180
acggcagtga tcgccctgat caaggacttg aaagggcgcg acgccccgca gtttccgtca      240
tgtctcgagt ggatcgcgca ccaccaactg gctgatggct catggggcga cgaattcttc      300
tgtatttatg atcggattct aaatacattg gcatgtgtcg tagccttgaa atcatggaac      360
cttcactctg atattattga aaaggagtg acgtacatca aggagaatgt gcataaactt      420
aaaggtgcaa atgttgagca caggacagcg gggttcgaac ttgtggttcc tactttttatg      480
caaatggcca cagatttggg catccaagat ctgccctatg atcatcccct catcaaggag      540
attgctgaca caaaacaaca aagattgaaa gagatacca aggatttggt ttaccaaatg      600
ccaacgaatt tactgtacag tttagaaggg ttaggagatt tggagtggga aaggctactg      660
aaactgcagt cgggcaatgg ctccttcctc acttcgccgt cgtccaccgc cgccgtcttg      720
atgcatacca agatgaaaaa atgtttgaaa tacatcgaaa acgccctcaa gaattgcgac      780
ggaggagcac cacatactta tccagtcgat atcttctcaa gactttgggc aatcgatagg      840
```

```
ctacaacgcc taggaatttc tcgtttcttc cagcacgaga tcaagtattt cttagatcac    900
atcgaaagcg tttgggagga gaccggagtt ttcagtggaa gatatacgaa atttagcgat    960
attgatgaca cgtccatggg cgttaggctt ctcaaaatgc acggatacga cgtcgatcca   1020
aatgtactaa acatttcaa gcaacaagat ggtaaatttt cctgctacat tggtcaatcg   1080
gtcgagtctg catctccaat gtacaatctt tatagggctg ctcaactaag atttccagga   1140
gaagaagttc ttgaagaagc cactaaattt gcctttaact tcttgcaaga aatgctagtc   1200
aaagatcgac ttcaagaaag atgggtgata tccgaccact tatttgatga gataaagctg   1260
gggttgaaga tgccatggta cgccactcta ccccgagtcg aggctgcata ttatctagac   1320
cattatgctg gttctggtga tgtatggatt ggcaagagtt tctacaggat gccagaaatc   1380
agcaatgata catacaagga gcttgcgata ttggatttca acagatgcca aacacaacat   1440
cagttggagt ggatccacat gcaggaatgg tacgacagat gcagccttag cgaattcggg   1500
ataagcaaaa gagagttgct tcgctcttac tttctggccg cagcaaccat attcgaaccg   1560
gagagaactc aagagaggct tctgtgggcc aaaaccagaa ttctttctaa gatgatcact   1620
tcatttgtca acattagtgg aacaacacta tctttggact acaatttcaa tggcctcgat   1680
gaaataatta gtagtgccaa tgaagatcaa ggactggctg ggactctgct ggcaaccttc   1740
catcaacttc tagacggatt cgatatatac actctccatc aactcaaaca tgtttggagc   1800
caatggttca tgaaagtgca gcaaggagag ggaagcggcg gggaagacgc ggtgctccta   1860
gcgaacacgc tcaacatctg cgccggcctc aacgaagacg tgttgtccaa caatgaatac   1920
acggctctgt ccaccctcac aaataaaatc tgcaatcgcc tcgcccaaat tcaagacaat   1980
aagattctcc aagttgtgga tgggagcata aaggataagg agctagaaca ggatatgcag   2040
gcgttggtga agttagtgct tcaagaaaat ggcggcgccg tagacagaaa catcagacac   2100
acgttttgt cggtttccaa gactttctac tacgatgcct accacgacga tgagacgacc   2160
gatcttcata tcttcaaagt actctttcga ccggttgtat ga                     2202
```

<210> SEQ ID NO 31
<211> LENGTH: 2172
<212> TYPE: DNA
<213> ORGANISM: Salvia sclarea

<400> SEQUENCE: 31

```
atggcgtcgc aagcgagtga aaaagacatt tcccttgttc aaactccgca taaggttgag    60
gttaatgaaa agatcgagga gtcaatcgag tacgtccaaa atctgttgat gacgtcgggc   120
gacgggcgaa taagcgtgtc accctatgac acggcagtga tcgccctgat caaggacttg   180
aaagggcgcg acgccccgca gtttccgtca tgtctcgagt ggatcgcgca ccaccaactg   240
gctgatggct catggggcga cgaattcttc tgtatttatg atcggattct aaatacattg   300
gcatgtgtcg tagccttgaa atcatggaac cttcactctg atattattga aaaaggagtg   360
acgtacatca aggagaatgt gcataaactt aaaggtgcaa atgttgagca caggacagcg   420
gggttcgaac ttgtggttcc tactttatg caaatggcca cagatttggg catccaagat   480
ctgccctatg atcatcccct catcaaggag attgctgaca caaaacaaca aagattgaaa   540
gagatacca aggattggt ttaccaaatg ccaacgaatt tactgtacag tttgaaggg    600
ttaggagatt tggagtggga aaggctactg aaactgcagt cgggcaatgg ctccttcctc   660
acttcgccgt cgtccaccgc cgccgtcttg atgcatacca aagatgaaaa atgtttgaaa   720
tacatcgaaa acgccctcaa gaattgcgac ggaggagcac cacatactta tccagtcgat   780
```

```
atcttctcaa gactttgggc aatcgatagg ctacaacgcc taggaatttc tcgtttcttc    840
cagcacgaga tcaagtattt cttagatcac atcgaaagcg tttgggagga gaccggagtt    900
ttcagtggaa gatatacgaa atttagcgat attgatgaca cgtccatggg cgttaggctt    960
ctcaaaatgc acggatacga cgtcgatcca aatgtactaa acatttcaa gcaacaagat    1020 ggtaaatttt cctgctacat tggtcaatcg gtcgagtctg catctccaat gtacaatctt    1080
tatagggctg ctcaactaag atttccagga gaagaagttc ttgaagaagc cactaaattt    1140
gcctttaact tcttgcaaga aatgctagtc aaagatcgac ttcaagaaag atgggtgata    1200
tccgaccact tatttgatga gataaagctg gggttgaaga tgccatggta cgccactcta    1260
ccccgagtcg aggctgcata ttatctagac cattatgctg gttctggtga tgtatggatt    1320
ggcaagagtt tctacaggat gccagaaatc agcaatgata catacaagga gcttgcgata    1380
ttggatttca acagatgcca aacacaacat cagttggagt ggatccacat gcaggaatgg    1440
tacgacagat gcagccttag cgaattcggg ataagcaaaa gagagttgct tcgctcttac    1500
tttctggccg cagcaaccat attcgaaccg gagagaactc aagagaggct tctgtgggcc    1560
aaaaccagaa ttctttctaa gatgatcact tcatttgtca acattagtgg aacaacacta    1620
tctttggact acaatttcaa tggcctcgat gaaataatta gtagtgccaa tgaagatcaa    1680
ggactggctg ggactctgct ggcaaccttc catcaacttc tagacggatt cgatatatac    1740
actctccatc aactcaaaca tgtttggagc caatggttca tgaaagtgca gcaaggagag    1800
ggaagcggcg gggaagacgc ggtgctccta gcgaacacgc tcaacatctg cgccggcctc    1860
aacgaagacg tgttgtccaa caatgaatac acggctctgt ccaccctcac aaataaaatc    1920
tgcaatcgcc tcgcccaaat tcaagacaat aagattctcc aagttgtgga tgggagcata    1980
aaggataagg agctagaaca ggatatgcag gcgttggtga agttagtgct tcaagaaaat    2040
ggcggcgccg tagacagaaa catcagacac acgttttgt cggtttccaa gactttctac    2100
tacgatgcct accacgacga tgagacgacc gatcttcata tcttcaaagt actctttcga    2160
ccggttgtat ga                                                        2172
```

<210> SEQ ID NO 32
<211> LENGTH: 38
<212> TYPE: DNA
<213> ORGANISM: Artificial sequence
<220> FEATURE:
<223> OTHER INFORMATION: Synthetic oligonucleotide primer

<400> SEQUENCE: 32
attacatatg ctgcagctac agccggaatt tcatgccg                             38

<210> SEQ ID NO 33
<211> LENGTH: 38
<212> TYPE: DNA
<213> ORGANISM: Artificial sequence
<220> FEATURE:
<223> OTHER INFORMATION: Synthetic oligonucleotide primer

<400> SEQUENCE: 33
attacatatg gcgcccttga ccttgagttg ccaaatcc                             38

<210> SEQ ID NO 34
<211> LENGTH: 38
<212> TYPE: DNA
<213> ORGANISM: Artificial sequence
<220> FEATURE:
<223> OTHER INFORMATION: Synthetic oligonucleotide primer

<400> SEQUENCE: 34
attacatatg atagctgaat tgagagtaac aagcctgg                              38

<210> SEQ ID NO 35
<211> LENGTH: 38
<212> TYPE: DNA
<213> ORGANISM: Artificial sequence
<220> FEATURE:
<223> OTHER INFORMATION: Synthetic oligonucleotide primer

<400> SEQUENCE: 35
attacatatg atagctgaat tgagagtaac aagcctgg                              38

<210> SEQ ID NO 36
<211> LENGTH: 769
<212> TYPE: PRT
<213> ORGANISM: Salvia sclarea

<400> SEQUENCE: 36

```
Met Leu Gln Leu Gln Pro Glu Phe His Ala Glu Cys Ser Trp Leu Lys
1               5                   10                  15

Ser Ser Ser Lys His Ala Pro Leu Thr Leu Ser Cys Gln Ile Arg Pro
            20                  25                  30

Lys Gln Leu Ser Gln Ile Ala Glu Leu Arg Val Thr Ser Leu Asp Ala
        35                  40                  45

Ser Gln Ala Ser Glu Lys Asp Ile Ser Leu Val Gln Thr Pro His Lys
    50                  55                  60

Val Glu Val Asn Glu Lys Ile Glu Glu Ser Ile Glu Tyr Val Gln Asn
65                  70                  75                  80

Leu Leu Met Thr Ser Gly Asp Gly Arg Ile Ser Val Ser Pro Tyr Asp
                85                  90                  95

Thr Ala Val Ile Ala Leu Ile Lys Asp Leu Lys Gly Arg Asp Ala Pro
            100                 105                 110

Gln Phe Pro Ser Cys Leu Glu Trp Ile Ala His His Gln Leu Ala Asp
        115                 120                 125

Gly Ser Trp Gly Asp Glu Phe Phe Cys Ile Tyr Asp Arg Ile Leu Asn
    130                 135                 140

Thr Leu Ala Cys Val Val Ala Leu Lys Ser Trp Asn Leu His Ser Asp
145                 150                 155                 160

Ile Ile Glu Lys Gly Val Thr Tyr Ile Lys Glu Asn Val His Lys Leu
                165                 170                 175

Lys Gly Ala Asn Val Glu His Arg Thr Ala Gly Phe Glu Leu Val Val
            180                 185                 190

Pro Thr Phe Met Gln Met Ala Thr Asp Leu Gly Ile Gln Asp Leu Pro
        195                 200                 205

Tyr Asp His Pro Leu Ile Lys Glu Ile Ala Asp Thr Lys Gln Gln Arg
    210                 215                 220

Leu Lys Glu Ile Pro Lys Asp Leu Val Tyr Gln Met Pro Thr Asn Leu
225                 230                 235                 240

Leu Tyr Ser Leu Glu Gly Leu Gly Asp Leu Glu Trp Glu Arg Leu Leu
                245                 250                 255

Lys Leu Gln Ser Gly Asn Gly Ser Phe Leu Thr Ser Pro Ser Ser Thr
            260                 265                 270

Ala Ala Val Leu Met His Thr Lys Asp Glu Lys Cys Leu Lys Tyr Ile
        275                 280                 285

Glu Asn Ala Leu Lys Asn Cys Asp Gly Gly Ala Pro His Thr Tyr Pro
```

```
              290                 295                 300
Val Asp Ile Phe Ser Arg Leu Trp Ala Ile Asp Arg Leu Gln Arg Leu
305                 310                 315                 320

Gly Ile Ser Arg Phe Phe Gln His Glu Ile Lys Tyr Phe Leu Asp His
                    325                 330                 335

Ile Glu Ser Val Trp Glu Thr Gly Val Phe Ser Gly Arg Tyr Thr
                340                 345                 350

Lys Phe Ser Asp Ile Asp Asp Thr Ser Met Gly Val Arg Leu Leu Lys
                355                 360                 365

Met His Gly Tyr Asp Val Asp Pro Asn Val Leu Lys His Phe Lys Gln
370                 375                 380

Gln Asp Gly Lys Phe Ser Cys Tyr Ile Gly Gln Ser Val Glu Ser Ala
385                 390                 395                 400

Ser Pro Met Tyr Asn Leu Tyr Arg Ala Ala Gln Leu Arg Phe Pro Gly
                405                 410                 415

Glu Glu Val Leu Glu Glu Ala Thr Lys Phe Ala Phe Asn Phe Leu Gln
                420                 425                 430

Glu Met Leu Val Lys Asp Arg Leu Gln Glu Arg Trp Val Ile Ser Asp
                435                 440                 445

His Leu Phe Asp Glu Ile Lys Leu Gly Leu Lys Met Pro Trp Tyr Ala
450                 455                 460

Thr Leu Pro Arg Val Glu Ala Ala Tyr Tyr Leu Asp His Tyr Ala Gly
465                 470                 475                 480

Ser Gly Asp Val Trp Ile Gly Lys Ser Phe Tyr Arg Met Pro Glu Ile
                485                 490                 495

Ser Asn Asp Thr Tyr Lys Glu Leu Ala Ile Leu Asp Phe Asn Arg Cys
                500                 505                 510

Gln Thr Gln His Gln Leu Glu Trp Ile His Met Gln Glu Trp Tyr Asp
                515                 520                 525

Arg Cys Ser Leu Ser Glu Phe Gly Ile Ser Lys Arg Glu Leu Leu Arg
                530                 535                 540

Ser Tyr Phe Leu Ala Ala Ala Thr Ile Phe Glu Pro Glu Arg Thr Gln
545                 550                 555                 560

Glu Arg Leu Leu Trp Ala Lys Thr Arg Ile Leu Ser Lys Met Ile Thr
                565                 570                 575

Ser Phe Val Asn Ile Ser Gly Thr Thr Leu Ser Leu Asp Tyr Asn Phe
                580                 585                 590

Asn Gly Leu Asp Glu Ile Ile Ser Ser Ala Asn Glu Asp Gln Gly Leu
                595                 600                 605

Ala Gly Thr Leu Leu Ala Thr Phe His Gln Leu Leu Asp Gly Phe Asp
610                 615                 620

Ile Tyr Thr Leu His Gln Leu Lys His Val Trp Ser Gln Trp Phe Met
625                 630                 635                 640

Lys Val Gln Gln Gly Glu Gly Ser Gly Gly Asp Ala Val Leu Leu
                645                 650                 655

Ala Asn Thr Leu Asn Ile Cys Ala Gly Leu Asn Glu Asp Val Leu Ser
                660                 665                 670

Asn Asn Glu Tyr Thr Ala Leu Ser Thr Leu Thr Asn Lys Ile Cys Asn
                675                 680                 685

Arg Leu Ala Gln Ile Gln Asp Asn Lys Ile Leu Gln Val Val Asp Gly
                690                 695                 700

Ser Ile Lys Asp Lys Glu Leu Glu Gln Asp Met Gln Ala Leu Val Lys
705                 710                 715                 720
```

```
Leu Val Leu Gln Glu Asn Gly Gly Ala Val Asp Arg Asn Ile Arg His
            725                 730                 735

Thr Phe Leu Ser Val Ser Lys Thr Phe Tyr Tyr Asp Ala Tyr His Asp
            740                 745                 750

Asp Glu Thr Thr Asp Leu His Ile Phe Lys Val Leu Phe Arg Pro Val
            755                 760                 765

Val

<210> SEQ ID NO 37
<211> LENGTH: 750
<212> TYPE: PRT
<213> ORGANISM: Salvia sclarea

<400> SEQUENCE: 37

Met His Ala Pro Leu Thr Leu Ser Cys Gln Ile Arg Pro Lys Gln Leu
1               5                   10                  15

Ser Gln Ile Ala Glu Leu Arg Val Thr Ser Leu Asp Ala Ser Gln Ala
            20                  25                  30

Ser Glu Lys Asp Ile Ser Leu Val Gln Thr Pro His Lys Val Glu Val
            35                  40                  45

Asn Glu Lys Ile Glu Glu Ser Ile Glu Tyr Val Gln Asn Leu Leu Met
50              55                  60

Thr Ser Gly Asp Gly Arg Ile Ser Val Ser Pro Tyr Asp Thr Ala Val
65              70                  75                  80

Ile Ala Leu Ile Lys Asp Leu Lys Gly Arg Asp Ala Pro Gln Phe Pro
            85                  90                  95

Ser Cys Leu Glu Trp Ile Ala His Gln Leu Ala Asp Gly Ser Trp
            100                 105                 110

Gly Asp Glu Phe Phe Cys Ile Tyr Asp Arg Ile Leu Asn Thr Leu Ala
            115                 120                 125

Cys Val Val Ala Leu Lys Ser Trp Asn Leu His Ser Asp Ile Ile Glu
130             135                 140

Lys Gly Val Thr Tyr Ile Lys Glu Asn Val His Lys Leu Lys Gly Ala
145             150                 155                 160

Asn Val Glu His Arg Thr Ala Gly Phe Glu Leu Val Val Pro Thr Phe
            165                 170                 175

Met Gln Met Ala Thr Asp Leu Gly Ile Gln Asp Leu Pro Tyr Asp His
            180                 185                 190

Pro Leu Ile Lys Glu Ile Ala Asp Thr Lys Gln Gln Arg Leu Lys Glu
            195                 200                 205

Ile Pro Lys Asp Leu Val Tyr Gln Met Pro Thr Asn Leu Leu Tyr Ser
            210                 215                 220

Leu Glu Gly Leu Gly Asp Leu Glu Trp Glu Arg Leu Leu Lys Leu Gln
225             230                 235                 240

Ser Gly Asn Gly Ser Phe Leu Thr Ser Pro Ser Ser Thr Ala Ala Val
            245                 250                 255

Leu Met His Thr Lys Asp Glu Lys Cys Leu Lys Tyr Ile Glu Asn Ala
            260                 265                 270

Leu Lys Asn Cys Asp Gly Gly Ala Pro His Thr Tyr Pro Val Asp Ile
            275                 280                 285

Phe Ser Arg Leu Trp Ala Ile Asp Arg Leu Gln Arg Leu Gly Ile Ser
            290                 295                 300

Arg Phe Phe Gln His Glu Ile Lys Tyr Phe Leu Asp His Ile Glu Ser
305             310                 315                 320

Val Trp Glu Glu Thr Gly Val Phe Ser Gly Arg Tyr Thr Lys Phe Ser
```

-continued

```
            325                 330                 335
Asp Ile Asp Asp Thr Ser Met Gly Val Arg Leu Leu Lys Met His Gly
            340                 345                 350

Tyr Asp Val Asp Pro Asn Val Leu Lys His Phe Lys Gln Gln Asp Gly
            355                 360                 365

Lys Phe Ser Cys Tyr Ile Gly Gln Ser Val Glu Ser Ala Ser Pro Met
            370                 375                 380

Tyr Asn Leu Tyr Arg Ala Ala Gln Leu Arg Phe Pro Gly Glu Glu Val
385                 390                 395                 400

Leu Glu Glu Ala Thr Lys Phe Ala Phe Asn Phe Leu Gln Glu Met Leu
                405                 410                 415

Val Lys Asp Arg Leu Gln Glu Arg Trp Val Ile Ser Asp His Leu Phe
            420                 425                 430

Asp Glu Ile Lys Leu Gly Leu Lys Met Pro Trp Tyr Ala Thr Leu Pro
                435                 440                 445

Arg Val Glu Ala Ala Tyr Tyr Leu Asp His Tyr Ala Gly Ser Gly Asp
            450                 455                 460

Val Trp Ile Gly Lys Ser Phe Tyr Arg Met Pro Glu Ile Ser Asn Asp
465                 470                 475                 480

Thr Tyr Lys Glu Leu Ala Ile Leu Asp Phe Asn Arg Cys Gln Thr Gln
                485                 490                 495

His Gln Leu Glu Trp Ile His Met Gln Glu Trp Tyr Asp Arg Cys Ser
                500                 505                 510

Leu Ser Glu Phe Gly Ile Ser Lys Arg Glu Leu Leu Arg Ser Tyr Phe
            515                 520                 525

Leu Ala Ala Ala Thr Ile Phe Glu Pro Glu Arg Thr Gln Glu Arg Leu
            530                 535                 540

Leu Trp Ala Lys Thr Arg Ile Leu Ser Lys Met Ile Thr Ser Phe Val
545                 550                 555                 560

Asn Ile Ser Gly Thr Thr Leu Ser Leu Asp Tyr Asn Phe Asn Gly Leu
                565                 570                 575

Asp Glu Ile Ile Ser Ser Ala Asn Glu Asp Gln Gly Leu Ala Gly Thr
            580                 585                 590

Leu Leu Ala Thr Phe His Gln Leu Leu Asp Gly Phe Asp Ile Tyr Thr
            595                 600                 605

Leu His Gln Leu Lys His Val Trp Ser Gln Trp Phe Met Lys Val Gln
            610                 615                 620

Gln Gly Glu Gly Ser Gly Gly Glu Asp Ala Val Leu Leu Ala Asn Thr
625                 630                 635                 640

Leu Asn Ile Cys Ala Gly Leu Asn Glu Asp Val Leu Ser Asn Asn Glu
                645                 650                 655

Tyr Thr Ala Leu Ser Thr Leu Thr Asn Lys Ile Cys Asn Arg Leu Ala
                660                 665                 670

Gln Ile Gln Asp Asn Lys Ile Leu Gln Val Val Asp Gly Ser Ile Lys
            675                 680                 685

Asp Lys Glu Leu Glu Gln Asp Met Gln Ala Leu Val Lys Leu Val Leu
            690                 695                 700

Gln Glu Asn Gly Gly Ala Val Asp Arg Asn Ile Arg His Thr Phe Leu
705                 710                 715                 720

Ser Val Ser Lys Thr Phe Tyr Tyr Asp Ala Tyr His Asp Glu Thr
                725                 730                 735

Thr Asp Leu His Ile Phe Lys Val Leu Phe Arg Pro Val Val
            740                 745                 750
```

<210> SEQ ID NO 38
<211> LENGTH: 733
<212> TYPE: PRT
<213> ORGANISM: Salvia sclarea

<400> SEQUENCE: 38

```
Met Ile Ala Glu Leu Arg Val Thr Ser Leu Asp Ala Ser Gln Ala Ser
1               5                   10                  15

Glu Lys Asp Ile Ser Leu Val Gln Thr Pro His Lys Val Glu Val Asn
            20                  25                  30

Glu Lys Ile Glu Glu Ser Ile Glu Tyr Val Gln Asn Leu Leu Met Thr
        35                  40                  45

Ser Gly Asp Gly Arg Ile Ser Val Ser Pro Tyr Asp Thr Ala Val Ile
50                  55                  60

Ala Leu Ile Lys Asp Leu Lys Gly Arg Asp Ala Pro Gln Phe Pro Ser
65                  70                  75                  80

Cys Leu Glu Trp Ile Ala His His Gln Leu Ala Asp Gly Ser Trp Gly
                85                  90                  95

Asp Glu Phe Phe Cys Ile Tyr Asp Arg Ile Leu Asn Thr Leu Ala Cys
            100                 105                 110

Val Val Ala Leu Lys Ser Trp Asn Leu His Ser Asp Ile Ile Glu Lys
        115                 120                 125

Gly Val Thr Tyr Ile Lys Glu Asn Val His Lys Leu Lys Gly Ala Asn
130                 135                 140

Val Glu His Arg Thr Ala Gly Phe Glu Leu Val Val Pro Thr Phe Met
145                 150                 155                 160

Gln Met Ala Thr Asp Leu Gly Ile Gln Asp Leu Pro Tyr Asp His Pro
                165                 170                 175

Leu Ile Lys Glu Ile Ala Asp Thr Lys Gln Gln Arg Leu Lys Glu Ile
            180                 185                 190

Pro Lys Asp Leu Val Tyr Gln Met Pro Thr Asn Leu Leu Tyr Ser Leu
        195                 200                 205

Glu Gly Leu Gly Asp Leu Glu Trp Glu Arg Leu Leu Lys Leu Gln Ser
210                 215                 220

Gly Asn Gly Ser Phe Leu Thr Ser Pro Ser Ser Thr Ala Ala Val Leu
225                 230                 235                 240

Met His Thr Lys Asp Glu Lys Cys Leu Lys Tyr Ile Glu Asn Ala Leu
                245                 250                 255

Lys Asn Cys Asp Gly Gly Ala Pro His Thr Tyr Pro Val Asp Ile Phe
            260                 265                 270

Ser Arg Leu Trp Ala Ile Asp Arg Leu Gln Arg Leu Gly Ile Ser Arg
        275                 280                 285

Phe Phe Gln His Glu Ile Lys Tyr Phe Leu Asp His Ile Glu Ser Val
290                 295                 300

Trp Glu Glu Thr Gly Val Phe Ser Gly Arg Tyr Thr Lys Phe Ser Asp
305                 310                 315                 320

Ile Asp Asp Thr Ser Met Gly Val Arg Leu Leu Lys Met His Gly Tyr
                325                 330                 335

Asp Val Asp Pro Asn Val Leu Lys His Phe Lys Gln Gln Asp Gly Lys
            340                 345                 350

Phe Ser Cys Tyr Ile Gly Gln Ser Val Glu Ser Ala Ser Pro Met Tyr
        355                 360                 365

Asn Leu Tyr Arg Ala Ala Gln Leu Arg Phe Pro Gly Glu Glu Val Leu
370                 375                 380
```

```
Glu Ala Thr Lys Phe Ala Phe Asn Phe Leu Gln Glu Met Leu Val
385                 390                 395                 400

Lys Asp Arg Leu Gln Glu Arg Trp Val Ile Ser Asp His Leu Phe Asp
            405                 410                 415

Glu Ile Lys Leu Gly Leu Lys Met Pro Trp Tyr Ala Thr Leu Pro Arg
            420                 425                 430

Val Glu Ala Ala Tyr Tyr Leu Asp His Tyr Ala Gly Ser Gly Asp Val
            435                 440                 445

Trp Ile Gly Lys Ser Phe Tyr Arg Met Pro Glu Ile Ser Asn Asp Thr
            450                 455                 460

Tyr Lys Glu Leu Ala Ile Leu Asp Phe Asn Arg Cys Gln Thr Gln His
465                 470                 475                 480

Gln Leu Glu Trp Ile His Met Gln Glu Trp Tyr Asp Arg Cys Ser Leu
            485                 490                 495

Ser Glu Phe Gly Ile Ser Lys Arg Glu Leu Leu Arg Ser Tyr Phe Leu
            500                 505                 510

Ala Ala Ala Thr Ile Phe Glu Pro Glu Arg Thr Gln Glu Arg Leu Leu
            515                 520                 525

Trp Ala Lys Thr Arg Ile Leu Ser Lys Met Ile Thr Ser Phe Val Asn
530                 535                 540

Ile Ser Gly Thr Thr Leu Ser Leu Asp Tyr Asn Phe Asn Gly Leu Asp
545                 550                 555                 560

Glu Ile Ile Ser Ser Ala Asn Glu Asp Gln Gly Leu Ala Gly Thr Leu
            565                 570                 575

Leu Ala Thr Phe His Gln Leu Leu Asp Gly Phe Asp Ile Tyr Thr Leu
            580                 585                 590

His Gln Leu Lys His Val Trp Ser Gln Trp Phe Met Lys Val Gln Gln
            595                 600                 605

Gly Glu Gly Ser Gly Gly Glu Asp Ala Val Leu Leu Ala Asn Thr Leu
            610                 615                 620

Asn Ile Cys Ala Gly Leu Asn Glu Asp Val Leu Ser Asn Asn Glu Tyr
625                 630                 635                 640

Thr Ala Leu Ser Thr Leu Thr Asn Lys Ile Cys Asn Arg Leu Ala Gln
            645                 650                 655

Ile Gln Asp Asn Lys Ile Leu Gln Val Val Asp Gly Ser Ile Lys Asp
            660                 665                 670

Lys Glu Leu Glu Gln Asp Met Gln Ala Leu Val Lys Leu Val Leu Gln
            675                 680                 685

Glu Asn Gly Gly Ala Val Asp Arg Asn Ile Arg His Thr Phe Leu Ser
            690                 695                 700

Val Ser Lys Thr Phe Tyr Tyr Asp Ala Tyr His Asp Asp Glu Thr Thr
705                 710                 715                 720

Asp Leu His Ile Phe Lys Val Leu Phe Arg Pro Val Val
            725                 730

<210> SEQ ID NO 39
<211> LENGTH: 723
<212> TYPE: PRT
<213> ORGANISM: Salvia sclarea

<400> SEQUENCE: 39

Met Ala Ser Gln Ala Ser Glu Lys Asp Ile Ser Leu Val Gln Thr Pro
1               5                   10                  15

His Lys Val Glu Val Asn Glu Lys Ile Glu Glu Ser Ile Glu Tyr Val
            20                  25                  30
```

-continued

```
Gln Asn Leu Leu Met Thr Ser Gly Asp Gly Arg Ile Ser Val Ser Pro
             35                  40                  45

Tyr Asp Thr Ala Val Ile Ala Leu Ile Lys Asp Leu Lys Gly Arg Asp
 50                  55                  60

Ala Pro Gln Phe Pro Ser Cys Leu Glu Trp Ile Ala His His Gln Leu
 65                  70                  75                  80

Ala Asp Gly Ser Trp Gly Asp Glu Phe Phe Cys Ile Tyr Asp Arg Ile
                 85                  90                  95

Leu Asn Thr Leu Ala Cys Val Val Ala Leu Lys Ser Trp Asn Leu His
                100                 105                 110

Ser Asp Ile Ile Glu Lys Gly Val Thr Tyr Ile Lys Glu Asn Val His
            115                 120                 125

Lys Leu Lys Gly Ala Asn Val Glu His Arg Thr Ala Gly Phe Glu Leu
130                 135                 140

Val Val Pro Thr Phe Met Gln Met Ala Thr Asp Leu Gly Ile Gln Asp
145                 150                 155                 160

Leu Pro Tyr Asp His Pro Leu Ile Lys Glu Ile Ala Asp Thr Lys Gln
                165                 170                 175

Gln Arg Leu Lys Glu Ile Pro Lys Asp Leu Val Tyr Gln Met Pro Thr
            180                 185                 190

Asn Leu Leu Tyr Ser Leu Glu Gly Leu Gly Asp Leu Glu Trp Glu Arg
            195                 200                 205

Leu Leu Lys Leu Gln Ser Gly Asn Gly Ser Phe Leu Thr Ser Pro Ser
210                 215                 220

Ser Thr Ala Ala Val Leu Met His Thr Lys Asp Glu Lys Cys Leu Lys
225                 230                 235                 240

Tyr Ile Glu Asn Ala Leu Lys Asn Cys Asp Gly Gly Ala Pro His Thr
                245                 250                 255

Tyr Pro Val Asp Ile Phe Ser Arg Leu Trp Ala Ile Asp Arg Leu Gln
            260                 265                 270

Arg Leu Gly Ile Ser Arg Phe Phe Gln His Glu Ile Lys Tyr Phe Leu
            275                 280                 285

Asp His Ile Glu Ser Val Trp Glu Glu Thr Gly Val Phe Ser Gly Arg
290                 295                 300

Tyr Thr Lys Phe Ser Asp Ile Asp Asp Thr Ser Met Gly Val Arg Leu
305                 310                 315                 320

Leu Lys Met His Gly Tyr Asp Val Asp Pro Asn Val Leu Lys His Phe
                325                 330                 335

Lys Gln Gln Asp Gly Lys Phe Ser Cys Tyr Ile Gly Gln Ser Val Glu
            340                 345                 350

Ser Ala Ser Pro Met Tyr Asn Leu Tyr Arg Ala Ala Gln Leu Arg Phe
            355                 360                 365

Pro Gly Glu Glu Val Leu Glu Glu Ala Thr Lys Phe Ala Phe Asn Phe
370                 375                 380

Leu Gln Glu Met Leu Val Lys Asp Arg Leu Gln Glu Arg Trp Val Ile
385                 390                 395                 400

Ser Asp His Leu Phe Asp Glu Ile Lys Leu Gly Leu Lys Met Pro Trp
                405                 410                 415

Tyr Ala Thr Leu Pro Arg Val Glu Ala Ala Tyr Tyr Leu Asp His Tyr
            420                 425                 430

Ala Gly Ser Gly Asp Val Trp Ile Gly Lys Ser Phe Tyr Arg Met Pro
            435                 440                 445

Glu Ile Ser Asn Asp Thr Tyr Lys Glu Leu Ala Ile Leu Asp Phe Asn
450                 455                 460
```

```
Arg Cys Gln Thr Gln His Gln Leu Glu Trp Ile His Met Gln Glu Trp
465                 470                 475                 480

Tyr Asp Arg Cys Ser Leu Ser Glu Phe Gly Ile Ser Lys Arg Glu Leu
                485                 490                 495

Leu Arg Ser Tyr Phe Leu Ala Ala Thr Ile Phe Glu Pro Glu Arg
            500                 505                 510

Thr Gln Glu Arg Leu Leu Trp Ala Lys Thr Arg Ile Leu Ser Lys Met
                515                 520                 525

Ile Thr Ser Phe Val Asn Ile Ser Gly Thr Thr Leu Ser Leu Asp Tyr
            530                 535                 540

Asn Phe Asn Gly Leu Asp Glu Ile Ile Ser Ser Ala Asn Glu Asp Gln
545                 550                 555                 560

Gly Leu Ala Gly Thr Leu Leu Ala Thr Phe His Gln Leu Leu Asp Gly
                565                 570                 575

Phe Asp Ile Tyr Thr Leu His Gln Leu Lys His Val Trp Ser Gln Trp
            580                 585                 590

Phe Met Lys Val Gln Gln Gly Glu Gly Ser Gly Gly Glu Asp Ala Val
            595                 600                 605

Leu Leu Ala Asn Thr Leu Asn Ile Cys Ala Gly Leu Asn Glu Asp Val
610                 615                 620

Leu Ser Asn Asn Glu Tyr Thr Ala Leu Ser Thr Leu Thr Asn Lys Ile
625                 630                 635                 640

Cys Asn Arg Leu Ala Gln Ile Gln Asp Asn Lys Ile Leu Gln Val Val
                645                 650                 655

Asp Gly Ser Ile Lys Asp Lys Glu Leu Glu Gln Asp Met Gln Ala Leu
                660                 665                 670

Val Lys Leu Val Leu Gln Glu Asn Gly Gly Ala Val Asp Arg Asn Ile
            675                 680                 685

Arg His Thr Phe Leu Ser Val Ser Lys Thr Phe Tyr Tyr Asp Ala Tyr
            690                 695                 700

His Asp Asp Glu Thr Thr Asp Leu His Ile Phe Lys Val Leu Phe Arg
705                 710                 715                 720

Pro Val Val

<210> SEQ ID NO 40
<211> LENGTH: 81
<212> TYPE: DNA
<213> ORGANISM: Salvia sclarea

<400> SEQUENCE: 40
ctgatgtttc tgtctacggc gccgccattt tcttgaagca ctaacttcac caacgcctgc     60
atatcctgtt ctagctcctt a                                              81

<210> SEQ ID NO 41
<211> LENGTH: 73
<212> TYPE: DNA
<213> ORGANISM: Salvia sclarea

<400> SEQUENCE: 41
attcctgcat atggatccac tccaactgat gttgtgtttg gcatctgttg aaatccaata     60
tcgcaagctc ctt                                                       73

<210> SEQ ID NO 42
<211> LENGTH: 52
<212> TYPE: DNA
<213> ORGANISM: Salvia sclarea
```

<400> SEQUENCE: 42

```
tattattgaa aaaggagtga cgtacatcaa ggagaatgtg cataaactta aa         52
```

<210> SEQ ID NO 43
<211> LENGTH: 857
<212> TYPE: DNA
<213> ORGANISM: Salvia sclarea

<400> SEQUENCE: 43

```
atgtcaccac aaacagagac taaagcaagt gttggattca agcgggtgt taaagagtac    60
aaattgactt attatactcc tgaatacgaa accaaagata ctgatatctt ggcagcattc   120
cgagtaactc ctcaacccgg agttccgcct gaagaagcag gggccgcggt agctgccgaa   180
tcttctactg gtacatggac aactgtgtgg accgatggac ttaccagcct tgatcgttac   240
aaagggcgat gctaccacat tgagcccgtt cctggagaaa agatcaata tatctgttat   300
gtagcttacc ctttagacct ttttgaagaa ggttctgtta ctaacatgtt tacttccatt   360
gtaggaaatg tatttggatt caaagcccta cgtgctctac gtctggaaga tctgcgaatt   420
cctgttgctt atgttaaaac tttccaaggc ccgcctcatg ggatccaagt tgagagagat   480
aaattgaaca gtacggtcg tcctctgctg ggatgtacta ttaaacctaa attggggtta    540
tctgctaaaa actatggtag agcggtttat gaatgtcttc gcggtggact tgattttacc   600
aaagatgatg agaacgtgaa ctcccagcca tttatgcgtt ggagagaccg cttcttattt   660
tgtgccgaag caatttataa agcacaggct gaaacaggtg aaatcaaagg cattacttg    720
aatgctactg cgggtacatg cgaagagatg atgaaaagag ctatatttgc tagagaattg   780
ggagttccta tcgtaatgca cgactactta acaggaggat tcaccgcaaa taccagtttg   840
gctcattatt gccgaga                                                 857
```

<210> SEQ ID NO 44
<211> LENGTH: 540
<212> TYPE: DNA
<213> ORGANISM: Salvia sclarea

<400> SEQUENCE: 44

```
aaagtatcca ctgctttaaa ttcaaacttg atttctttcc atacctcaca agcggcagct    60
agttcaggac tccatttgca agcttcacgg ataattgcat taccttcagc agcaagatca   120
cgtccttcat tacgagcttt tacacacgct tctacagcta ctcggttagc tacagcacct   180
ggtgcattac cccaagggtg tcctaaagtt cctccaccga actgtagtac ggaatcgtct   240
ccaaagatct cggtcagagc aggcatatgc caaacgtgaa taccccctga agccacagga   300
ataacacccg gcagggagac ccaatcttga gtgaaataaa taccgcgact tcggtctttt   360
tcaataaaat catcacgcag taaatcaaca aaacctaaag taatgtctct ctctccttca   420
agtttaccta ctacggtacc agagtgaata tgatctccac cggacagacg taacgcttta   480
gctagtacac ggaagtgcat accgtgattc ttctgtctat caataactgc atgcattgca   540
```

<210> SEQ ID NO 45
<211> LENGTH: 60
<212> TYPE: DNA
<213> ORGANISM: Salvia sclarea

<400> SEQUENCE: 45

```
atgttcgtct cgcatttgcc aaaacatctg tgcttgtaac aattatggat gattttttcg    60
```

```
<210> SEQ ID NO 46
<211> LENGTH: 35
<212> TYPE: DNA
<213> ORGANISM: Salvia sclarea

<400> SEQUENCE: 46
cttctacctt ggcctgcatt cttgctctta aaaaa                                35

<210> SEQ ID NO 47
<211> LENGTH: 35
<212> TYPE: DNA
<213> ORGANISM: Salvia sclarea

<400> SEQUENCE: 47
aaaaaaaata tgatctaaaa aatggatcag tttaa                                35

<210> SEQ ID NO 48
<211> LENGTH: 72
<212> TYPE: DNA
<213> ORGANISM: Salvia sclarea

<400> SEQUENCE: 48
actactcatg caatggcatt taggcttttg cgagtgaaag gatacgaagt ttcatcagag     60
gagttggcct ca                                                        72

<210> SEQ ID NO 49
<211> LENGTH: 35
<212> TYPE: DNA
<213> ORGANISM: Salvia sclarea

<400> SEQUENCE: 49
gcaactgatg attttgtgga tgttgggggc agctc                                35

<210> SEQ ID NO 50
<211> LENGTH: 35
<212> TYPE: DNA
<213> ORGANISM: Salvia sclarea

<400> SEQUENCE: 50
gccaaaataa ttccttgcat ggctttggaa ggaga                                35

<210> SEQ ID NO 51
<211> LENGTH: 11
<212> TYPE: PRT
<213> ORGANISM: Salvia sclarea

<400> SEQUENCE: 51

Ser Thr Leu Ala Cys Ile Leu Ala Leu Lys Lys
1               5                   10

<210> SEQ ID NO 52
<211> LENGTH: 10
<212> TYPE: PRT
<213> ORGANISM: Salvia sclarea

<400> SEQUENCE: 52

Lys Lys Tyr Asp Leu Lys Asn Gly Ser Val
1               5                   10

<210> SEQ ID NO 53
<211> LENGTH: 24
<212> TYPE: PRT
<213> ORGANISM: Salvia sclarea

<400> SEQUENCE: 53
```

```
Thr Thr His Ala Met Ala Phe Arg Leu Leu Arg Val Lys Gly Tyr Glu
1               5                   10                  15

Val Ser Ser Glu Glu Leu Ala Ser
            20

<210> SEQ ID NO 54
<211> LENGTH: 11
<212> TYPE: PRT
<213> ORGANISM: Salvia sclarea

<400> SEQUENCE: 54

Ala Thr Asp Asp Phe Val Asp Val Gly Gly Ser
1               5                   10

<210> SEQ ID NO 55
<211> LENGTH: 11
<212> TYPE: PRT
<213> ORGANISM: Salvia sclarea

<400> SEQUENCE: 55

Leu Leu Pro Lys Pro Cys Lys Glu Leu Phe Trp
1               5                   10

<210> SEQ ID NO 56
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 56
cttctacctt ggcctgcatt cttgctc                                    27

<210> SEQ ID NO 57
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 57
ctactcatgc aatggcattt aggcttttgc g                               31

<210> SEQ ID NO 58
<211> LENGTH: 33
<212> TYPE: DNA
<213> ORGANISM: Salvia sclarea

<400> SEQUENCE: 58
gtgaaaggat acgaagtttc atcagaggag ttg                             33

<210> SEQ ID NO 59
<211> LENGTH: 32
<212> TYPE: DNA
<213> ORGANISM: Artificial sequence
<220> FEATURE:
<223> OTHER INFORMATION: Oligonucleotide primer

<400> SEQUENCE: 59
gaggccaact cctctgatga aacttcgtat cc                              32

<210> SEQ ID NO 60
<211> LENGTH: 30
<212> TYPE: DNA
<213> ORGANISM: Artificial sequence
```

```
<220> FEATURE:
<223> OTHER INFORMATION: Oligonucleotide primer

<400> SEQUENCE: 60
cactcgcaaa agcctaaatg ccattgcatg                                       30

<210> SEQ ID NO 61
<211> LENGTH: 36
<212> TYPE: DNA
<213> ORGANISM: Artificial sequence
<220> FEATURE:
<223> OTHER INFORMATION: Synthetic oligonucleotide primer

<400> SEQUENCE: 61
cctatagtgt caaaagacaa aggatttcat atcttc                                36

<210> SEQ ID NO 62
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 62
gcttattgag aaagatggta gtccaagcaa g                                     31

<210> SEQ ID NO 63
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 63
gctctataaa gctcaataat catcggcagg tc                                    32

<210> SEQ ID NO 64
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 64
caccatgtcg ctcgccttca acg                                              23

<210> SEQ ID NO 65
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 65
caccatggcg aaaatgaaag agaatttcaa gag                                   33

<210> SEQ ID NO 66
<211> LENGTH: 547
<212> TYPE: DNA
<213> ORGANISM: Salvia sclarea

<400> SEQUENCE: 66
agcggccgct gaattctaga atttggatgt ggaatagaat tgacgaatgg cgtgcaagcg      60
cgcctctctc ctctctcctc tctctagaaa atatgattgt gcagttgagt tggcaaaagc     120
gtatctgatt cctgcccttt gctaactttc ccaaattttg tcccgtttaa ttccataggg     180
```

```
gatttcttca aggccgccat gtcgcttcct ctctccactt gcaatggatc acattttcgg    240
agataccgct tgtctcctgc ttcagcagct tctatggaaa ctgggcttca aactgctact    300
tcagcaaaaa tcgcctctat gccagcgtgc tttgaggaga cgagagggag gatagcaaag    360
ttgtttcata aggatgaact ttctgtgtcg acatatgata cagcatgggt tgccatggtc    420
ccttctccaa cttcgttaga ggaaccttgc ttccccgatt gtctaaactg gttgctcgag    480
aaccagtgcc atgatggttc gtgggcccgt ccccaccatc actctttgct aatgaaagat    540
gtcctttt                                                             547
```

<210> SEQ ID NO 67
<211> LENGTH: 1473
<212> TYPE: DNA
<213> ORGANISM: Salvia sclarea

<400> SEQUENCE: 67

```
ctccatatgg taaccaagag gctgttagcc agcaaacaaa tgacctgccg atgattattg     60
agctttatag agcagcaaat gagagaatat atgaagaaga gaggagtctt gaaaaaattc    120
ttgcttggac taccatcttt ctcaataagc aagtgcaaga taactcaatt cccgacaaaa    180
aactgcacaa actggtggaa ttctacttga ggaattacaa aggcataacc ataagattgg    240
gagctagacg aaacctcgag ctatatgaca tgacctacta tcaagctctg aaatctacaa    300
acaggttctc taatttatgc aacgaagatt ttctagtttt cgcaaagcaa gatttcgata    360
tacatgaagc ccagaaccag aaaggacttc aacaactgca aagtggtat gcagattgta    420 ggttggacac cttaaacttt ggaagagatg tagttattat tgctaattat ttggcttcat    480
taattattgg tgatcatgcg tttgactatg ttcgtctcgc atttgccaaa acatctgtgc    540
ttgtaacaat tatggatgat ttttcgact gtcatggctc tagtcaagag tgtgacaaga    600
tcattgaatt agtaaaagaa tggaaggaga tccggatgc agagtacgga tctgaggagc    660
ttgagatcct ttttatggcg ttgtacaata cagtaaatga gttggcggag agggctcgtg    720
ttgaacaggg gcgtagtgtc aaagagtttc tagtcaaact gtgggttgaa atactctcag    780 cttttcaagat agaattagat acatggagca atggcacgca gcaaagcttc gatgaataca    840
tttcttcgtc gtggttgtcg aacggttccc ggctgacagg tctcctgacg atgcaattcg    900
tcggagtaaa attgtccgat gaaatgctta tgagtgaaga gtgcactgat ttggctaggc    960
atgtctgtat ggtcggccgg ctgctcaacg acgtgtgcag ttctgagagg gagcgcgagg   1020
aaaatattgc aggaaaaagt tatagcattc tactagcaac tgagaaagat ggaagaaaag   1080
ttagtgaaga tgaagccatt gcagagatca atgaaatggt tgaatatcac tggagaaaag   1140
tgttgcagat tgtgtataaa aagaaagca ttttgccaag aagatgcaaa gatgtatttt   1200
tggagatggc taagggtacg ttttatgctt atgggatcaa cgatgaattg acttctcctc   1260
agcaatccaa ggaagatatg aaatcctttg tcttttgaca ctataggctc gtttggtacg   1320
ggtgatatta gggtgtgtaa tacaattatg acactgtaat attttatttt gtacaaaaca   1380
cgtggttctt tgcatatcaa aaatttgaaa atgttataag gattgtatc cactataaga   1440 aattgttgga taaaaaaaaa aaaaaaaaaa aaa                                 1473
```

<210> SEQ ID NO 68
<211> LENGTH: 464
<212> TYPE: DNA
<213> ORGANISM: Salvia sclarea

<400> SEQUENCE: 68

```
aaattaatta ggaataaaaa aaattggact ttatatttat tagaaacggc cgccgccgca    60
aaaaaatgtc gctcgccttc aacgtcggag ttacgccttt ctccggccaa agagttggga   120
gcaggaaaga aaatttcca gtccaaggat ttcctgtgac cacccccaat aggtcacgtc   180
tcatcgttaa ctgcagcctt actacaatag atttcatggc gaaaatgaaa gagaatttca   240
agagggaaga cgataaattt ccaacgacaa cgactcttcg atccgaagat atacccteta   300 atttgtgtat aatcgacacc cttcaaaggt tgggggtcga tcaattcttc caatatgaaa   360
tcaacactat tctagataac acattcaggt tgtggcaaga aaaacacaaa gttatatatg   420
gcaatgttac tactcatgca atggcattta ggcttttgcg agtg                   464

<210> SEQ ID NO 69
<211> LENGTH: 536
<212> TYPE: DNA
<213> ORGANISM: Salvia sclarea

<400> SEQUENCE: 69
aaattaatta ggaataaaaa aaattggact ttatatttat tagaaacggc cgccgccgca    60
aaaaaatgtc gctcgccttc aacgtcggag ttacgccttt ctccggccaa agagttggga   120
gcaggaaaga aaatttcca gtccaaggat ttcctgtgac cacccccaat aggtcacgtc   180
tcatcgttaa ctgcagcctt actacaatag atttcatggc gaaaatgaaa gagaatttca   240
agagggaaga cgataaattt ccaacgacaa cgactcttcg atccgaagat atacccteta   300 atttgtgtat aatcgacacc cttcaaaggt tgggggtcga tcaattcttc caatatgaaa   360
tcaacactat tctagataac acattcaggt tgtggcaaga aaaacacaaa gttatatatg   420
gcaatgttac tactcatgca atggcattta ggcttttgcg agtgaaagga tacgaagttt   480
catcagagga gttggctcca tatggtaacc aagaggctgt tagccagcaa acaaat      536

<210> SEQ ID NO 70
<211> LENGTH: 95
<212> TYPE: DNA
<213> ORGANISM: Salvia sclarea

<400> SEQUENCE: 70
ttgcatcttc ttggcaaaat gctttctttt ttatacacaa tctgcaacac ttttctccag    60
tgatattcaa ccatttcatt gatctctgca atggc                              95

<210> SEQ ID NO 71
<211> LENGTH: 55
<212> TYPE: DNA
<213> ORGANISM: Salvia sclarea

<400> SEQUENCE: 71
tgaagcccag aaccagaaag gacttcaaca actgcaaagg tggtatgcag attgt         55

<210> SEQ ID NO 72
<211> LENGTH: 53
<212> TYPE: DNA
<213> ORGANISM: Salvia sclarea

<400> SEQUENCE: 72
tactctgcat ccggattctc cttccattct tttactaatt caatgatctt gtc            53

<210> SEQ ID NO 73
<211> LENGTH: 1578
<212> TYPE: DNA
<213> ORGANISM: Salvia sclarea
```

<400> SEQUENCE: 73

```
atggcgaaaa tgaaagagaa tttcaagagg gaagacgata aatttccaac gacaacgact      60
cttcgatccg aagatatacc ctctaatttg tgtataatcg acacccttca aaggttgggg     120
gtcgatcaat tcttccaata tgaaatcaac actattctag ataacacatt caggttgtgg     180
caagaaaaac acaaagttat atatggcaat gttactactc atgcaatggc atttaggctt     240
tgcgagtga aaggatacga agtttcatca gaggagttgg ctccatatgg taaccaagag      300
gctgttagcc agcaaacaaa tgacctgccg atgattattg agctttatag cagcaaat      360
gagagaatat atgaagaaga gaggagtctt gaaaaaattc ttgcttggac taccatcttt     420
ctcaataagc aagtgcaaga taactcaatt cccgacaaaa aactgcacaa actggtggaa     480
ttctacttga ggaattacaa aggcataacc ataagattgg gagctagacg aaacctcgag     540
ctatatgaca tgacctacta tcaagctctg aaatctacaa acaggttctc taatttatgc     600
aacgaagatt ttctagtttt cgcaaagcaa gatttcgata catgaagc ccagaaccag       660
aaaggacttc aacaactgca aaggtggtat gcagattgta ggttggacac cttaaacttt     720
ggaagagatg tagttattat tgctaattat ttggcttcat taattattgg tgatcatgcg     780
tttgactatg ttcgtctcgc atttgccaaa acatctgtgc ttgtaacaat tatggatgat     840
tttttcgact gtcatggctc tagtcaagag tgtgacaaga tcattgaatt agtaaaagaa     900
tggaaggaga atccggatgc agagtacgga tctgaggagc ttgagatcct ttttatggcg     960
ttgtacaata cagtaaatga gttggcgag agggctcgtg ttgaacaggg gcgtagtgtc     1020
aaagagtttc tagtcaaact gtgggttgaa atactctcag ctttcaagat agaattagat    1080
acatggagca atggcacgca gcaaagcttc gatgaataca tttcttcgtc gtggttgtcg    1140
aacggttccc ggctgacagg tctcctgacg atgcaattcg tcggagtaaa attgtccgat    1200
gaaatgctta tgagtgaaga gtgcactgat ttggctaggc atgtctgtat ggtcggccgg    1260
ctgctcaacg acgtgtgcag ttctgagagg gagcgcgagg aaaatattgc aggaaaaagt    1320
tatagcattc tactagcaac tgagaaagat ggaagaaaag ttagtgaaga tgaagccatt    1380
gcagagatca atgaaatggt tgaatatcac tggagaaaag tgttgcagat tgtgtataaa    1440
aaagaaagca ttttgccaag aagatgcaaa gatgtatttt tggagatggc taagggtacg    1500
ttttatgctt atgggatcaa cgatgaattg acttctcctc agcaatccaa ggaagatatg    1560
aaatcctttg tcttttga                                                   1578
```

<210> SEQ ID NO 74
<211> LENGTH: 525
<212> TYPE: PRT
<213> ORGANISM: Salvia sclarea

<400> SEQUENCE: 74

```
Met Ala Lys Met Lys Glu Asn Phe Lys Arg Glu Asp Asp Lys Phe Pro
1               5                   10                  15

Thr Thr Thr Thr Leu Arg Ser Glu Asp Ile Pro Ser Asn Leu Cys Ile
            20                  25                  30

Ile Asp Thr Leu Gln Arg Leu Gly Val Asp Gln Phe Phe Gln Tyr Glu
        35                  40                  45

Ile Asn Thr Ile Leu Asp Asn Thr Phe Arg Leu Trp Gln Glu Lys His
    50                  55                  60

Lys Val Ile Tyr Gly Asn Val Thr Thr His Ala Met Ala Phe Arg Leu
65                  70                  75                  80
```

```
Leu Arg Val Lys Gly Tyr Glu Val Ser Ser Glu Leu Ala Pro Tyr
            85                  90                  95

Gly Asn Gln Glu Ala Val Ser Gln Gln Thr Asn Asp Leu Pro Met Ile
            100                 105                 110

Ile Glu Leu Tyr Arg Ala Ala Asn Glu Arg Ile Tyr Glu Glu Arg
            115                 120                 125

Ser Leu Glu Lys Ile Leu Ala Trp Thr Thr Ile Phe Leu Asn Lys Gln
            130                 135                 140

Val Gln Asp Asn Ser Ile Pro Asp Lys Lys Leu His Lys Leu Val Glu
145                 150                 155                 160

Phe Tyr Leu Arg Asn Tyr Lys Gly Ile Thr Ile Arg Leu Gly Ala Arg
            165                 170                 175

Arg Asn Leu Glu Leu Tyr Asp Met Thr Tyr Tyr Gln Ala Leu Lys Ser
            180                 185                 190

Thr Asn Arg Phe Ser Asn Leu Cys Asn Glu Asp Phe Leu Val Phe Ala
            195                 200                 205

Lys Gln Asp Phe Asp Ile His Glu Ala Gln Asn Gln Lys Gly Leu Gln
            210                 215                 220

Gln Leu Gln Arg Trp Tyr Ala Asp Cys Arg Leu Asp Thr Leu Asn Phe
225                 230                 235                 240

Gly Arg Asp Val Val Ile Ala Asn Tyr Leu Ala Ser Leu Ile Ile
            245                 250                 255

Gly Asp His Ala Phe Asp Tyr Val Arg Leu Ala Phe Ala Lys Thr Ser
            260                 265                 270

Val Leu Val Thr Ile Met Asp Asp Phe Phe Asp Cys His Gly Ser Ser
            275                 280                 285

Gln Glu Cys Asp Lys Ile Ile Glu Leu Val Lys Glu Trp Lys Glu Asn
290                 295                 300

Pro Asp Ala Glu Tyr Gly Ser Glu Glu Leu Glu Ile Leu Phe Met Ala
305                 310                 315                 320

Leu Tyr Asn Thr Val Asn Glu Leu Ala Glu Arg Ala Arg Val Glu Gln
            325                 330                 335

Gly Arg Ser Val Lys Glu Phe Leu Val Lys Leu Trp Val Glu Ile Leu
            340                 345                 350

Ser Ala Phe Lys Ile Glu Leu Asp Thr Trp Ser Asn Gly Thr Gln Gln
            355                 360                 365

Ser Phe Asp Glu Tyr Ile Ser Ser Ser Trp Leu Ser Asn Gly Ser Arg
            370                 375                 380

Leu Thr Gly Leu Leu Thr Met Gln Phe Val Gly Val Lys Leu Ser Asp
385                 390                 395                 400

Glu Met Leu Met Ser Glu Glu Cys Thr Asp Leu Ala Arg His Val Cys
            405                 410                 415

Met Val Gly Arg Leu Leu Asn Asp Val Cys Ser Ser Glu Arg Glu Arg
            420                 425                 430

Glu Glu Asn Ile Ala Gly Lys Ser Tyr Ser Ile Leu Leu Ala Thr Glu
            435                 440                 445

Lys Asp Gly Arg Lys Val Ser Glu Asp Glu Ala Ile Ala Glu Ile Asn
450                 455                 460

Glu Met Val Glu Tyr His Trp Arg Lys Val Leu Gln Ile Val Tyr Lys
465                 470                 475                 480

Lys Glu Ser Ile Leu Pro Arg Arg Cys Lys Asp Val Phe Leu Glu Met
            485                 490                 495

Ala Lys Gly Thr Phe Tyr Ala Tyr Gly Ile Asn Asp Glu Leu Thr Ser
            500                 505                 510
```

-continued

```
Pro Gln Gln Ser Lys Glu Asp Met Lys Ser Phe Val Phe
        515                 520                 525

<210> SEQ ID NO 75
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 75
ctagccatgg cttcagaaaa agaaattagg                                    30

<210> SEQ ID NO 76
<211> LENGTH: 40
<212> TYPE: DNA
<213> ORGANISM: Artificial sequence
<220> FEATURE:
<223> OTHER INFORMATION: Synthetic oligonucleotide primer

<400> SEQUENCE: 76
ccggaattcc tatttgcttc tcttgtaaac tttgttcaag                         40

<210> SEQ ID NO 77
<211> LENGTH: 42
<212> TYPE: DNA
<213> ORGANISM: Artificial sequence
<220> FEATURE:
<223> OTHER INFORMATION: Synthetic oligonucleotide primer

<400> SEQUENCE: 77
aaggagatat acatatgaca aaaaagttg gtgtcggtca gg                       42

<210> SEQ ID NO 78
<211> LENGTH: 43
<212> TYPE: DNA
<213> ORGANISM: Artificial sequence
<220> FEATURE:
<223> OTHER INFORMATION: Synthetic oligonucleotide primer

<400> SEQUENCE: 78
ctttaccaga ctcgagttac gccttttttca tctgatcctt tgc                    43

<210> SEQ ID NO 79
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 79
attaccatgg tttctggttc gaaagcagga g                                  31

<210> SEQ ID NO 80
<211> LENGTH: 36
<212> TYPE: DNA
<213> ORGANISM: Artificial sequence
<220> FEATURE:
<223> OTHER INFORMATION: Synthetic oligonucleotide primer

<400> SEQUENCE: 80
ttaaggatcc ttaggcgatc ttcatcactg gagacc                             36

<210> SEQ ID NO 81
<211> LENGTH: 15
<212> TYPE: DNA
```

-continued

```
<213> ORGANISM: Artificial sequence
<220> FEATURE:
<223> OTHER INFORMATION: Link between the LPP synthase and the sclareol
      synthase in the nucleic acid encoding the fusion polypeptide.

<400> SEQUENCE: 81
ggtggttctg gtggt                                                          15

<210> SEQ ID NO 82
<211> LENGTH: 5
<212> TYPE: PRT
<213> ORGANISM: Artificial sequence
<220> FEATURE:
<223> OTHER INFORMATION: Link between the LPP synthase and the sclareol
      synthase in the fusion polypeptide.

<400> SEQUENCE: 82

Gly Gly Ser Gly Gly
1               5

<210> SEQ ID NO 83
<211> LENGTH: 39
<212> TYPE: DNA
<213> ORGANISM: Artificial sequence
<220> FEATURE:
<223> OTHER INFORMATION: Synthetic oligonucleotide primer

<400> SEQUENCE: 83
aaggagatat acatatggcg tcgcaagcga gtgaaaaag                                 39

<210> SEQ ID NO 84
<211> LENGTH: 40
<212> TYPE: DNA
<213> ORGANISM: Artificial sequence
<220> FEATURE:
<223> OTHER INFORMATION: Synthetic oligonucleotide primer

<400> SEQUENCE: 84
accaccagaa ccacctacaa ccggtcgaaa gagtactttg                                40

<210> SEQ ID NO 85
<211> LENGTH: 41
<212> TYPE: DNA
<213> ORGANISM: Artificial sequence
<220> FEATURE:
<223> OTHER INFORMATION: Synthetic oligonucleotide primer

<400> SEQUENCE: 85
ggtggttctg gtggtgcgaa aatgaaagag aatttcaaga g                              41

<210> SEQ ID NO 86
<211> LENGTH: 51
<212> TYPE: DNA
<213> ORGANISM: Artificial sequence
<220> FEATURE:
<223> OTHER INFORMATION: Synthetic oligonucleotide primer

<400> SEQUENCE: 86
ttaccagact cgagggtacc ttatcaaaag acaaggatt tcatatcttc c                    51

<210> SEQ ID NO 87
<211> LENGTH: 3759
<212> TYPE: DNA
<213> ORGANISM: Artificial sequence
<220> FEATURE:
<223> OTHER INFORMATION: Fusion protein containing a LPP synthase and a
      sclareol synthase from Salvia sclarea
```

<400> SEQUENCE: 87

```
atggcgtcgc aagcgagtga aaaagacatt tcccttgttc aaactccgca taaggttgag      60
gttaatgaaa agatcgagga gtcaatcgag tacgtccaaa atctgttgat gacgtcgggc     120
gacgggcgaa taagcgtgtc accctatgac acggcagtga tcgccctgat caaggacttg     180
aaagggcgcg acgccccgca gtttccgtca tgtctcgagt ggatcgcgca ccaccaactg     240
gctgatggct catggggcga cgaattcttc tgtatttatg atcggattct aaatacattg     300
gcatgtgtcg tagccttgaa atcatggaac cttcactctg atattattga aaaggagtg      360
acgtacatca aggagaatgt gcataaactt aaaggtgcaa atgttgagca caggacagcg     420
gggttcgaac ttgtggttcc tacttttatg caaatggcca cagatttggg catccaagat     480
ctgccctatg atcatcccct catcaaggag attgctgaca caaaacaaca aagattgaaa     540
gagatacccc aggatttggt ttaccaaatg ccaacgaatt tactgtacag tttagaaggg     600
ttaggagatt tggagtggga aaggctactg aaactgcagt cgggcaatgg ctccttcctc     660
acttcgccgt cgtccaccgc cgccgtcttg atgcatacca aagatgaaaa atgtttgaaa     720
tacatcgaaa acgccctcaa gaattgcgac ggaggagcac cacatactta tccagtcgat     780
atcttctcaa gactttgggc aatcgatagg ctacaacgcc taggaatttc tcgtttcttc     840
cagcacgaga tcaagtattt cttagatcac atcgaaagcg tttgggagga gaccggagtt     900
ttcagtggaa gatatacgaa atttagcgat attgatgaca cgtccatggg cgttaggctt     960
ctcaaaatgc acggatacga cgtcgatcca aatgtactaa acatttcaa gcaacaagat     1020
ggtaaatttt cctgctacat tggtcaatcg gtcgagtctg catctccaat gtacaatctt    1080
tatagggctg ctcaactaag atttccagga gaagaagttc ttgaagaagc cactaaattt    1140
gccttaact tcttgcaaga aatgctagtc aaagatcgac ttcaagaaag atgggtgata    1200
tccgaccact tatttgatga gataaagctg gggttgaaga tgccatggta cgccactcta    1260
ccccgagtcg aggctgcata ttatctagac cattatgctg gttctggtga tgtatggatt    1320
ggcaagagtt tctacaggat gccagaaatc agcaatgata catacaagga gcttgcgata    1380
ttggatttca acagatgcca aacacaacat cagttggagt ggatccacat gcaggaatgg    1440
tacgacagat gcagccttag cgaattcggg ataagcaaaa gagagttgct tcgctcttac    1500
tttctggccg cagcaaccat attcgaaccg gagagaactc aagagaggct tctgtgggcc    1560
aaaaccagaa ttctttctaa gatgatcact tcatttgtca acattagtgg aacaacacta    1620
tctttggact acaatttcaa tggcctcgat gaaataatta gtagtgccaa tgaagatcaa    1680
ggactggctg ggactctgct ggcaaccttc catcaacttc tagacggatt cgatatatac    1740
actctccatc aactcaaaca tgtttggagc caatggttca tgaaagtgca gcaaggagag    1800
ggaagcggcg gggaagacgc ggtgctccta gcgaacacgc tcaacatctg cgccggcctc    1860
aacgaagacg tgttgtccaa caatgaatac acggctctgt ccaccctcac aaataaaatc    1920
tgcaatcgcc tcgcccaaat tcaagacaat aagattctcc aagttgtgga tgggagcata    1980
aaggataagg agctagaaca ggatatgcag gcgttggtga agttagtgct tcaagaaaat    2040
ggcggcgccg tagacagaaa catcagacac acgttttgt cggtttccaa gactttctac    2100
tacgatgcct accacgacga tgagacgacc gatcttcata tcttcaaagt actctttcga    2160
ccggttgtag gtggttctgg tggtgcgaaa atgaaagaga atttcaagag ggaagacgat    2220
aaatttccaa cgacaacgac tcttcgatcg gaagatatac cctctaattt gtgtataatc    2280
gacacccttc aaaggttggg ggtcgatcaa ttcttccaat atgaaatcaa cactattcta    2340
```

-continued

```
gataacacat tcaggttgtg gcaagaaaaa cacaaagtta tatatggcaa tgttactact    2400
catgcaatgg catttaggct tttgcgagtg aaaggatacg aagtttcatc agaggagttg    2460
gctccatatg gtaaccaaga ggctgttagc cagcaaacaa atgacctgcc gatgattatt    2520
gagctttata gagcagcaaa tgagagaata tatgaagaag agaggagtct tgaaaaaatt    2580
cttgcttgga ctaccatctt tctcaataag caagtgcaag ataactcaat tcccgacaaa    2640
aaactgcaca aactggtgga attctacttg aggaattaca aaggcataac cataagattg    2700
ggagctagac gaaacctcga gctatatgac atgacctact atcaagctct gaaatctaca    2760
aacaggttct ctaatttatg caacgaagat tttctagttt tcgcaaagca agatttcgat    2820
atacatgaag cccagaacca gaaggacttc aacaactgc aaaggtggta tgcagattgt    2880
aggttggaca ccttaaactt tggaagagat gtagttatta ttgctaatta tttggcttca    2940
ttaattattg gtgatcatgc gtttgactat gttcgtctcg catttgccaa aacatctgtg    3000
cttgtaacaa ttatggatga ttttttcgac tgtcatggct ctagtcaaga gtgtgacaag    3060
atcattgaat tagtaaaaga atggaaggag aatccggatg cagagtacgg atctgaggag    3120
cttgagatcc tttttatggc gttgtacaat acagtaaatg agttggcgga gagggctcgt    3180
gttgaacagg ggcgtagtgt caaagagttt ctagtcaaac tgtgggttga aatactctca    3240
gctttcaaga tagaattaga tacatggagc aatggcacgc agcaaagctt cgatgaatac    3300
atttcttcgt cgtggttgtc gaacggttcc cggctgacag gtctcctgac gatgcaattc    3360
gtcggagtaa aattgtccga tgaaatgctt atgagtgaag agtgcactga tttggctagg    3420
catgtctgta tggtcggccg gctgctcaac gacgtgtgca gttctgagag ggagcgcgag    3480
gaaaatattg caggaaaaag ttatagcatt ctactagcaa ctgagaaaga tggaagaaaa    3540
gttagtgaag atgaagccat tgcagagatc aatgaaatgg ttgaatatca ctggagaaaa    3600
gtgttgcaga ttgtgtataa aaagaaagc attttgccaa gaagatgcaa agatgtattt    3660
ttggagatgg ctaagggtac gttttatgct tatgggatca cgatgaatt gacttctcct    3720 cagcaatcca aggaagatat gaaatccttt gtcttttga                          3759
```

<210> SEQ ID NO 88
<211> LENGTH: 1252
<212> TYPE: PRT
<213> ORGANISM: Artificial sequence
<220> FEATURE:
<223> OTHER INFORMATION: Fusion polypeptide containing a LPP synthase
      and a sclareol synthase from Salvia sclarea

<400> SEQUENCE: 88

```
Met Ala Ser Gln Ala Ser Glu Lys Asp Ile Ser Leu Val Gln Thr Pro
1               5                   10                  15

His Lys Val Glu Val Asn Glu Lys Ile Glu Glu Ser Ile Glu Tyr Val
            20                  25                  30

Gln Asn Leu Leu Met Thr Ser Gly Asp Gly Arg Ile Ser Val Ser Pro
        35                  40                  45

Tyr Asp Thr Ala Val Ile Ala Leu Ile Lys Asp Leu Lys Gly Arg Asp
    50                  55                  60

Ala Pro Gln Phe Pro Ser Cys Leu Glu Trp Ile Ala His His Gln Leu
65                  70                  75                  80

Ala Asp Gly Ser Trp Gly Asp Glu Phe Phe Cys Ile Tyr Asp Arg Ile
                85                  90                  95

Leu Asn Thr Leu Ala Cys Val Val Ala Leu Lys Ser Trp Asn Leu His
            100                 105                 110
```

-continued

Ser Asp Ile Ile Glu Lys Gly Val Thr Tyr Ile Lys Glu Asn Val His
    115                 120                 125
Lys Leu Lys Gly Ala Asn Val Glu His Arg Thr Ala Gly Phe Glu Leu
130                 135                 140
Val Val Pro Thr Phe Met Gln Met Ala Thr Asp Leu Gly Ile Gln Asp
145                 150                 155                 160
Leu Pro Tyr Asp His Pro Leu Ile Lys Glu Ile Ala Asp Thr Lys Gln
                165                 170                 175
Gln Arg Leu Lys Glu Ile Pro Lys Asp Leu Val Tyr Gln Met Pro Thr
            180                 185                 190
Asn Leu Leu Tyr Ser Leu Glu Gly Leu Gly Asp Leu Trp Glu Arg
        195                 200                 205
Leu Leu Lys Leu Gln Ser Gly Asn Gly Ser Phe Leu Thr Ser Pro Ser
    210                 215                 220
Ser Thr Ala Ala Val Leu Met His Thr Lys Asp Glu Lys Cys Leu Lys
225                 230                 235                 240
Tyr Ile Glu Asn Ala Leu Lys Asn Cys Asp Gly Gly Ala Pro His Thr
                245                 250                 255
Tyr Pro Val Asp Ile Phe Ser Arg Leu Trp Ala Ile Asp Arg Leu Gln
            260                 265                 270
Arg Leu Gly Ile Ser Arg Phe Phe Gln His Glu Ile Lys Tyr Phe Leu
        275                 280                 285
Asp His Ile Glu Ser Val Trp Glu Glu Thr Gly Val Phe Ser Gly Arg
    290                 295                 300
Tyr Thr Lys Phe Ser Asp Ile Asp Asp Thr Ser Met Gly Val Arg Leu
305                 310                 315                 320
Leu Lys Met His Gly Tyr Asp Val Asp Pro Asn Val Leu Lys His Phe
                325                 330                 335
Lys Gln Gln Asp Gly Lys Phe Ser Cys Tyr Ile Gly Gln Ser Val Glu
            340                 345                 350
Ser Ala Ser Pro Met Tyr Asn Leu Tyr Arg Ala Ala Gln Leu Arg Phe
        355                 360                 365
Pro Gly Glu Glu Val Leu Glu Glu Ala Thr Lys Phe Ala Phe Asn Phe
    370                 375                 380
Leu Gln Glu Met Leu Val Lys Asp Arg Leu Gln Glu Arg Trp Val Ile
385                 390                 395                 400
Ser Asp His Leu Phe Asp Glu Ile Lys Leu Gly Leu Lys Met Pro Trp
                405                 410                 415
Tyr Ala Thr Leu Pro Arg Val Glu Ala Ala Tyr Tyr Leu Asp His Tyr
            420                 425                 430
Ala Gly Ser Gly Asp Val Trp Ile Gly Lys Ser Phe Tyr Arg Met Pro
        435                 440                 445
Glu Ile Ser Asn Asp Thr Tyr Lys Glu Leu Ala Ile Leu Asp Phe Asn
    450                 455                 460
Arg Cys Gln Thr Gln His Gln Leu Glu Trp Ile His Met Gln Glu Trp
465                 470                 475                 480
Tyr Asp Arg Cys Ser Leu Ser Glu Phe Gly Ile Ser Arg Glu Leu
                485                 490                 495
Leu Arg Ser Tyr Phe Leu Ala Ala Ala Thr Ile Phe Glu Pro Glu Arg
            500                 505                 510
Thr Gln Glu Arg Leu Leu Trp Ala Lys Thr Arg Ile Leu Ser Lys Met
        515                 520                 525
Ile Thr Ser Phe Val Asn Ile Ser Gly Thr Thr Leu Ser Leu Asp Tyr
    530                 535                 540

```
Asn Phe Asn Gly Leu Asp Glu Ile Ile Ser Ser Ala Asn Glu Asp Gln
545                 550                 555                 560

Gly Leu Ala Gly Thr Leu Leu Ala Thr Phe His Gln Leu Leu Asp Gly
                565                 570                 575

Phe Asp Ile Tyr Thr Leu His Gln Leu Lys His Val Trp Ser Gln Trp
                580                 585                 590

Phe Met Lys Val Gln Gln Gly Glu Gly Ser Gly Gly Glu Asp Ala Val
                595                 600                 605

Leu Leu Ala Asn Thr Leu Asn Ile Cys Ala Gly Leu Asn Glu Asp Val
                610                 615                 620

Leu Ser Asn Asn Glu Tyr Thr Ala Leu Ser Thr Leu Thr Asn Lys Ile
625                 630                 635                 640

Cys Asn Arg Leu Ala Gln Ile Gln Asp Asn Lys Ile Leu Gln Val Val
                645                 650                 655

Asp Gly Ser Ile Lys Asp Lys Glu Leu Glu Gln Asp Met Gln Ala Leu
                660                 665                 670

Val Lys Leu Val Leu Gln Glu Asn Gly Gly Ala Val Asp Arg Asn Ile
                675                 680                 685

Arg His Thr Phe Leu Ser Val Ser Lys Thr Phe Tyr Tyr Asp Ala Tyr
690                 695                 700

His Asp Glu Thr Thr Asp Leu His Ile Phe Lys Val Leu Phe Arg
705                 710                 715                 720

Pro Val Gly Gly Ser Gly Gly Ala Lys Met Lys Glu Asn Phe Lys
                725                 730                 735

Arg Glu Asp Asp Lys Phe Pro Thr Thr Thr Leu Arg Ser Glu Asp
                740                 745                 750

Ile Pro Ser Asn Leu Cys Ile Ile Asp Thr Leu Gln Arg Leu Gly Val
                755                 760                 765

Asp Gln Phe Phe Gln Tyr Glu Ile Asn Thr Ile Leu Asp Asn Thr Phe
                770                 775                 780

Arg Leu Trp Gln Glu Lys His Lys Val Ile Tyr Gly Asn Val Thr Thr
785                 790                 795                 800

His Ala Met Ala Phe Arg Leu Leu Arg Val Lys Gly Tyr Glu Val Ser
                805                 810                 815

Ser Glu Glu Leu Ala Pro Tyr Gly Asn Gln Glu Ala Val Ser Gln Gln
                820                 825                 830

Thr Asn Asp Leu Pro Met Ile Ile Glu Leu Tyr Arg Ala Ala Asn Glu
                835                 840                 845

Arg Ile Tyr Glu Glu Glu Arg Ser Leu Glu Lys Ile Leu Ala Trp Thr
850                 855                 860

Thr Ile Phe Leu Asn Lys Gln Val Gln Asp Asn Ser Ile Pro Asp Lys
865                 870                 875                 880

Lys Leu His Lys Leu Val Glu Phe Tyr Leu Arg Asn Tyr Lys Gly Ile
                885                 890                 895

Thr Ile Arg Leu Gly Ala Arg Arg Asn Leu Glu Leu Tyr Asp Met Thr
                900                 905                 910

Tyr Tyr Gln Ala Leu Lys Ser Thr Asn Arg Phe Ser Asn Leu Cys Asn
                915                 920                 925

Glu Asp Phe Leu Val Phe Ala Lys Gln Asp Phe Asp Ile His Glu Ala
                930                 935                 940

Gln Asn Gln Lys Gly Leu Gln Gln Leu Gln Arg Trp Tyr Ala Asp Cys
945                 950                 955                 960

Arg Leu Asp Thr Leu Asn Phe Gly Arg Asp Val Val Ile Ile Ala Asn
```

-continued

```
                965                 970                 975
Tyr Leu Ala Ser Leu Ile Ile Gly Asp His Ala Phe Asp Tyr Val Arg
            980                 985                 990

Leu Ala Phe Ala Lys Thr Ser Val Leu Val Thr Ile Met Asp Asp Phe
            995                1000                1005

Phe Asp Cys His Gly Ser Ser Gln Glu Cys Asp Lys Ile Ile Glu
    1010                1015                1020

Leu Val Lys Glu Trp Lys Glu Asn Pro Asp Ala Glu Tyr Gly Ser
    1025                1030                1035

Glu Glu Leu Glu Ile Leu Phe Met Ala Leu Tyr Asn Thr Val Asn
    1040                1045                1050

Glu Leu Ala Glu Arg Ala Arg Val Glu Gln Gly Arg Ser Val Lys
    1055                1060                1065

Glu Phe Leu Val Lys Leu Trp Val Glu Ile Leu Ser Ala Phe Lys
    1070                1075                1080

Ile Glu Leu Asp Thr Trp Ser Asn Gly Thr Gln Gln Ser Phe Asp
    1085                1090                1095

Glu Tyr Ile Ser Ser Ser Trp Leu Ser Asn Gly Ser Arg Leu Thr
    1100                1105                1110

Gly Leu Leu Thr Met Gln Phe Val Gly Val Lys Leu Ser Asp Glu
    1115                1120                1125

Met Leu Met Ser Glu Glu Cys Thr Asp Leu Ala Arg His Val Cys
    1130                1135                1140

Met Val Gly Arg Leu Leu Asn Asp Val Cys Ser Ser Glu Arg Glu
    1145                1150                1155

Arg Glu Glu Asn Ile Ala Gly Lys Ser Tyr Ser Ile Leu Leu Ala
    1160                1165                1170

Thr Glu Lys Asp Gly Arg Lys Val Ser Glu Asp Glu Ala Ile Ala
    1175                1180                1185

Glu Ile Asn Glu Met Val Glu Tyr His Trp Arg Lys Val Leu Gln
    1190                1195                1200

Ile Val Tyr Lys Lys Glu Ser Ile Leu Pro Arg Arg Cys Lys Asp
    1205                1210                1215

Val Phe Leu Glu Met Ala Lys Gly Thr Phe Tyr Ala Tyr Gly Ile
    1220                1225                1230

Asn Asp Glu Leu Thr Ser Pro Gln Gln Ser Lys Glu Asp Met Lys
    1235                1240                1245

Ser Phe Val Phe
    1250
```